(12) United States Patent
Masson et al.

(10) Patent No.: US 8,461,183 B2
(45) Date of Patent: Jun. 11, 2013

(54) PPAR AGONIST COMPOUNDS, PREPARATION AND USES

(75) Inventors: Christophe Masson, Chateaudun (FR); Karine Caumont-Bertrand, Freilinghein (FR)

(73) Assignee: Genfit, Loos (FR)

( * ) Notice: Subject to any disclaimer, the term of this patent is extended or adjusted under 35 U.S.C. 154(b) by 179 days.

(21) Appl. No.: 12/736,967

(22) PCT Filed: May 26, 2009

(86) PCT No.: PCT/FR2009/050980
§ 371 (c)(1), (2), (4) Date: Nov. 26, 2010

(87) PCT Pub. No.: WO2009/153496
PCT Pub. Date: Dec. 23, 2009

(65) Prior Publication Data
US 2011/0195993 A1   Aug. 11, 2011

(30) Foreign Application Priority Data
May 26, 2008   (FR) ..................................... 08 53415

(51) Int. Cl.
*C07D 401/04* (2006.01)
*C07D 213/64* (2006.01)
*A61K 31/4418* (2006.01)

(52) U.S. Cl.
USPC ........... 514/318; 514/345; 514/351; 514/352; 546/194; 546/296; 546/300; 546/301; 546/302; 546/304

(58) Field of Classification Search
None
See application file for complete search history.

(56) References Cited

U.S. PATENT DOCUMENTS

| 2003/0212100 A1 | 11/2003 | Tsunoda et al. |
| 2005/0096336 A1 | 5/2005 | Ackermann et al. |
| 2005/0096362 A1 | 5/2005 | Kuo et al. |
| 2006/0074246 A1 | 4/2006 | Kuo et al. |
| 2009/0131489 A1 | 5/2009 | Kuo et al. |

FOREIGN PATENT DOCUMENTS

| EP | 1 266 888 | 12/2002 |
| WO | 03/084916 | 10/2003 |
| WO | WO 2005016862 | * 2/2005 |
| WO | 2005/041959 | 5/2005 |
| WO | 2008/066356 | 6/2008 |

OTHER PUBLICATIONS

International Search Report for PCT/FR2009/050980, mailed Feb. 5, 2010.
Written Opinion of the International Searching Authority for PCT/FR2009/050980, mailed Feb. 5, 2010.

* cited by examiner

*Primary Examiner* — Zinna Northington Davis
(74) *Attorney, Agent, or Firm* — Nixon & Vanderhye P.C.

(57) ABSTRACT

The present invention relates to novel PPAR agonist compounds as well as pharmaceutical compositions containing them. The compounds according to the invention are of quite particular therapeutic interest, notably for treating diabetes and/or dyslipidemias, as well as for preventing cardiovascular pathologies.

17 Claims, 24 Drawing Sheets

Figure 1:
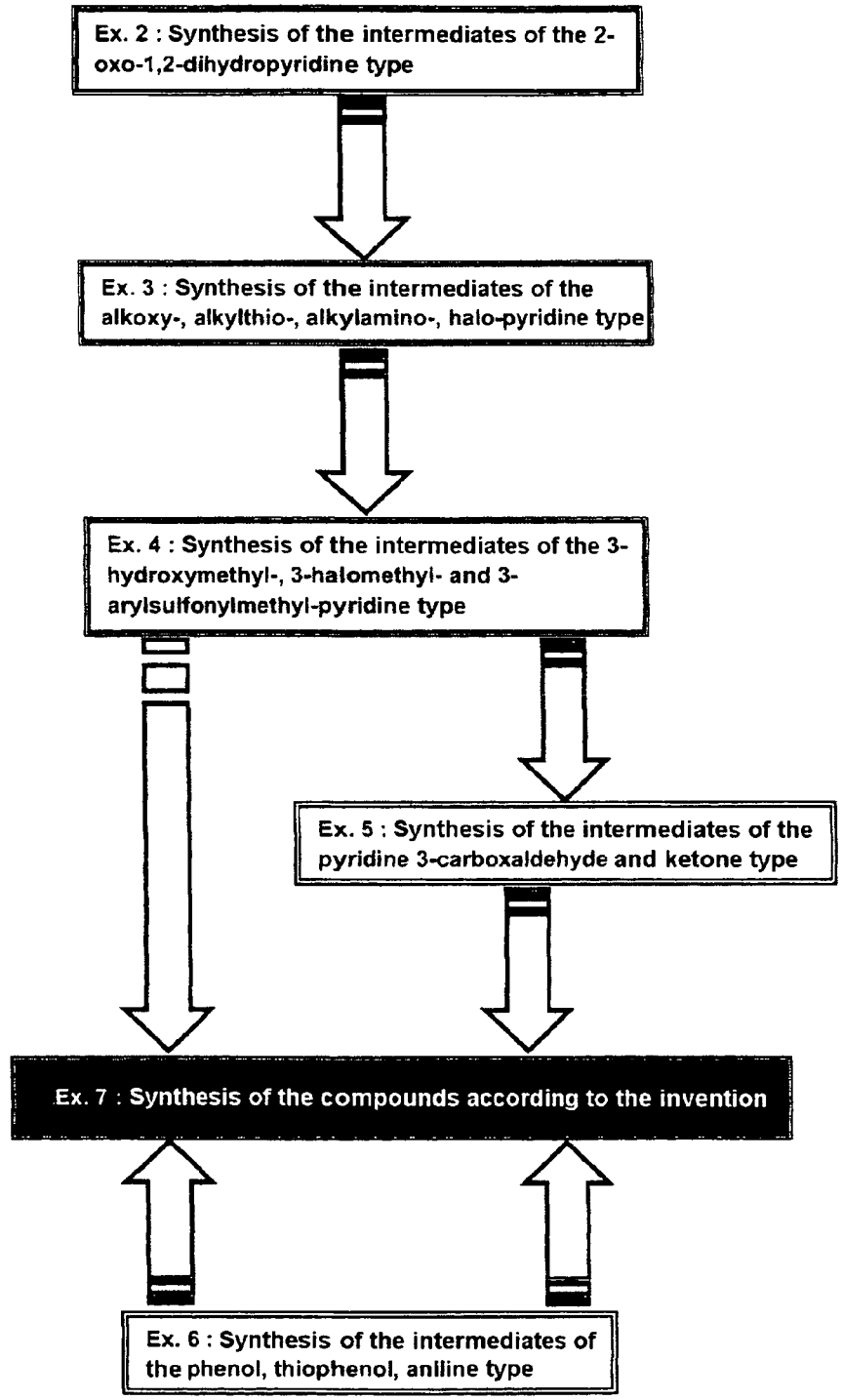

$X_1 = X_2 = Ph$      2-3 : $X_1 = X_2 = Ph$ 2-1 : $X_1 = Ph$      2-4 : $X_1 = Ph$
$X_2 = X_3 = H$      $X_2 = Br$, $X_3 = H$ suitable intermediate 2 → suitable intermediate 3

2,6-dimethoxynicotinic acid : $X_1=G=OMe$, $X_2=X_3=H$ 3-19 : $X_1=G=OMe$, $X_2=X_3=H$ 3-20 : $X_1=G=OMe$, $X_2=Br$, $X_3=H$ 3-10 : $X_1=H$, $G=OMe$, $X_2=Br$, $X_3=H$ 3-10 or 3-20 →(Prot. SI) suitable intermediate 3

2-1: $X_1=Ph$, $X_2=X_3=H$ 3-5 : $X_1=Ph$, $X_2=X_3=H$ 3-6 : $X_1=Ph$, G= piperidinyl, $X_2=X_3=H$ 3-8 : $X_1=Ph$, G= SPh, $X_2=X_3=H$ 3-14 : $X_1=Ph$, G= SEt, $X_2=X_3=H$ suitable intermediate 3 → suitable intermediate 4

4-1: $X_1$=Ph, G=OMe
$X_2$=$X_3$=H 4-15: $X_1$=Ph, G=OMe
$X_2$=$X_3$=H 5-1: $X_1$=Ph, G=OMe
$X_2$=$X_3$=$R_1$=H 4-11: $X_1$=Ph, G=OMe, $R_2$=Et
$R_1$=$X_2$=$X_3$=H 4-1: $X_1$=Ph, G=OMe
$X_2$=$X_3$=H 4-16: $X_1$=Ph, G=OMe
$X_2$=$X_3$=H suitable intermediate 4 → suitable intermediate 5

4-2: $X_1$=Ph, G=OtBu
$X_2$=$X_3$=$R_1$=H 5-2: $X_1$=Ph, G=OtBu
$X_2$=$X_3$=$R_1$=H 2-3: $X_1$=$X_2$=Ph
$X_3$=H $X_1$=$X_2$=Ph
$X_3$=H 5-5: $X_1$=$X_2$=Ph, G=OMe
$X_3$=H 3-(4-aminophenyl)propanoic acid
$X_4=X_5=R_3=R_4=H$ 6-15 : R'''a=Et
$X_4=X_5=R_3=R_4=H$ suitable
4-nitro-1-carbonylbenzene suitable
intermediate 6

| | $Y_1$ = -NR $Y_2$ =oxygen | | $Y_1$ = -NR $Y_2$ =sulfur | |
|---|---|---|---|---|
| $X_1$=different from hydrogen $X_2$ = $X_3$=hydrogen | Cpd 4  | Cpd 5  | Cpd 11  | Cpd 16  |
| | Cpd 8  | Cpd 9  | Cpd 22  | Cpd 23  |
| | Cpd 10  | Cpd 12  | Cpd 27  | Cpd 30  |
| | Cpd 13  | Cpd 14  | Cpd 32  | |
| | Cpd 35  | | | |
| $X_2$=different from hydrogen $X_1$ = $X_3$= hydrogen | | | Cpd 26  | |
| $X_2$ and $X_1$ different from hydrogen $X_3$= hydrogen | | | Cpd 28  Cpd 29  | |

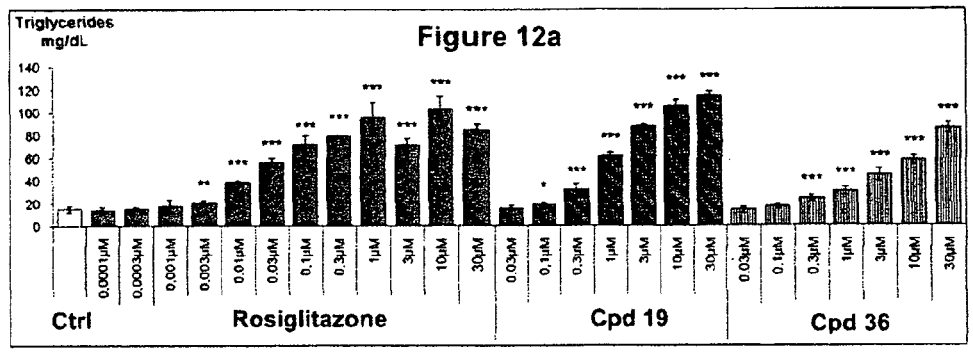
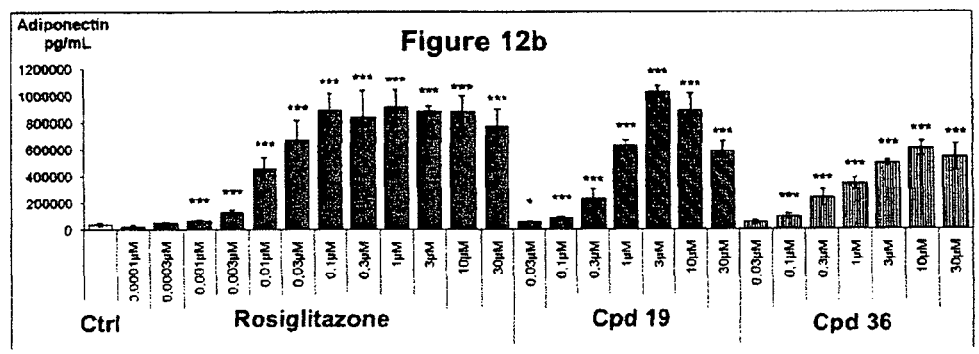
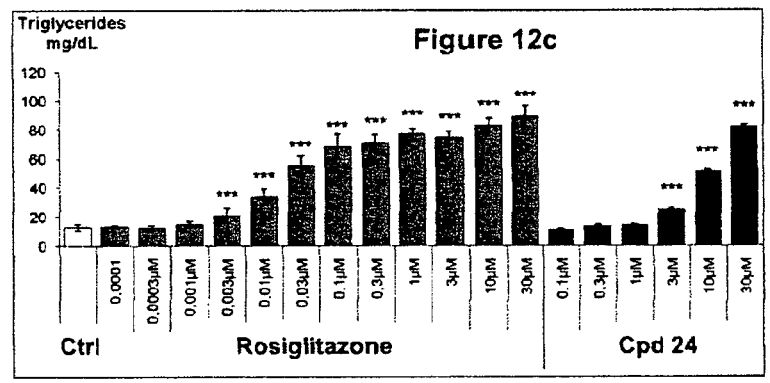
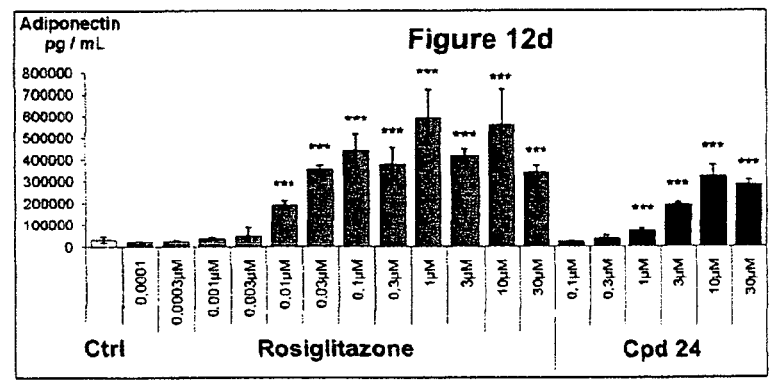

SEQUENCE LISTING

<160> NUMBER OF SEQ ID NOS: 12

<210> SEQ ID NO 1
<211> LENGTH: 22
<212> TYPE: DNA
<213> ORGANISM: ArtificiAL
<220> FEATURE:
<223> OTHER INFORMATION: PDK4 sense primer

<400> SEQUENCE: 1
tactccactg ctccaacacc tg                                        22

<210> SEQ ID NO 2
<211> LENGTH: 20
<212> TYPE: DNA
<213> ORGANISM: Artificial
<220> FEATURE:
<223> OTHER INFORMATION: PDK4 antisense primer

<400> SEQUENCE: 2
gttcttcggt tccctgcttg                                                  20

<210> SEQ ID NO 3
<211> LENGTH: 20
<212> TYPE: DNA
<213> ORGANISM: Artificial
<220> FEATURE:
<223> OTHER INFORMATION: ACO sense primer

<400> SEQUENCE: 3
gaagccagcg ttacgaggtg                                                  20

<210> SEQ ID NO 4
<211> LENGTH: 20
<212> TYPE: DNA
<213> ORGANISM: Artificial
<220> FEATURE:
<223> OTHER INFORMATION: ACO antisense primer

<400> SEQUENCE: 4
tggagttctt gggacgggtg                                                  20

<210> SEQ ID NO 5
<211> LENGTH: 20
<212> TYPE: DNA
<213> ORGANISM: Artificial
<220> FEATURE:
<223> OTHER INFORMATION: ApoCIII sense primer

<400> SEQUENCE: 5
ctcttggctc tcctggcatc                                                  20

<210> SEQ ID NO 6
<211> LENGTH: 20
<212> TYPE: DNA
<213> ORGANISM: Artificial
<220> FEATURE:
<223> OTHER INFORMATION: ApoCIII antisense primer

<400> SEQUENCE: 6
gcatcctgga ccgtcttgga                                                  20

<210> SEQ ID NO 7
<211> LENGTH: 22
<212> TYPE: DNA
<213> ORGANISM: Artificial
<220> FEATURE:
<223> OTHER INFORMATION: CPT1b sense primer

<400> SEQUENCE: 7
ggactgagac tgtgcgttcc tg                                               22

<210> SEQ ID NO 8
<211> LENGTH: 20
<212> TYPE: DNA
<213> ORGANISM: Artificial
<220> FEATURE:
<223> OTHER INFORMATION: CPT1b antisense primer

<400> SEQUENCE: 8
agtgcttggc ggatgtggtt                                                  20

```
<210> SEQ ID NO 9
<211> LENGTH: 24
<212> TYPE: DNA
<213> ORGANISM: Artificial
<220> FEATURE:
<223> OTHER INFORMATION: UCP2 sense primer

<400> SEQUENCE: 9
gtcggagata ccagagcact gtcg                                          24

<210> SEQ ID NO 10
<211> LENGTH: 20
<212> TYPE: DNA
<213> ORGANISM: Artificial
<220> FEATURE:
<223> OTHER INFORMATION: UCP2 antisense primer

<400> SEQUENCE: 10
cacatcaaca ggggaggcga                                               20

<210> SEQ ID NO 11
<211> LENGTH: 25
<212> TYPE: DNA
<213> ORGANISM: Artificial
<220> FEATURE:
<223> OTHER INFORMATION: 36B4 sense primer

<400> SEQUENCE: 11
catgctcaac atctccccct tctcc                                         25

<210> SEQ ID NO 12
<211> LENGTH: 25
<212> TYPE: DNA
<213> ORGANISM: Artificial
<220> FEATURE:
<223> OTHER INFORMATION: 36B4 antisense primer

<400> SEQUENCE: 12
gggaaggtgt aatccgtctc cacag                                         25
```

PPAR AGONIST COMPOUNDS, PREPARATION AND USES

This application is the U.S. national phase of International Application No. PCT/FR2009/050980 filed 26 May 2009, which designated the U.S. and claims priority to France Application No. 0853415 filed 26 May 2008, the entire contents of each of which are hereby incorporated by reference.

The present invention relates to compounds of therapeutic interest, intended notably for treating diabetes and/or dyslipidemias. The invention also relates to pharmaceutical compositions comprising said compounds.

Diabetes and dyslipidemias (high plasma levels of LDL cholesterol and of triglycerides, low HDL cholesterol, etc.) are included among the clearly identified cardiovascular risk factors that predispose an individual to develop a cardiovascular pathology (The Atlas of Heart Disease and Stroke, edited by Mackay J and Mensah M, published by World Health Organization, 2004). These risk factors are additional to the risk factors associated with lifestyle such as smoking, physical inactivity and an unbalanced diet. There is a synergistic effect between these various factors: the simultaneous presence of several of them leads to a dramatic worsening of cardiovascular risk and it is then best to talk of global risk for cardiovascular diseases. The prevalence of dyslipidemias reached 43.6% of the population in 2004 in the main developed countries. The prevalence of diabetes, currently showing a marked increase, will become increasingly significant in the epidemiology of cardiovascular diseases. It is estimated at 7.6% of the population for 2010 (Fox-Tucker J, The Cardiovascular Market Outlook to 2010, Business Insights Reports, 2005).

According to the International Atherosclerosis Society, cardiovascular diseases represent the primary cause of mortality in the industrialized countries and are becoming more and more common in the developing countries. These diseases are notably coronary diseases, cerebral ischemia and peripheral arterial diseases. These data justify the adoption of energetic measures for significantly reducing cardiovascular morbidity and mortality. Equally, the need to find effective treatments, capable of acting on the risk factors of cardiovascular diseases and on their consequences, is now of global urgency, also in view of recent disappointing results with candidate drugs (Krause B, 2008).

Among the various nuclear receptors that can be therapeutic targets (Hansen M K and Connolly T M, 2008), the involvement of Peroxisome Proliferator-Activated Receptors (PPARs) in pathologies of this type is now very well established (Blaschke F et al., 2006; Gilde A J et al., 2006; Gervois P et al., 2007). The PPAR family comprises three isoforms, designated α, γ and δ (also called β), each encoded by a different gene. These receptors, which form part of the superfamily of nuclear receptors and of transcription factors, have a major role in regulation of lipid and carbohydrate metabolism.

PPARα controls lipid metabolism (hepatic and muscular) and glucose homeostasis, and influences intracellular metabolism of lipids and sugars by direct control of transcription of the genes coding for proteins involved in lipid homeostasis. PPARα also exerts anti-inflammatory and antiproliferative effects and prevents the proatherogenic effects of accumulation of cholesterol in macrophages by stimulating the outflow of cholesterol (Lefebvre P et al., 2006). PPARγ is a key regulator of adipogenesis. It is also involved in the lipid metabolism of mature adipocytes, in glucose homeostasis, in insulin resistance, in inflammation, in accumulation of cholesterol at the macrophage level and in cellular proliferation (Lehrke M and Lazar M A, 2005). PPARγ consequently plays a role in the pathogenesis of obesity, insulin resistance and diabetes. PPARδ is involved in controlling lipid and carbohydrate metabolism, in the energy balance, in neurodegeneration, in obesity, in the formation of foam cells and in inflammation (Gross B et al., 2005).

These multiple properties make PPARs therapeutic targets of interest for the treatment of diabetes and dyslipidemias, and for the prevention of cardiovascular diseases. Ligands of PPARs are already known, some are marketed and prescribed in the treatment of some of the pathologies mentioned above, and their toxicology has been investigated (Peraza M et al., 2006). We may mention activators of PPARα, such as fibrates (fenofibrate, bezafibrate, ciprofibrate, gemfibrozil), which are used in clinical practice for treating certain dyslipidemias by increasing plasma levels of HDL (High Density Lipoprotein) and by lowering triglycerides (Hourton D et al. 2001). Moreover, thiazolidinediones (rosiglitazone and pioglitazone), ligands of PPARγ, are used in the treatment of type 2 diabetes. Ligands of PPARδ are also known (such as L-165041, GW501516 and KD3010). Among the documents of the prior art mentioning similar compounds, patent applications WO 03/084916, WO 08/152333, WO 05/041959, WO 08/066356, EP 1266888, and US 2005096336 describe PPAR receptor agonists.

The invention proposes novel compounds that are agonists of PPARs (PPARα and/or PPARγ and/or PPARδ), and in particular are suitable for the therapeutic and/or prophylactic treatment of diabetes, dyslipidemias, insulin resistance, pathologies associated with metabolic syndrome, atherosclerosis, obesity, hypertension and/or inflammatory diseases. These PPAR agonist compounds can also be particularly effective for reducing cardiovascular risk, and for preventing cardiovascular diseases, notably those associated with disorders of lipid and/or carbohydrate metabolism.

These and other aims are achieved by compounds of the following general formula (I):

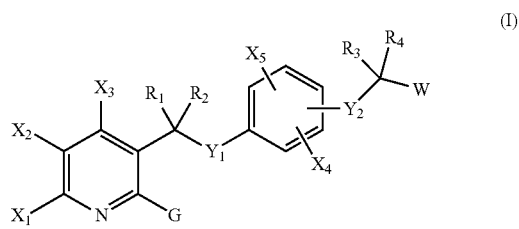

in which,

G represents:
  a radical —$OR_a$, —$SR_a$; or
  a radical —$NR_aR_b$;
  $R_a$ being selected from an alkyl radical with 1 to 6 carbon atoms or alkenyl radical with 2 to 6 carbon atoms, a ring with 3 to 14 atoms, a phenyl radical, a phenylalkyl radical with the alkyl moiety having 1 to 3 carbon atoms;
  $R_b$ being selected from a hydrogen atom, an alkyl radical with 1 to 6 carbon atoms or alkenyl radical with 2 to 6 carbon atoms, a ring with 3 to 14 atoms, a phenyl radical, or a phenylalkyl radical with the alkyl moiety having 1 to 3 carbon atoms;
  and $R_a$ and $R_b$ can form, together and with the nitrogen atom to which they are bound, a heterocycle with 3 to 8 atoms;

$R_1$ and $R_2$, which may be identical or different, represent a hydrogen atom or an alkyl radical with 1 to 6 carbon atoms or alkenyl radical with 2 to 6 carbon atoms;

and $R_1$ and $R_2$ can form, together and with the carbon atom to which they are bound, a carbocycle with 3 to 6 carbon atoms;

$Y_1$ represents:
  an oxygen, sulfur or selenium atom, or
  a group —NR—, in which R has the same definition as $R_b$;

$Y_2$ represents:
  an oxygen, sulfur or selenium atom, or
  a radical —$CR_5R_6$—; with $R_5$ and $R_6$, which may be identical or different, selected from a hydrogen atom or halogen atom, an alkyl radical with 1 to 6 carbon atoms or an alkenyl or alkynyl radical with 2 to 6 carbon atoms, a ring with 3 to 6 atoms, a phenylalkyl radical with the alkyl moiety having 1 to 3 carbon atoms, and $R_5$ and $R_6$ can form, together and with the carbon atom to which they are bound, a ring with 3 to 6 atoms;

$X_1, X_2, X_3$ represent independently a hydrogen atom or halogen atom, an alkyl radical with 1 to 6 carbon atoms or alkenyl radical with 2 to 6 carbon atoms, a group —$OR'_a$, —$SR'_a$, —$NR'_aR'_b$, a ring with 5 to 14 atoms, or a phenylalkyl radical with the alkyl moiety having 1 to 3 carbon atoms, with at least one of the groups $X_1, X_2$ and $X_3$ different from a hydrogen atom and from a halogen atom, and $X_1, X_2$ and $X_3$ can form two at a time, with the two carbon atoms to which they are bound, a carbocycle with 6 carbon atoms;

$R'_a$ and $R'_b$, which may be identical or different, having the same definitions as $R_a$ and $R_b$;

$X_4$ and $X_5$ represent independently a hydrogen atom or halogen atom, an alkyl radical with 1 to 6 carbon atoms or alkenyl radical with 2 to 6 carbon atoms, a group —$OR''_a$, —$SR''_a$ or —$NR''_aR''_b$, a ring with 3 to 14 atoms, a phenyl radical, or a phenylalkyl radical with the alkyl moiety having 1 to 3 carbon atoms;

and $X_4$ and $X_5$ can be bound to two adjacent carbon atoms and form, together and with said adjacent carbon atoms, a ring with 6 atoms;

$R-_a$ and $R''_b$, which may be identical or different, having the same definitions as $R_a$ and $R_b$;

$R_3$ and $R_4$, which may be identical or different, represent a hydrogen atom or halogen atom, an alkyl radical with 1 to 6 carbon atoms or alkenyl radical with 2 to 6 carbon atoms, a ring with 3 to 14 atoms, a phenyl radical, or a phenylalkyl radical with the alkyl moiety having 1 to 3 carbon atoms;

$R_3$ and $R_4$ can form, together and with the carbon atom to which they are bound, a ring with 3 to 6 atoms;

W represents:
  a carboxyl radical —COON; or
  a function derived from the carboxylic acid function, selected from —$COOR'''_a$, —$COSR'''_a$, —$CONR'''_aR'''_b$, —$CSNR'''_aR'''_b$, —$CONH_2$; or
  a bioisosteric group of the carboxyl radical, selected from:
  an acylsulfonamide radical (—$CONHSO_2R'''_a$);
  a hydrazide radical (—$CONHNR'''_aR'''_b$);
  a radical selected from the thiazolidinedione, oxazolidinedione, tetrazole, oxadiazolone, triazolone, triazole, 3-alkyltriazole, or imidazolidinedione rings;

$R'''_a$ and $R'''_b$, which may be identical or different, having the same definitions as $R_a$ and $R_b$.

Within the scope of the present invention, the following definitions are applicable:

Alkyl, alkenyl or alkynyl radicals with n carbon atoms mean, according to the invention, linear, saturated or unsaturated, branched or unbranched hydrocarbon radicals, formed with a total of n carbon atoms (carbon atoms of the main chain and carbon atoms of the branchings), comprising from 1 to 12 carbon atoms and, more particularly, from 1 to 6 carbon atoms. This definition also includes alkyl, alkenyl or alkynyl radicals substituted with one or more halogen atoms. The alkyl radicals with 1 to 6 carbon atoms are preferably the methyl, ethyl, n-propyl, isopropyl, n-butyl, isobutyl, tert-butyl, sec-butyl, pentyl, neopentyl, n-hexyl or cyclohexyl radical. Alkyl radical having from 7 to 12 carbon atoms preferably means the octyl, decyl, or dodecyl radical. Alkenyl radical with 1 to 6 carbon atoms means hydrocarbon radicals having at least one double bond between two carbon atoms, of the —CH=CH— type, for example the ethenyl, propen-1-yl, propen-2-yl, buten-1-yl, buten-2-yl, penten-1-yl, penten-2-yl, 3-methyl-buten-2-yl radical. Alkynyl radical with 1 to 6 carbon atoms means hydrocarbon radicals having at least one triple bond between two carbon atoms, of the —C≡C— type, for example the ethynyl, propyn-1-yl, propyn-2-yl, butyn-1-yl, butyn-2-yl, pentyn-1-yl or pentyn-2-yl radical.

Halogen atom means an atom of fluorine, of chlorine, of bromine, or of iodine.

"Ring with n atoms" means, according to the invention, mono- or poly-cyclic radicals whose cyclic moiety is formed by a total of n atoms (in this case, n=3, 4, 5, 6, 7, 8, 9, 10, 11, 12, 13 or 14) and preferably comprising 3 to 7 carbon atoms. This cyclic radical can be saturated or unsaturated, optionally aromatic. It can be a carbocycle, i.e. a ring whose cyclic part is formed exclusively of carbon atoms. It can also be a heterocycle; in that case, at least one of the atoms of the cyclic part is a heteroatom, such as nitrogen, oxygen or sulfur. This definition of the rings according to the invention, including phenyl, notably includes rings substituted with one or more halogen atoms (and/or with one or more hydroxyl, thiol, cyano, nitro functions, and/or with one or more alkyl, alkenyl, alkyloxy, alkylthio radicals, having 1 to 6 carbon atoms, and/or with one or more phenyl or phenylalkyl radicals with the alkyl moiety having 1 to 3 carbon atoms, and said radicals themselves can be halogenated (such as perfluoroalkyls, for example —$CF_3$) and/or substituted with alkyl, alkenyl, alkyloxy, alkylthio groups, and/or with hydroxyl, cyano, thiol, nitro functions. As examples we may mention:

saturated carbocycles such as cyclopropyl, cyclobutyl, cyclopentyl, cyclohexyl, norbornyl, adamantyl, or cycloheptyl;

unsaturated, aromatic or partially aromatic carbocycles, such as cyclobutadiene, benzene (or phenyl group), pentalene, heptalene, naphthalene, or anthracene; among the aromatic carbocyclic groups, the phenyl or naphthyl group, substituted or unsubstituted, is quite particularly preferred;

saturated heterocycles such as pyrrolidine, dioxane, morpholine, piperidine, piperazine, 2-oxo-piperidine, or 2-oxo-pyrrolidine;

unsaturated, aromatic or nonaromatic heterocycles, such as pyridine, furan, pyran, pyrrole, thiophene, isoxazole, oxadiazole, oxazole, benzimidazole, indole, benzofuran, hexamethylamine, tetrazole, indoline, isoindole, isoindoline, benzothiophene, quinoline, or imidazole.

The terms "alkyloxy" and "alkylthio" refer respectively to an alkyl chain bound to the rest of the molecule via an oxygen atom (ether bond) or to an alkyl chain bound to the rest of the molecule via a sulfur atom (thioether bond). The term "alkyl" corresponds to the definition given previously. As examples of alkoxy, we may mention the methoxy, ethoxy, n-propyloxy, isopropyloxy, n-butyloxy, isobutyloxy, tert-butyloxy, sec-butyloxy or hexyloxy radicals. As examples of alkylthio, we may mention the methylthio, ethylthio, n-propylthio, isopropylthio, n-butylthio, isobutylthio, tert-butylthio, sec-butylthio or hexylthio radicals.

The term "phenylalkyl" denotes a radical of the alkyl type substituted with a phenyl group, the alkyl radical being as defined above. This definition notably includes phenylalkyl radicals whose phenyl group is substituted with one or more halogen atoms and/or with one or more alkyl radicals with 1 to 6 carbon atoms or alkenyl radicals with 2 to 6 carbon atoms, optionally themselves halogenated.

The concept of "bioisosteres of the carboxyl radical" refers to chemical groups functionally/biologically equivalent to a carboxyl radical (—COOH), i.e. they can replace the carboxyl radical of a compound without significantly changing the overall biological activity of said compound. Bioisosteric groups are generally used for improving the efficacy, selectivity, stability, or pharmacokinetics of molecules. Numerous bioisosteric groups of the carboxyl radical are known and are described extensively in the literature (Burger A, 1991; Lima L M and Barreiro E J, 2005). This applies notably to the following groups:

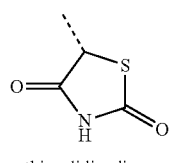

thiazolidinedione

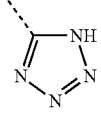

tetrazole

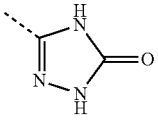

triazolone

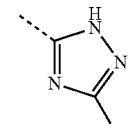

3-alkyl-triazole
(R = alkyl)

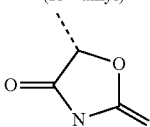

oxazolidinedione

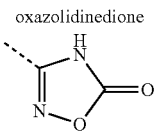

oxadiazolone

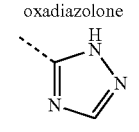

triazole

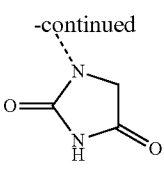

imidazolidinedione

The alkyl radical R of the triazole can be an alkyl radical as defined previously.

The concept of "functions derived from the carboxylic acid function" refers to functions susceptible to hydrolysis (notably to enzymatic hydrolysis) known by a person skilled in the art as being precursors of the carboxylic acid function. These functions are widely used for modifying the pharmacokinetic properties of carboxylated active molecules. They are notably esters, thioesters, amides and thioamides.

In general, the invention relates to compounds corresponding to general formula (I) as defined previously, in which, preferably:

G is selected from the methoxy, ethoxy, n-propyloxy, isopropyloxy, n-butyloxy, tert-butyloxy, sec-butyloxy, n-pentyloxy, cyclopentyloxy, n-hexyloxy, cyclohexyloxy, phenoxy, methylamine, dimethylamine, ethylamine, diethylamine, n-propylamine, dipropylamine, isopropylamine, diisopropylamine, n-butylamine, dibutylamine, tert-butylamine, n-hexylamine, dihexylamine, piperidine, pyrolidine, aniline, methylthio, ethylthio, n-propylthio, isopropylthio, n-butylthio, tert-butylthio, sec-butylthio, n-pentylthio, cyclopentylthio, n-hexylthio, cyclohexylthio, thiophenol radicals; and/or $X_1$, $X_2$, $X_3$, $X_4$ and $X_5$ are selected independently from the hydrogen atom, the methoxy, ethoxy, n-propyloxy, isopropyloxy, n-butyloxy, tert-butyloxy, sec-butyloxy, n-hexyloxy, cyclohexyloxy, phenoxy, methylamine, dimethylamine, ethylamine, diethylamine, n-propylamine, dipropylamine, isopropylamine, diisopropylamine, n-butylamine, dibutylamine, tert-butylamine, n-hexylamine, dihexylamine, piperidine, pyrolidine, aniline, methylthio, ethylthio, n-propylthio, isopropylthio, n-butylthio, tert-butylthio, sec-butylthio, n-pentylthio, cyclopentylthio, n-hexylthio, cyclohexylthio, thiophenol, phenyl, benzyl, phenethyl, 2-methylphenyl, 3-m ethylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-(trifluoromethyl)phenyl, 3-(trifluoromethyl)phenyl, 4-(trifluoromethyl)phenyl, 2-(trifluoromethoxy)phenyl, 3-(trifluoromethoxy)phenyl, 4-(trifluoromethoxy)phenyl, 2,6-dimethylphenyl, 3,6-dimethylphenyl, 4,6-dimethylphenyl, 5,6-dimethylphenyl, 2,6-fluorophenyl, 3,6-fluorophenyl, 4,6-fluorophenyl, 5,6-fluorophenyl, 2,6-dichlorophenyl, 3,6-dichlorophenyl, 4,6-dichlorophenyl, 5,6-dichlorophenyl, 2,6-bromophenyl, 3,6-bromophenyl, 4,6-bromophenyl, 5,6-bromophenyl, 2,6-iodophenyl, 3,6-iodophenyl, 4,6-iodophenyl, 5,6-iodophenyl, iodo, bromo, chloro, fluoro, nitro, cyano, methyl, ethyl, n-propyl, isopropyl, cyclopropyl, n-butyl, isobutyl, tert-butyl, sec-butyl, cyclobutyl, pentyl, neopentyl, cyclopentyl, n-hexyl, cyclohexyl, pyridyl, furyl, thienyl radicals; and/or $R_1$ and $R_2$ can be selected independently from the hydrogen atom, the methyl, trifluoromethyl, ethyl, n-propyl, isopropyl, cyclopropyl, n-butyl, isobutyl, tert-butyl, sec-butyl, cyclobutyl, pentyl, neopentyl, cyclopentyl, n-hexyl, cyclohexyl radicals; $R_1$ and $R_2$ can also form, together and with the carbon atom to which they are bound, a ring of the cyclopropyl, cyclobutyl, cyclopentyl or cyclohexyl type; and/or $R_3$ and $R_4$ can be selected independently from the hydrogen atom, the iodo, bromo, chloro, fluoro, methyl, trifluoromethyl, ethyl, n-propyl, isopropyl, cyclopropyl, n-butyl, isobutyl, tert-butyl, sec-butyl, cyclobutyl, pentyl, neopentyl, cyclopentyl, n-hexyl, cyclohexyl, phenyl, benzyl, phenethyl radicals; $R_3$ and $R_4$ can also form, together and with the carbon atom to which they are bound, a ring of the cyclopropyl, cyclobutyl, cyclopentyl, or cyclohexyl type; and/or $Y_1$ can be selected from an oxygen, sulfur or selenium atom, or an —NR, in which case R can be selected from the hydrogen atom, the methyl, trifluoromethyl, ethyl, n-propyl, isopropyl, cyclopropyl, n-butyl, isobutyl, tert-butyl, sec-butyl, pentyl, neopentyl, n-hexyl, phenyl, benzyl, phenethyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-(trifluoromethyl)phenyl, 3-(trifluoromethyl)-phenyl, 4-(trifluoromethyl)phenyl, 2,6-dimethylphenyl, 3,6-dimethylphenyl, 4,6-dimethylphenyl, 5,6-dimethylphenyl, 2,6-fluorophenyl, 3,6-fluorophenyl, 4,6-fluorophenyl, 5,6-fluorophenyl, 2,6-dichlorophenyl, 3,6-dichlorophenyl, 4,6-dichlorophenyl, 5,6-dichlorophenyl, 2,6-bromophenyl, 3,6-bromophenyl, 4,6-bromophenyl, 5,6-bromophenyl, 2,6-iodophenyl, 3,6-iodophenyl, 4,6-iodophenyl, and 5,6-iodophenyl radicals, and/or $Y_2$ can be selected from an oxygen, sulfur or selenium atom, or a —$CR_5R_6$, in which case $R_5$ and $R_6$ can be selected independently from the hydrogen atom, the iodo, bromo, chloro, fluoro, methyl, trifluoromethyl, ethyl, n-propyl, isopropyl, cyclopropyl, n-butyl, isobutyl, tert-butyl, sec-butyl, cyclobutyl, pentyl, neopentyl, cyclopentyl, n-hexyl, cyclohexyl, phenyl, benzyl, phenethyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-(trifluoromethyl)phenyl, 3-(trifluoromethyl)phenyl, 4-(trifluoromethyl)phenyl, 2,6-dimethylphenyl, 3,6-dimethylphenyl, 4,6-dimethylphenyl, 5,6-dimethylphenyl, 2,6-fluorophenyl, 3,6-fluorophenyl, 4,6-fluorophenyl, 5,6-fluorophenyl, 2,6-dichlorophenyl, 3,6-dichlorophenyl, 4,6-dichlorophenyl, 5,6-dichlorophenyl, 2,6-bromophenyl, 3,6-bromophenyl, 4,6-bromophenyl, 5,6-bromophenyl, 2,6-iodophenyl, 3,6-iodophenyl, 4,6-iodophenyl, 5,6-iodophenyl, pyridyl, furyl, thienyl, methoxy, ethoxy, n-propyloxy, isopropyloxy, n-butyloxy, tert-butyloxy, sec-butyloxy, n-hexyloxy, cyclohexyloxy, phenoxy, methylamine, dimethylamine, ethylamine, diethylamine, n-propylamine, dipropylamine, isopropylamine, diisopropylamine, n-butylamine, dibutylamine, tert-butylamine, n-hexylamine, dihexylamine, piperidine, pyrolidine, aniline, methylthio, ethylthio, n-propylthio, isopropylthio, n-butylthio, tert-butylthio, sec-butylthio, n-pentylthio, cyclopentylthio, n-hexylthio, cyclohexylthio, and thiophenol radicals; $R_5$ and $R_6$ can also form, together and with the carbon atom to which they are bound, a ring of the cyclopropyl, cyclobutyl, cyclopentyl or cyclohexyl type; and/or W is a carboxyl radical, a derivative function (notably the methyl ester, ethyl ester, propyl ester, isobutyl ester, tert-butyl ester) or a bioisosteric group of the carboxylic acid function.

The invention relates more preferably to compounds of general formula (I) as previously defined and in which at least one of the following conditions is satisfied:

$Y_2$ is located meta or para of $Y_1$ and even more preferably $Y_2$ is located para of $Y_1$; and/or $X_3$ denotes a hydrogen atom and even more preferably $X_3$ and $X_2$ denote simultaneously a hydrogen atom or $X_3$ and $X_1$ denote simultaneously a hydrogen atom; and/or $X_4$ and $X_5$ denote independently a hydrogen atom, an alkyl radical having 1 to 6 carbon atoms, or a group —$OR''_a$ or —$SR''_a$ ($R''_a$ being an alkyl radical having 1 to 6 carbon atoms); and/or $R_1$, $R_2$, $R_3$, $R_4$ denote independently a hydrogen atom or a methyl, ethyl, propyl, butyl, isopropyl or tert-butyl radical; and/or $X_3$, $R_1$ and $R_2$ denote simultaneously hydrogen atoms; and/or $X_1$ and/or $X_2$ denote a ring with 5 to 14, preferably 5 to 10, atoms, unsubstituted or substituted with a —$CF_3$ group, and even more preferably a phenyl, furanyl or naphthalenyl radical, unsubstituted or substituted with a —$CF_3$ group; and/or G denotes a radical —$OR_a$ or —$SR_a$, with $R_a$ selected from an alkyl radical having 1 to 6 carbon atoms, a cyclohexyl or a phenyl radical; or alternatively G denotes a radical —$NR_aR_b$, $R_a$ and $R_b$ forming together, and with the nitrogen atom to which they are bound, a heterocycle with 3 to 8 atoms (notably, a piperidinyl radical); and/or G denotes a radical —$OR_a$ with $R_a$ selected from a methyl, ethyl, propyl, butyl, isopropyl or tert-butyl radical.

A first particular aspect of the invention relates to compounds of general formula (I) in which $Y_1$ denotes an oxygen or sulfur atom and simultaneously $Y_2$ denotes an oxygen atom, a sulfur atom or a group —$CR_5R_6$ in which $R_5$ and $R_6$, which may be identical or different, are selected from a hydrogen atom, an alkyl radical with 1 to 6 carbon atoms, an alkenyl or alkynyl radical with 2 to 6 carbon atoms, and a ring with 3 to 6 atoms, the ring preferably being phenyl.

A second particular aspect of the invention relates to compounds of general formula (I) in which $Y_1$ denotes an amino group —NH. According to this second particular aspect of the invention, $Y_2$ preferably represents an oxygen atom, a sulfur atom or a radical —$CR_5R_6$—, in which $R_5$ and $R_6$, which may be identical or different, are selected from a hydrogen atom, an alkyl radical with 1 to 6 carbon atoms, an alkenyl or alkynyl radical with 2 to 6 carbon atoms, and a ring with 3 to 6 atoms, the ring preferably being phenyl.

According to this first or second particular aspect of the invention, $X_1$ preferably denotes an unsubstituted phenyl radical or a phenyl radical substituted with a —$CF_3$ group, said group —$CF_3$ being preferably in para of the pyridinyl radical, and/or G denotes a group —$OCH_3$ or —$OC(CH_3)_3$. More specifically, $X_1$ advantageously denotes a phenyl radical substituted with a —$CF_3$ group in para of the pyridinyl radical, G denotes a group —$OCH_3$, and $X_2$ denotes a hydrogen atom. According to one embodiment of this first particular aspect of the invention, $X_1$ advantageously denotes an unsubstituted phenyl radical, G denotes a group —$OC(CH_3)_3$, and $X_2$ denotes a hydrogen atom. Whether they are compounds belonging to said first particular aspect of the invention or to said second particular aspect of the invention, advantageously $R_1$, $R_2$, $R_3$ and $R_4$ denote simultaneously hydrogen atoms.

Figure 7A:
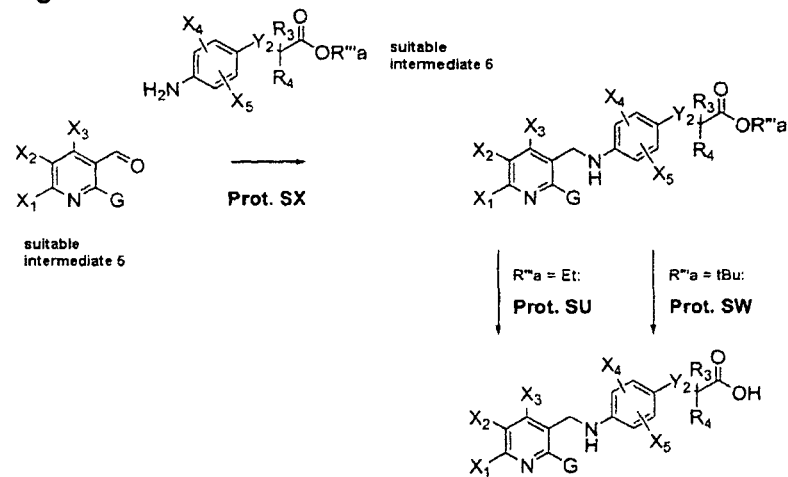
Figure 7B:
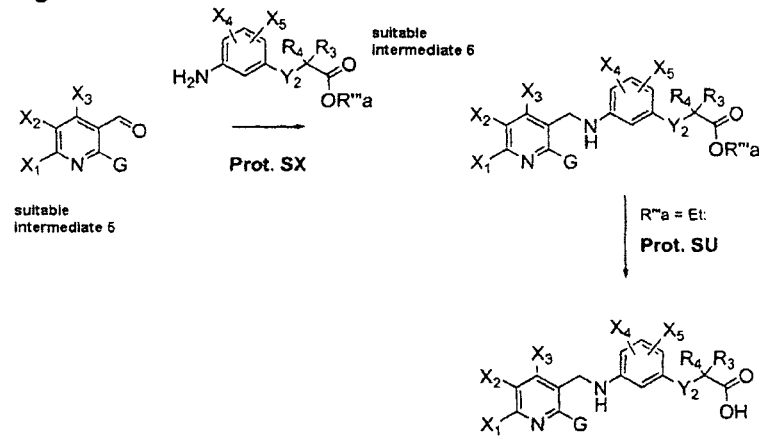
Figure 7C:
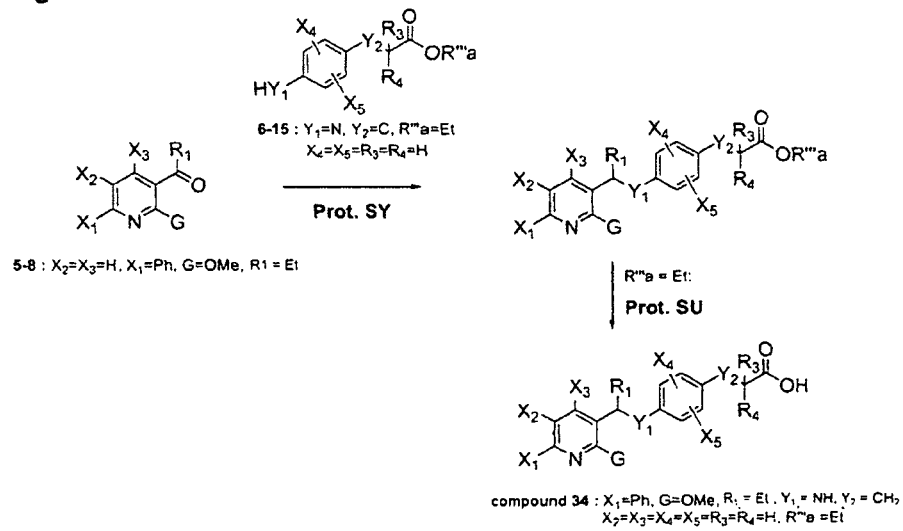
Figure 7D:
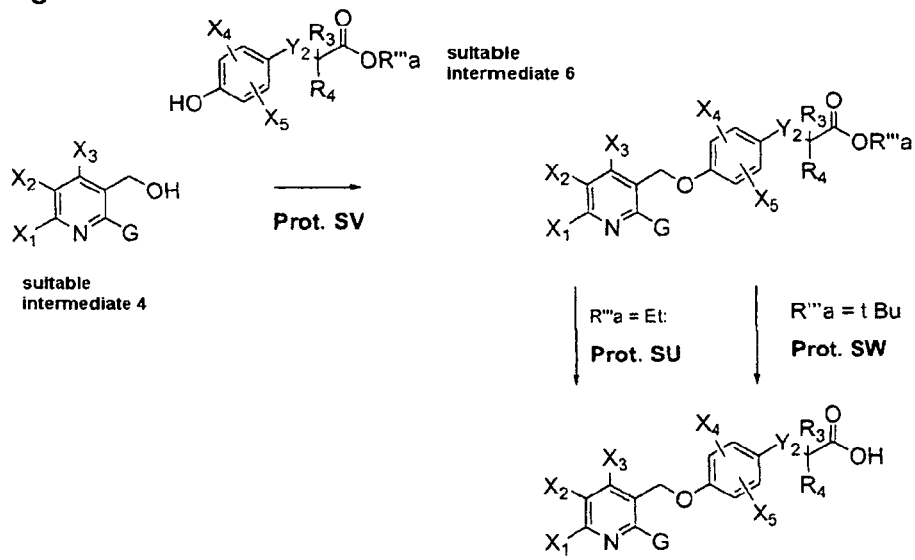
Figure 7E:
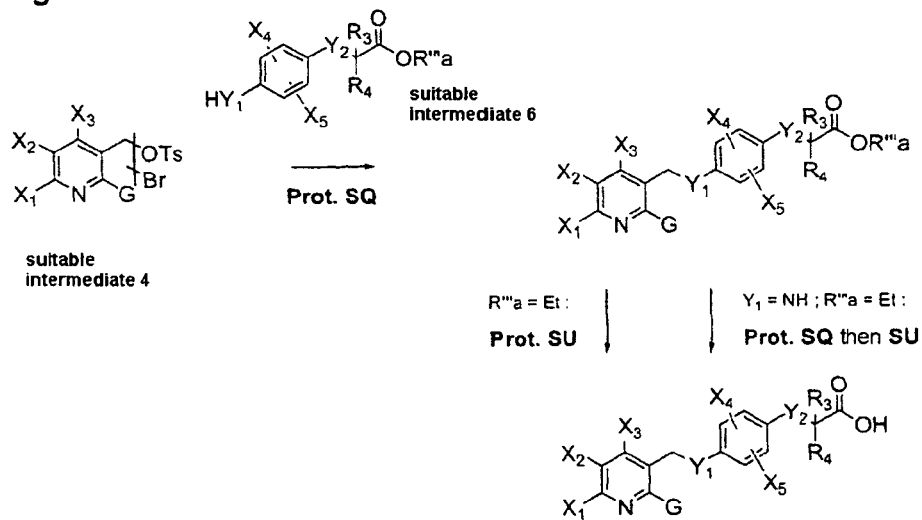
Figure 7F:
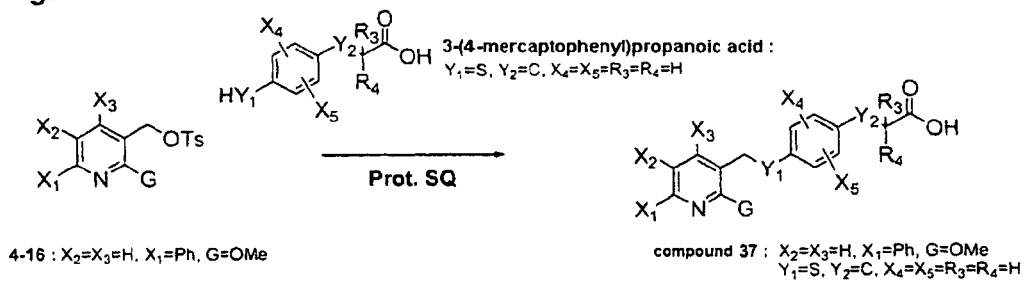
Figure 7G:
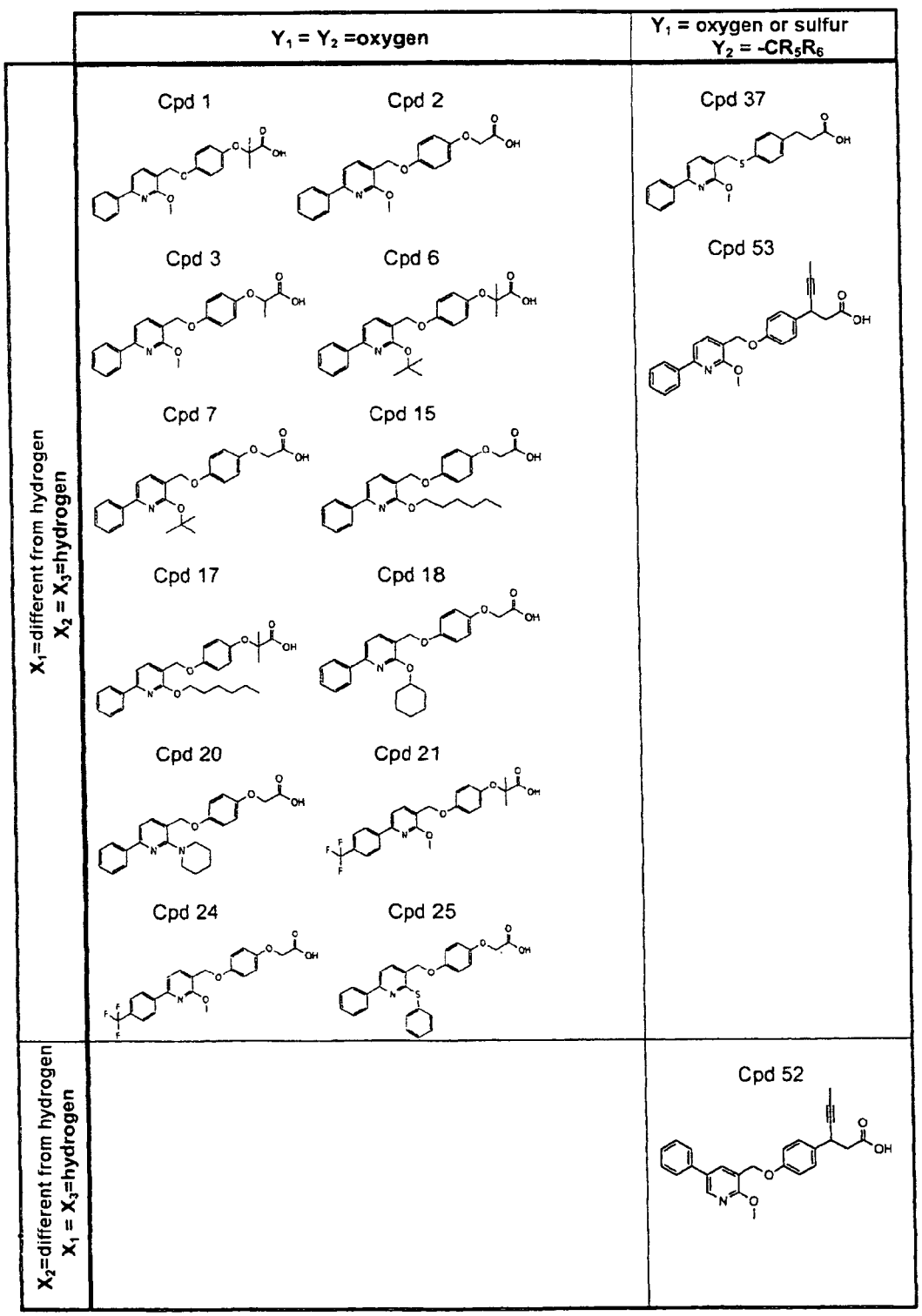
Figure 7H:
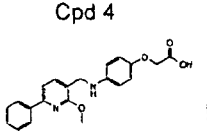
Figure 7H:
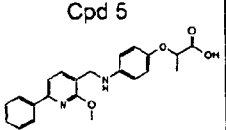
Figure 7H:
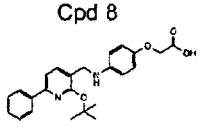
Figure 7H:
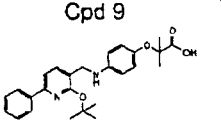
Figure 7H:
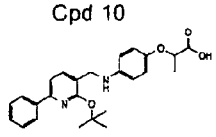
Figure 7H:
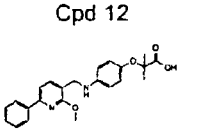
Figure 7H:
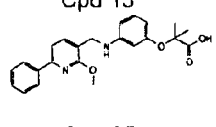
Figure 7H:
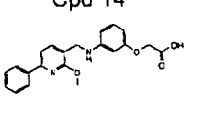
Figure 7H:
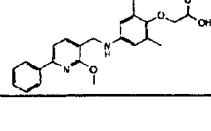
Figure 7H:
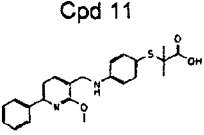
Figure 7H:
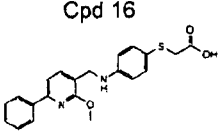
Figure 7H:
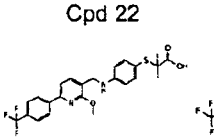
Figure 7H:
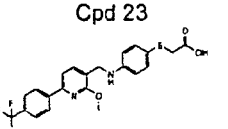
Figure 7H:
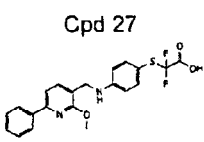
Figure 7H:
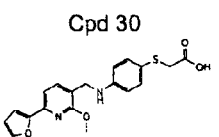
Figure 7H:
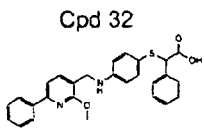
Figure 7H:
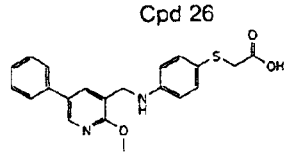
Figure 7H:
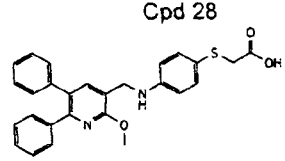
Figure 7H:
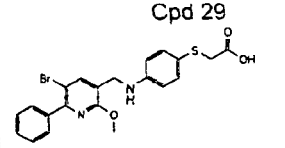
Figure 7I:
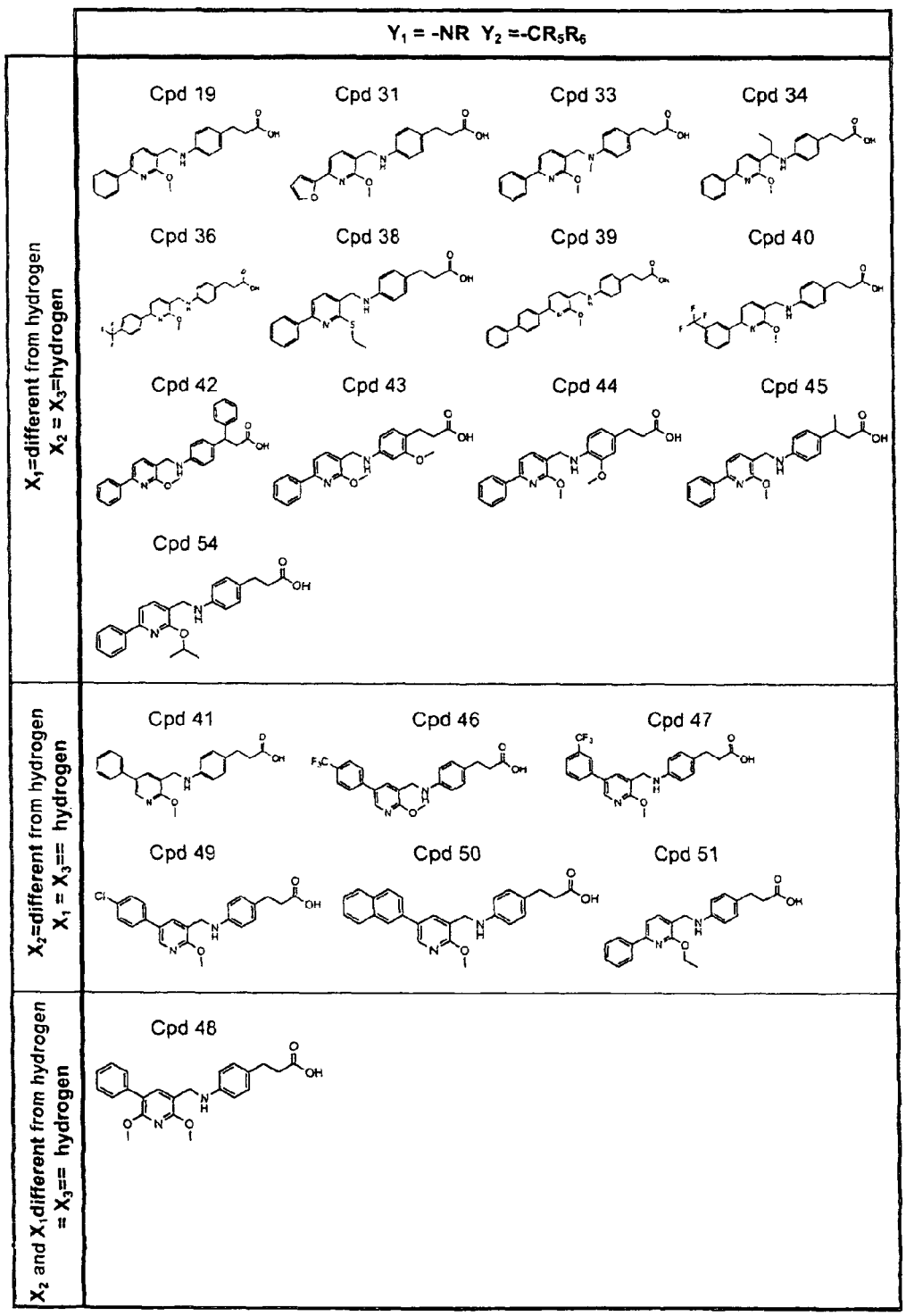

A third particular aspect of the invention relates to compounds of general formula (I) which
are identified and classified based on the structural characteristics as defined in FIGS. 7g, 7h and 7i; and/or
display the activities as established in Examples 8 to 12, and more specifically in Table 8-1 and FIGS. 8 to 12.

The present invention relates to compounds that are activators of PPARs. These compounds meet the pharmacological criteria stated in the literature for compounds of this kind, by measuring various parameters such as the properties of activating human PPARs in vitro and in cellular models, and antidiabetic or hypolipemic character in vivo in murine models. These results show that the compounds of general formula (I) having specific groups have properties that are superior and unexpected relative to documents of the prior art mentioning similar compounds, such as WO 03/084916, WO 08/152333, WO 05/041959, WO 08/066356, EP 1266888, and US 2005096336. For example, properties of activating PPARδ were confirmed in vivo and in vitro for Cpd 24 and Cpd 7 (see Table 8-1, Example 11, and FIG. 11), which form part of the same group of compounds according to the invention (see Cpd 2 in FIG. 7g, which was evaluated in Example 9). Moreover, properties of activating PPARγ were confirmed in vivo and in vitro for Cpd 19 and Cpd 36 (see Table 8-1, Example 12, and FIG. 12), which form part of the same group of compounds according to the invention (see FIG. 7i).

Preferably, the compounds according to the invention are selected from:

Cpd 1: 2-(4-((2-methoxy-6-phenylpyridin-3-yl)methoxy)phenoxy)-2-methyl-propanoic acid
Cpd 2: 2-(4-((2-methoxy-6-phenylpyridin-3-yl)methoxy)phenoxy)ethanoic acid
Cpd 3: 2-(4-((2-methoxy-6-phenylpyridin-3-yl)methoxy)phenoxy)propanoic acid
Cpd 4: 2-(4-(((2-methoxy-6-phenylpyridin-3yl)methyl)amino)phenoxy)ethanoic acid
Cpd 5: 2-(4-(((2-methoxy-6-phenylpyridin-3yl)methyl)amino)phenoxy)propanoic acid
Cpd 6: 2-(4-((2-tert-butyloxy-6-phenylpyridin-3-yl)methoxy)phenoxy)-2-methyl-propanoic acid
Cpd 7: 2-(4-(((2-tert-butyloxy-6-phenylpyridin-3-yl)methoxy)phenoxy)ethanoic acid
Cpd 8: 2-(4-((2-tert-butyloxy-6-phenylpyridin-3-yl)methyl)amino)phenoxy)ethanoic acid
Cpd 9: 2-(4-(((2-tert-butyloxy-6-phenylpyridin-3-yl)methyl)amino)phenoxy)-2-methyl-propanoic acid
Cpd 10: 2-(4-(((2-tert-butyloxy-6-phenylpyridin-3-yl)methyl)amino)phenoxy)propanoic acid
Cpd 11: 2-(4-(((2-methoxy-6-phenylpyridin-3-yl)methyl)amino)phenylthio)-2-methyl-propanoic acid
Cpd 12: 2-(4-(((2-methoxy-6-phenylpyridin-3-yl)methyl)amino)phenoxy)-2-methyl-propanoic acid
Cpd 13: 2-(3-(((2-methoxy-6-phenylpyridin-3-yl)methyl)amino)phenoxy)-2-methyl-propanoic acid
Cpd 14: 2-(3-(((2-methoxy-6-phenylpyridin-3-yl)methyl)amino)phenoxy)ethanoic acid
Cpd 15: 2-(4-((2-hexyloxy-6-phenylpyridin-3-yl)methoxy)phenoxy)ethanoic acid
Cpd 16: 2-(4-(((2-methoxy-6-phenylpyridin-3-yl)methyl)amino)phenylthio)ethanoic acid
Cpd 17: 2-(4-((2-hexyloxy-6-phenylpyridin-3-yl)methoxy)phenoxy)-2-methyl-propanoic acid
Cpd 18: 2-(4-((2-cyclohexyloxy-6-phenylpyridin-3-yl)methoxy)phenoxy)ethanoic acid
Cpd 19: 3-(4-(((2-methoxy-6-phenylpyridin-3-yl)methyl)amino)phenyl)propanoic acid
Cpd 20: 2-(4-((6-phenyl-2-(piperidin-1-yl)pyridin-3-yl)methoxy)phenoxy)ethanoic acid
Cpd 21: 2-(4-((2-methoxy-6-(4-(trifluoromethyl)phenyl)pyridin-3-yl)methoxy)-phenoxy)-2-methylpropanoic acid
Cpd 22: 2-(4-(((2-methoxy-6-(4-(trifluoromethyl)phenyl)pyridin-3-yl)methyl)amino)-phenylthio)-2-methylpropanoic acid
Cpd 23: 2-(4-(((2-methoxy-6-(4-(trifluoromethyl)phenyl)pyridin-3-yl)methyl)amino)-phenylthio)ethanoic acid
Cpd 24: 2-(4-((2-methoxy-6-(4-(trifluoromethyl)phenyl)pyridin-3-yl)methoxy)-phenoxy)ethanoic acid
Cpd 25: 2-(4-((2-phenylthio-6-(phenyl)pyridin-3-yl)methoxy)phenoxy)ethanoic acid
Cpd 26: 2-(4-(((2-methoxy-5-phenylpyridin-3-yl)methyl)amino)phenylthio)ethanoic acid
Cpd 27: 2-(4-(((2-methoxy-6-phenylpyridin-3-yl)methyl)amino)phenylthio)-2,2-difluoroethanoic acid
Cpd 28: 2-(4-(((2-methoxy-5,6-diphenylpyridin-3-yl)methyl)amino)phenylthio)ethanoic acid
Cpd 29: 2-(4-(((2-methoxy-5-bromo-6-phenylpyridin-3-yl)methyl)amino) phenylthio)-ethanoic acid
Cpd 30: 2-(4-(((2-methoxy-6-furylpyridin-3-yl)methyl)amino)phenylthio)ethanoic acid
Cpd 31: 3-(4-(((2-methoxy-6-furylpyridin-3-yl)methyl)amino)phenyl)propanoic acid
Cpd 32: 2-(4-(((2-methoxy-6-phenylpyridin-3-yl)methyl)amino)phenylthio)-2-phenyl-acid
Cpd 33: 3-(4-(((2-methoxy-6-phenylpyridin-3-yl)methyl)(methyl)amino)phenyl)-propanoic acid
Cpd 34: 3-(4-(1-((2-methoxy-6-phenylpyridin-3-yl)propyl)amino)phenyl)propanoic acid
Cpd 35: 2-(4-(((2-methoxy-6-phenylpyridin-3-yl)methyl)amino)-2,6-dimethyl-phenoxy)ethanoic acid
Cpd 36: 3-(4-(((2-methoxy-6-(4-(trifluoromethyl)phenyl)pyridin-3-yl)methyl)amino)-phenyl)propanoic acid
Cpd 37: 3-(4-((2-methoxy-6-phenylpyridin-3-yl)methylthio)phenyl)propanoic acid
Cpd 38: 3-(4-(((2-(ethylthio)-6-phenylpyridin-3-yl)methyl)amino)phenyl)propanoic acid
Cpd 39: 3-(4-(((2-methoxy-6-(parabiphenyl)pyridin-3-yl)methyl)amino)phenyl)-propanoic acid
Cpd 40: 3-(4-(((2-methoxy-6-(3-(trifluoromethyl)phenyl)pyridin-3-yl)methyl)amino)-phenyl)propanoic acid
Cpd 41: 3-(4-(((2-methoxy-5-phenylpyridin-3-yl)methyl)amino)phenyl)propanoic acid
Cpd 42: 3-(4-((2(-methoxy-6-phenylpyridin-3-yl)methyl)amino)phenyl)-3-phenyl-propanoic acid
Cpd 43: 3-(2-methoxy-4-(((2-methoxy-6-phenylpyridin-3-yl)methyl)amino)-phenyl)-propanoic acid
Cpd 44: 3-(3-methoxy-4-(((2-methoxy-6-phenylpyridin-3-yl)methyl)amino)-phenyl)-propanoic acid
Cpd 45: 3-(4-(((2-methoxy-6-phenylpyridin-3-yl)methyl)amino)phenyl)butanoic acid
Cpd 46: 3-(4-(((2-methoxy-5-(4-(trifluoromethyl)phenyl)pyridin-3-yl)methyl)amino)phenyl)propanoic acid
Cpd 47: 3-(4-(((2-methoxy-5-(3-(trifluoromethyl)phenyl)pyridin-3-yl)methyl)amino)-phenyl)propanoic acid
Cpd 48: 3-(4-(((2,6-dimethoxy-5-phenylpyridin-3-yl)methyl)amino)phenyl)propanoic acid
Cpd 49: 3-(4-(((5-(4-chlorophenyl)-2-methoxypyridin-3-yl)methyl)amino)phenyl)-propanoic acid
Cpd 50: 3-(4-(((2-methoxy-5-(naphthalen-2-yl)pyridin-3-yl)methyl)amino)phenyl)-propanoic acid
Cpd 51: 3-(4-(((2-ethoxy-6-phenylpyridin-3-yl)methyl)amino)phenyl)propanoic acid Cpd 52: 3-(4-((2-methoxy-5-phenylpyridin-3-yl)methoxy) phenyl)hex-4-ynoic acid
Cpd 53: 3-(4-((2-methoxy-6-phenylpyridin-3-yl)methoxy) phenyl)hex-4-ynoic acid
Cpd 54: 3-(4-(((2-isopropyloxy-6-phenylpyridin-3-yl)methyl)amino)phenyl)propanoic acid.

Even if the compounds according to the invention can be generated and purified according to methods and with compounds already known by a person skilled in the art and such as those described in the literature, the invention relates to methods of preparation of the compounds of general formula (I).

According to a first variant of the method of preparation (FIGS. 7a, 7b and 7c), the compounds of general formula (I) can be obtained by a series of reactions consisting of reacting intermediates of the phenol, thiophenol, or aniline type according to the invention with one of the intermediates of the pyridine 3-carboxaldehyde or ketone type according to the invention.

According to a second variant of the method of preparation (FIGS. 7d, 7e and 7f), the compounds of general formula (I) can be obtained by a series of reactions consisting of reacting intermediates of the phenol, thiophenol, or aniline type according to the invention with one of the intermediates of the 3-hydroxymethyl-, 3-halomethyl- or 3-arylsulfonylmethyl-pyridine type according to the invention.

The details of the general methods of synthesis and purification of the raw reaction products obtained are defined in Example 1. More particularly, Examples 1 to 7 show how different series of compounds according to the invention, and the corresponding reaction intermediates, can be synthesized and purified from compounds that are already known. A general scheme of synthesis of the compounds of general formula (I) is presented in FIG. 1 but a person skilled in the art will be able to synthesize said compounds with other methods and compounds already known, notably to obtain reaction intermediates and/or compounds with specific groups G, R, $R_1$-$R_6$, R'/''/'''/''''$_a$, R'/''/'''/''''$_b$, $X_1$-$X_6$ and/or $Y_1$, $Y_2$.

The functional groups optionally present in the reaction intermediates used in the methods can be protected, either permanently, or temporarily, by protective groups, which ensure unequivocal synthesis of the desired compounds. The reactions of protection and deprotection are carried out according to techniques well known by a person skilled in the art or such as those described in the literature, as in the book "Greene's Protective Groups in Organic Synthesis" (4th edition, 2007; edited by Wuts P G and Greene T W; published by John Wiley and Sons).

The compounds according to the invention can contain one or more asymmetric centers. The present invention includes stereoisomers (diastereoisomers, enantiomers), pure or mixed, as well as racemic mixtures and geometric isomers, or tautomers. When an enantiomerically pure (or enriched) mixture is desired, it can be obtained either by purification of the final product or of chiral intermediates, or by asymmetric synthesis according to methods known by a person skilled in the art (using for example chiral reactants and catalysts). Certain compounds according to the invention can have various stable tautomeric forms and all these forms and mixtures thereof are included in the invention. The techniques for obtaining and characterizing the stereoisomers, pure or mixed, as well as racemic mixtures and geometric isomers, or tautomers are described in the literature, such as in the book "Chirality in Drug Design and Development" (2004; edited by Reddy I K and Mihvar R; Published by CRC Press).

The compounds of general formula (I) can exist in the form of bases or of salts of addition to acids. These salts can be prepared, selected and used according to techniques well known by a person skilled in the art or as described in the literature such as in the book "Handbook of Pharmaceutical Salts: Properties, Selection, and Use" (2002; edited by Stahl P H and Wermuth G H; published by VHCA Switzerland and Wiley-VCH Germany). Notably, the present invention relates to the "pharmaceutically acceptable" salts of the compounds according to the invention. Generally, this term denotes salts of low toxicity or nontoxic obtained from bases or from acids, organic or inorganic.

These salts can be obtained during the stage of final purification of the compound according to the invention or by incorporation of the salt on the compound already purified. These salts can be prepared with pharmaceutically acceptable acids but the salts of other acids useful for purifying or isolating the compounds of general formula (I) also form part of the invention. In particular, when the compounds according to the invention are in the form of a salt, it is a salt of an alkali metal, in particular a salt of sodium or of potassium, or a salt of an alkaline-earth metal, in particular magnesium or calcium, or a salt with an organic amine, more particularly with an amino acid such as arginine or lysine.

More particularly, group W as described previously can have an acid character. The corresponding salts are selected from metal salts (for example, aluminum, zinc, chromium), alkaline salts (for example, lithium, sodium, potassium) or alkaline-earth (for example, calcium, magnesium). They can for example be organic salts such as nontoxic ammonium derivatives and amines: ammonium, quaternary ammonium (for example, tetramethylammonium, tetraethylammonium), alkylamines (for example, methylamine, dimethylamine, trimethylamine, triethylamine, ethylamine, etc.), hydroxyalkylamines (for example, 2-hydroxyethylamine, bis-(2-hydroxyethyl)amine, tri-(2-hydroxyethyl)amine, etc.), cycloalkylamines (for example, bicyclohexylamine, glucamine, etc.), pyridines and analogs (such as collidine, quinine, quinoline, etc.) of salts of amino acids with basic character (for example, lysine, arginine, etc.).

The pyridine nucleus, the groups G and/or $Y_1$ as described previously can have a basic character. The corresponding salts are selected advantageously from mineral acids (hydrochloric, hydrobromic, sulfuric, boric, nitric, phosphoric, etc.) or organic acids (for example, carboxylic or sulfonic acids such as formic, acetic, methylsulfonic, propionic, toluenesulfonic, valeric, oleic, palmitic, stearic, lactic, lauric, oxalic, citric, maleic, succinic, glycolic, tartaric acid, etc.) or salts obtained from amino acids with acid character such as glutamic acid.

Certain compounds according to the invention can be isolated in the form of zwitterions and each of these forms is included in the invention, as well as mixtures thereof. Certain compounds according to the invention and their salts can be stable in several solid forms. The present invention includes all solid forms of the compounds according to the invention, which includes the amorphous, polymorphic, mono- and poly-crystalline forms.

The compounds of general formula (I) can exist in the free form or in the solvated form, i.e. in the form of associations or combinations with one or more molecules of a solvent, for example with pharmaceutically acceptable solvents such as water (hydrates) or ethanol. The present invention also includes the prodrugs of the compounds according to the invention which, after administration to a subject, are converted to the compounds as described in the invention or to their metabolites having therapeutic activities comparable to the compounds according to the invention.

The compounds according to the invention labeled with one or more isotopes are also included in the invention: these compounds are structurally identical but differ in that at least one atom of the structure is replaced by an isotope (radioactive or not). Examples of isotopes that can be included in the structure of the compounds according to the invention can be selected from hydrogen, carbon, nitrogen, oxygen, sulfur such as $^2H$, $^3H$, $^{13}C$, $^{14}C$, $^{15}N$, $^{18}O$, $^{17}O$, $^{35}S$ respectively. The radioactive isotopes $^3H$ and $^{14}C$ are particularly preferred as they are easy to prepare and detect in studies of the bioavailability in vivo of the substances. The heavy isotopes (such as $^2H$) are particularly preferred as they are used as internal standards in analytical studies.

The present invention also relates to the compounds as described previously, as medicinal products. Notably the present invention relates to the use of a compound according to the invention in the manufacture of a medicinal product intended for the therapeutic and/or prophylactic treatment of diabetes, dyslipidemias, insulin resistance, pathologies associated with metabolic syndrome, atherosclerosis, and cardiovascular diseases (notably those associated with disorders of lipid and/or carbohydrate metabolism), obesity, hypertension and/or inflammatory diseases.

The present invention also relates to a pharmaceutical composition comprising, in a pharmaceutically acceptable carrier, at least one compound as described above, optionally in combination with one or more other therapeutic and/or cosmetic active principles. Advantageously it is a pharmaceutical composition for the therapeutic and/or prophylactic treatment of diabetes, dyslipidemias, insulin resistance, pathologies associated with metabolic syndrome, atherosclerosis, cardiovascular diseases, obesity, hypertension, inflammatory diseases, etc. The inflammatory pathologies denote asthma in particular. Preferably it is a pharmaceutical composition for preventing and/or treating cardiovascular risk factors associated with disorders of lipid and/or carbohydrate metabolism (hyperlipidemia, type 2 diabetes, obesity etc.) reducing the global risk, with PPAR activating compounds as described in the literature (Glide A J et al., 2006; Blaschke F et al., 2006).

Another object of the invention relates to a nutritional composition comprising at least one compound as described above.

Within the scope of the present invention and generally, "pharmaceutically acceptable carrier" means substances such as excipients, vehicles, adjuvants, buffers that are used conventionally, in combination with the active principle(s), for preparing a medicinal product. The choice of said carriers depends essentially on the route of administration envisaged.

Another object of the invention is the use of at least one compound as described previously for preparing pharmaceutical compositions intended for the therapeutic and/or prophylactic treatment of various pathologies, notably associated with disorders of metabolism, among which we may mention diabetes (in particular, type 2 diabetes), dyslipidemias, insulin resistance, pathologies associated with metabolic syndrome X, atherosclerosis, cardiovascular diseases, obesity, hypertension, inflammatory diseases.

As an example, the compounds according to the invention, like the insulin-secreting compounds and PPAR activating compounds currently marketed for the treatment of metabolic diseases, can advantageously be administered in combination with one or more other therapeutic and/or cosmetic agents, marketed or under development, such as:

antidiabetic drugs: insulin secretors (such as sulfonylureas and glinides etc.), inhibitors of alpha-glucosidase, PPARγ agonists (such as thiazolidinediones etc.), dual PPARα/PPARγ agonists, pan-PPAR agonists (compounds simultaneously activating the 3 PPAR isoforms), biguanides, inhibitors of Dipeptidyl Peptidase IV, agonists of Glucagon-Like Peptide-1 (such as exenatide), inhibitors of alpha-glucosidase, as well as insulin and insulin analogs;

hypolipemic and/or hypocholesterolemic molecules: fibrates (such as fenofibrate and gemfibrozil), inhibitors of hydroxylmethylglutaryl Coenzyme A reductase (such as statins), inhibitors of cholesterol absorption (such as ezetimibe and phytosterols), inhibitors of Cholesteryl Ester Transfer Protein, inhibitors of Acyl-CoA:Cholesterol O-Acyl Transferase (ACAT), inhibitors of Microsomal Triglyceride Transfer Protein, sequestering agents of biliary acids, vitamin E, polyunsaturated fatty acids, omega 3 fatty acids, derivatives of the nicotinic acid type (niacin);

antihypertensive agents and hypotensive agents: angiotensin-converting enzyme inhibitors (such as captopril and enalapril), antagonists of the angiotensin II receptor (such as losartan and irbesartan), beta-blockers (such as atenolol and propranolol), thiazide and nonthiazide diuretics, vasodilators, calcium channel blockers (such as nifedipine and verapamil);

antiplatelet agents (such as aspirin and clopidogrel);

anti-obesity agents: sibutramine, lipase inhibitors (orlistat), PPARδ agonists and antagonists, antagonists of the CB1 cannabinoid receptor, dopamine agonists, agonists of leptin receptors, serotonin reuptake inhibitors, beta-3 agonists, CCK-A agonists, NPY inhibitors, agonists of MC4 receptors, antagonists of melanin concentrating hormone receptors, antagonists of orexine, inhibitors of phosphodiesterases, inhibitors of 11-β-hydroxy steroid dehydrogenase, inhibitors of dipeptidyl peptidase IV, antagonists (or inverse agonists) of histamine H3, derivatives of ciliary neurotrophic factor, agonists of growth hormone secretagogue receptors, modulators of ghreline, inhibitors of diacyglycerol acyltransferase;

anti-inflammatory agents: corticoids (such as prednisone and hydrocortisone), nonsteroidal anti-inflammatories (derivatives of indole, of the arylcarboxylic group, derivatives of oxicam, or of the fenamate group), selective inhibitors of COX2 (such as celecoxib or rofecoxib);

antioxidants: for example probucol;

agents used in the treatment of heart failure: thiazide or nonthiazide diuretics, angiotensin converting enzyme inhibitors, digitalis glucosides, beta-blockers, phosphodiesterase inhibitors;

agents used for treating coronary insufficiency: beta-blockers, calcium channel blockers, NO donors, amiodarone, anti-asthmatic drugs: bronchodilators (beta 2 receptor agonists), corticoids, cromoglycate, leukotriene receptor antagonists;

corticoids used in the treatment of skin pathologies such as psoriasis and dermatitis;

vasodilators and/or anti-ischemic agents.

The invention also relates to a method of therapeutic and/or prophylactic treatment of diabetes, dyslipidemias, insulin resistance, pathologies associated with metabolic syndrome, atherosclerosis, cardiovascular diseases (notably those associated with disorders of lipid and/or carbohydrate metabolism), obesity, hypertension and/or inflammatory diseases, comprising the administration to a subject, notably human, of an effective amount of a compound or of a pharmaceutical composition as defined previously. In the sense of the invention the term "an effective amount" refers to an amount of the compound sufficient to produce the desired biological result, preferably nontoxic. In the sense of the invention the term "subject" means a mammal and more particularly a human.

The term "treatment" denotes therapeutic, symptomatic, and/or prophylactic treatment. The compounds of the invention can thus be used in subjects (in particular human) affected by a declared disease. The compounds of the invention can also be used for delaying or slowing the progression or preventing further progression of the disease, thus improving the condition of the subjects. The compounds of the invention can finally be administered to persons who are not ill, but who might normally develop the disease or who have a high risk of developing the disease.

According to another aspect of the invention, the compound of general formula (I), or one of its salts of addition to a pharmaceutically acceptable acid or one of its solvates or hydrates and another therapeutic agent can be administered simultaneously (in one and the same pharmaceutical form), separately (with administration, at the same time, of both compounds but each comprised in a separate pharmaceutical form) or spread over time (with the administration, at different times, of the two compounds, generally during a time interval not exceeding 24 hours).

The pharmaceutical compositions according to the invention advantageously comprise one or more pharmaceutically acceptable excipients or vehicles. We may mention for example saline, physiological, isotonic, buffered, etc. solutions, compatible with pharmaceutical use and known by a person skilled in the art. The compositions can contain one or more agents or vehicles selected from dispersants, solubilizers, stabilizers, preservatives, emulsifiers, antioxidants, emollients, hydrating agents, wetting agents, for improving the flavor, for regulating the hydration or pH, etc. Agents or vehicles usable in formulations (liquid and/or injectable and/or solid) are notably methylcellulose, hydroxymethylcellulose, carboxymethylcellulose, polysorbate 80, mannitol, gelatin, lactose, certain vegetable or animal oils, acacia, dextrose, sucrose, gelatin, agar, stearic acid, liposomes, etc. The compositions can be formulated in the form of injectable suspensions, gels, oils, tablets, suppositories, powders, hard capsules, soft capsules, aerosols, etc., optionally by means of galenic forms or devices providing prolonged and/or delayed release. For this type of formulation, an agent, such as cellulose, carbonates or starches, is advantageously used. As an example, a unit dosage form of a compound according to the invention in the form of a tablet can comprise the following components: mannitol, croscarmellose sodium, maize starch, hydroxypropyl-methylcellulose, magnesium stearate.

The compounds or compositions according to the invention can be administered in various ways and in various forms. Thus, they can for example be administered systemically, by the oral, parenteral, topical, ocular, rectal, perlingual route, by inhalation or by injection, for example by the intravenous, intramuscular, subcutaneous, transdermal, intraarterial route, etc. For injections, the compounds are generally packaged in the form of liquid suspensions, which can be injected by means of syringes or by perfusion. For the oral route, the composition can be in the form of tablets, capsules, coated tablets, syrups, suspensions, solutions, powders, granules, emulsions, suspensions of microspheres or nanospheres or of lipid or polymer vesicles for controlled release. For the parenteral route, the composition can be in the form of solutions or suspensions for perfusion or for injection.

Of course, a person skilled in the art will take care to select the possible compound or compounds to be added to these compositions in such a way that the advantageous properties intrinsically attaching to the present invention are not or substantially not altered by the addition envisaged, as is also explained in the literature, for example in the book "Pharmaceutical Dosage Forms and Drug Delivery" (2007; edited by Mahato R; published by CRC Press).

It is understood that the flow rate and/or the dose injected can be adapted by a person skilled in the art in relation to the patient's sex, age and weight, the pathology, the method of administration, or any concomitant treatments. Typically, the compounds are administered at doses that can vary between 1 µg and 2 g per administration, preferably from 0.1 mg to 1 g per administration. The administrations can be daily or even repeated several times per day, if necessary. Furthermore, the compositions according to the invention can additionally comprise other agents or active principles. The compounds are used at a concentration generally between 0.001% and 10 wt. %, preferably between 0.01% and 1 wt. %, relative to the weight of the composition.

ABBREVIATIONS

ACO: Acyl-CoenzymeA oxidase
ApoCIII: Apolipoprotein CIII
Cpd: Compound
CPT1b: Carnitine Palmitoyl Transferase 1b
Ctrl: Control
Et: Ethyl
Stg.: Stage
Ex. Example
G: Group in general formula (I)
HDL-cholesterol: High Density Lipoprotein cholesterol
HOMA: Homeostatic Model Assessment
Int.: Intermediate
mpk: mg/kg/day
OMe: O-Methyl
OtBu: O-Tert-butyl
PDK4: Pyruvate Dehydrogenase Kinase, isoform 4
Ph: Phenyl
Prot. Protocol
PPAR: Peroxisome proliferator-activated receptor
R, $R_1$-$R_6$, R/'/"/"'$_a$, R/'/"/"'$_b$ Groups in general formula (I)
SEt: S-Ethyl
tBu: Tert-butyl
TG: Triglycerides
UCP2: Uncoupling Protein 2
$X_1$-$X_6$: Groups in general formula (I)
$Y_1$, $Y_2$: Groups in general formula (I)

Statistical Analyses

The statistical analyses of the various pharmacological experiments consist of a Student t-test. The results are expressed relative to the control group according to the p-value: $p<0.05$ (marked *); $p<0.01$ (marked ); $p<0.001$ (marked *).

LEGENDS OF THE FIGURES

FIG. 1—General Scheme for Synthesis of the Compounds According to the Invention

Except for specific compounds as stated in Examples 1 to 7, the intermediates generated in Example 2 (FIG. 2) were used for synthesizing the intermediates in Example 3 (FIG. 3). The latter were used for synthesizing the intermediates in Example 4 (FIG. 4), which were then used for synthesizing the intermediates in Example 5 (FIG. 5). The intermediates in Example 6 (FIG. 6) were generated separately. As described in Example 7 (FIG. 7), the compounds according to the invention were synthesized using either the intermediates from Example 4 and Example 6 or the intermediates from Example 5 and Example 6.

FIG. 2—Intermediates of the 2-oxo-1.2-dihydropyridine Type

Figure 2A:
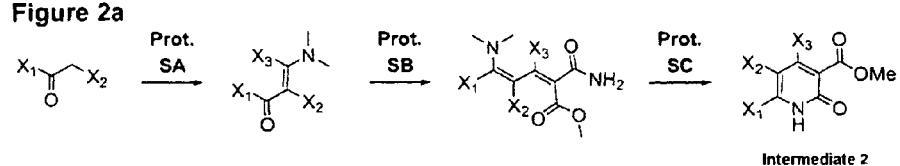
Figure 2B:
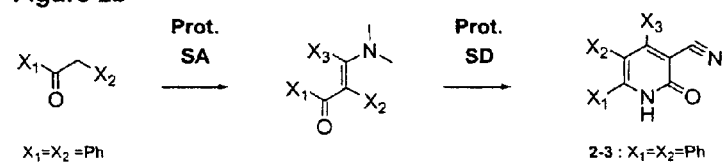
Figure 2C:
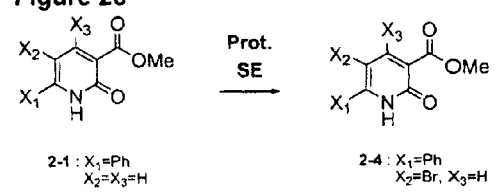
Figure 2D:
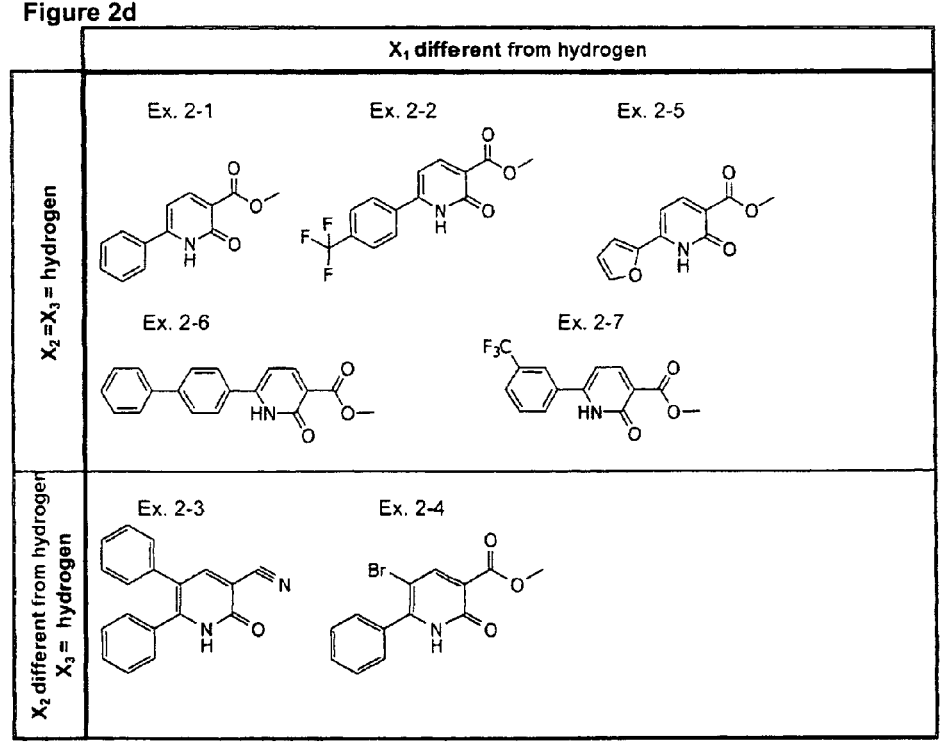

Reaction scheme for synthesis of the intermediates in Example 2: Ex. 2-1, 2-2 and 2-5 to 2-7 (FIG. 2a); 2-3 (FIG. 2b); 2-4 (FIG. 2c). These intermediates can be classified according to their groups $X_1$, $X_2$ and $X_3$ (FIG. 2d).

FIG. 3—Intermediates of the alkoxy, alkylthio-, alkylamino-, halo-pyridine Type

Reaction scheme for synthesis of the intermediates in Example 3: Ex. 3-1 to 3-4, 3-7, 3-9, 3-12, 3-13, 3-15, 3-16, 3-24 and 3-25 (FIG. 3a); 3-10, 3-11, 3-3-23 (FIG. 3b); 3-5, 3-6, 3-8 and 3-14 (FIG. 3c). These intermediates can be classified according to their groups $X_1$, $X_2$ and $X_3$ (FIGS. 3d and 3e).

FIG. 4—Intermediates of the 3-hydroxymethyl-, 3-halomethyl- and 3-arylsulfonylmethyl-pyridine type Reaction scheme for synthesis of the intermediates in Example 4: Ex. 4-1 to 4-10, 4-12, 4-13, 4.14, 4-17 to 4-23 (FIG. 4a); 4-15 (FIG. 4b); 4-11 (FIG. 4c); 4-16 (FIG. 4d). These intermediates can be classified according to their groups $X_1$, $X_2$ and $X_3$ (FIGS. 4e and 4f).

FIG. 5—Intermediates of the Pyridine 3-carboxaldehyde and Ketone Type

Reaction scheme for synthesis of the intermediates in Example 5: Ex. 5-1, 5-3, 5-4, 5-6 to 5-18 (FIG. 5a); 5-2 (FIG. 5b); 5-5 (FIG. 5c). These intermediates can be classified according to their groups $X_1$, $X_2$ and $X_3$ (FIGS. 5d and 5e).

FIG. 6—Intermediates of the Phenol, Thiophenol and Aniline Type

Reaction scheme for synthesis of the intermediates in Example 6: Ex. 6-1 to 6-6, 6-11 to 6-13, and 6-20 (FIG. 6a); 6-10, 6-14, 6-16 to 6-19 (FIG. 6b); 6-7 to 6-9 (FIG. 6c); 6-15 (FIG. 6d); 6-21 to 6-24 (FIG. 6e). These intermediates can be classified according to their groups $Y_1$ and $Y_2$ (FIGS. 6f and 6g).

FIG. 7—Compounds According to the Invention

Reaction scheme for synthesis of the compounds according to the invention: Cpd 4, Cpd 8-12, Cpd 16, Cpd 19, Cpd 22, Cpd 23, Cpd 26-32, Cpd 35, Cpd 36, Cpd 38-51, and Cpd 54 (FIG. 7a); Cpd 13 and Cpd 14 (FIG. 7b); Cpd 34 (FIG. 7c); Cpd 2, Cpd 6, Cpd 7, Cpd 15, Cpd 17, Cpd 18, Cpd 20, Cpd 21, Cpd 24, Cpd 25, Cpd 52, Cpd 53 (FIG. 7d); Cpd 1, Cpd 3, Cpd 5, Cpd 33 (FIG. 7e); Cpd 37 (FIG. 7f). The compounds according to the invention can be classified according to their groups $X_1$, $X_2$, $X_3$, $Y_1$ and $Y_2$ (FIGS. 7g, 7h, and 7i).

FIG. 8—Antidiabetic Character of the Compounds According to the Invention

The effect of Cpd 24 was evaluated in vivo in the db/db mouse. The plasma levels of glucose (FIG. 8a), of insulin (FIG. 8b), and the HOMA index (FIG. 8c) were measured after 8 days of treatment with Cpd 24 administered at 30 mpk in the db/db mouse. The difference measured provides evidence of the effect of Cpd 24 on the parameters of insulin resistance. A decrease in the HOMA index, calculated on the basis of these plasma parameters, also reflects an improvement in sensitivity to insulin.

Figure 8A:
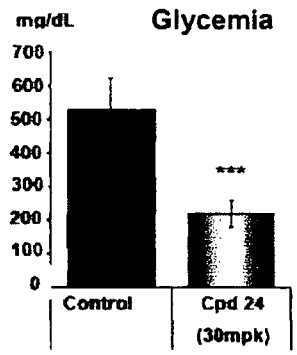
Figure 8B:
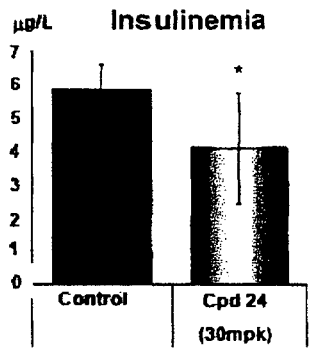
Figure 8C:
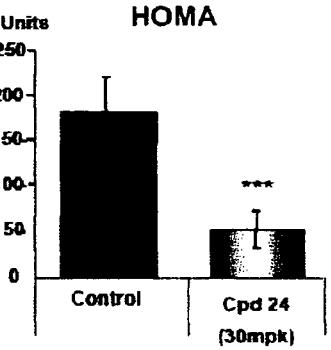
Figure 8D:
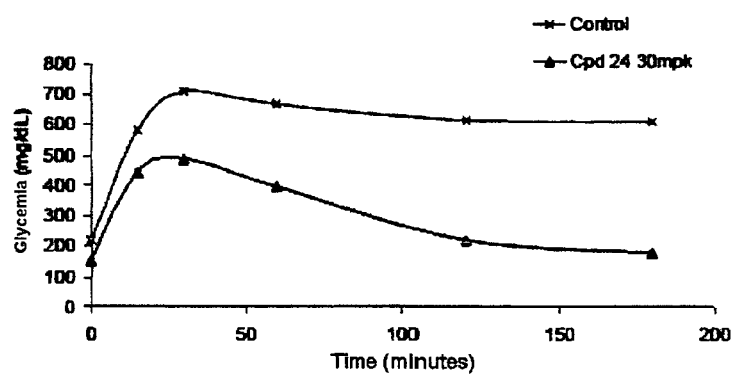
Figure 8E:
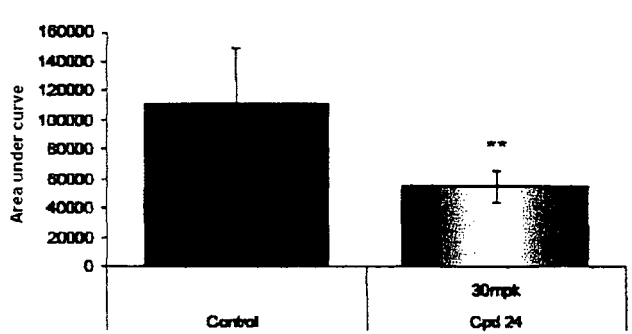

The effect of Cpd 24 was also evaluated by measuring glucose tolerance. Glycemia was measured in the db/db mouse treated with Cpd 24, administered at 30 mpk for 9 days, after oral administration of a single dose of glucose (day 0), to obtain the kinetic curves of glycemia (FIG. 8d; the areas under the curves of the glucose tolerance test are shown in FIG. 8e). The corrective action of Cpd 24 on insulin resistance is reflected in an improvement in glucose tolerance. The levels are compared with those obtained in control animals (untreated).

FIG. 9—Hypolipemic Properties and Stimulating Effect on the Synthesis of HDL-Cholesterol of the Compounds According to the Invention The plasma levels of total cholesterol (FIG. 9a) and of HDL-cholesterol (FIG. 9b) were measured in the ApoE2/E2 dyslipidemic mouse after 7 days of treatment with Cpd 2 or Cpd 4 by the oral route, administered at 10 and 100 mpk. These parameters are compared with those obtained in control animals (untreated): the difference measured provides evidence of the hypolipemic effect of the compounds according to the invention.

Figure 9A:
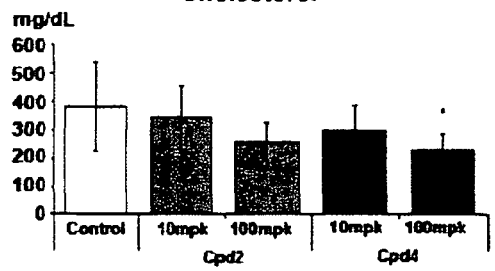
Figure 9B:
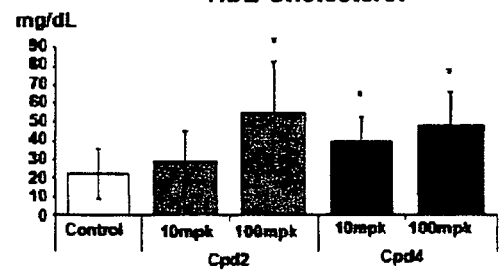
Figure 9C:
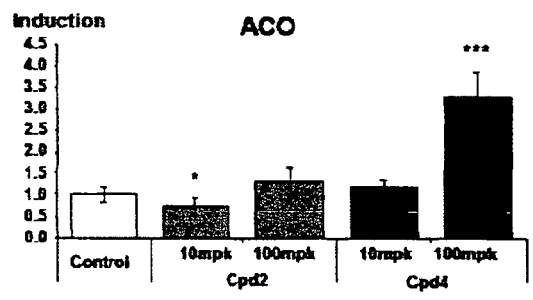
Figure 9D:
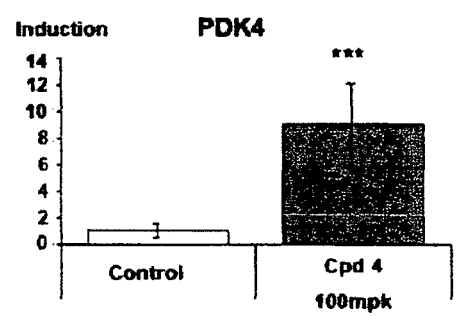
Figure 9E:
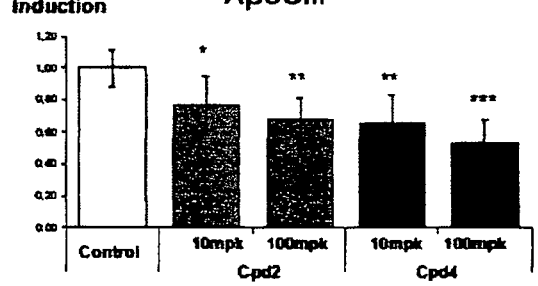

The effect of Cpd 2 and Cpd 4 was also evaluated in hepatic tissue of the ApoE2/E2 mouse by measuring the expression of genes involved in lipid and/or carbohydrate metabolism such as ACO (FIG. 9c), PDK4 (FIG. 9d) and Apo CIII (FIG. 9e). The levels of expression of each gene are normal relative to the level of expression of the 36B4 reference gene. These parameters are compared with those obtained in control animals (untreated): the induction factor, i.e. ratio of the relative signal (induced by the compound according to the invention) to the mean of the relative values of the control group, is then calculated. The higher this factor, the greater the gene expression activating character of the compound. The final result is given as the mean of the induction values in each experimental group.

FIG. 10—Hypolipemic Properties of the Compounds According to the Invention

The plasma levels of total cholesterol (FIG. 10a) and of free fatty acids (FIG. 10b) were measured in the E2/E2 dyslipidemic mouse after 7 days of oral treatment with Cpd 19, administered at 100 mpk. These parameters are compared with those obtained with control animals (untreated): the difference measured provides evidence of the hypolipemic effect of the compounds according to the invention.

FIG. 11—PPARδ Activating Properties of the Compounds According to the Invention

The stimulating effects of the compounds according to the invention on lipid and carbohydrate metabolism and on energy expenditure in skeletal muscle were evaluated by measuring the expression of PDK4 (FIG. 11a), CPT1b (FIG. 11b), and UCP2 (FIG. 11c) in murine myocytes treated for 24 hours with Cpd 7 or Cpd 24 at different concentrations (0.1, 1, 10 µM and 0.2, 2 and 20 µM respectively). Expression of these genes in this cell type is a direct consequence of activation of PPARδ by the compounds according to the invention. As expression of the genes is increased, the effect of the compound according to the invention as activator of PPARδ and therefore the stimulating effect on metabolism in muscle cells increase. The levels of expression shown were normalized relative to the level of expression of the 36B4 reference gene.

FIG. 12—PPARγ Activating Properties of the Compounds According to the Invention

The stimulating effects of Cpd 19, Cpd 24 and Cpd36 on adipogenesis were evaluated by measuring the accumulation of TG (FIGS. 12a and 12c) and the secretion of adiponectin (FIGS. 12b and 12d) in a model in vitro of murine pre-adipocytes. After 9 days of treatment with the compounds in dose response from 30 nM to 30 µM, the levels were compared with those measured in untreated cells: as the concentrations of TG and of adiponectin are increased, the greater the adipogenic and therefore PPARγ activating character of the compounds. The activity of the compounds according to the invention is also compared with the effects of a reference PPARγ agonist molecule (rosiglitazone). As the accumulation of triglycerides and secretion of adiponectin are increased, the greater the effect of the compound according to the invention as activator of PPARγ and therefore stimulator of metabolism in adipocyte cells.

EXAMPLES

Example 1

General Protocols

The compounds of the invention are prepared according to the general methods and general protocols of synthesis SA to SY given below. The compounds according to the invention and the corresponding reaction intermediates were characterized structurally by $^1$H NMR (300 MHz; CDCl$_3$, CDCl$_3$+ D$_2$O, or DMSO-d$_6$, the last mentioned condition notably for the compounds according to the invention; δ in ppm).

Protocol SA:

The appropriate ketone (acetophenone for Ex. 2-1; 4-trifluoroacetophenone for Ex. 2-2; 2-phenylacetophenone for Ex. 2-3; 2-acetylfuran for Ex. 2-5; para-acetylbiphenyl for Example 2-6; 3-trifluoromethylacetophenone 2.7) is dissolved in dimethyl acetal of N,N-dimethylformamide (1.2 to 1.5 eq.). The reaction mixture is stirred under reflux. The estimated reaction time varies between 24 and 48 hours. Satisfactory results were obtained in 24 hours.

Protocol SB:

Prop-2-en-1-one from the preceding stage (see Examples 2-1, 2-2, 2-5, 2-6, and 2-7) is dissolved in methanol (0.3 to 1.5 mol/L). The reaction mixture is stirred under reflux. The estimated reaction time varies between 18 and 48 hours. Satisfactory results were obtained in 18 hours.

Protocol SC:

The methyl ester from the preceding stage (see Examples 2-1, 2-2, 2-5, 2-6, 2-7) is dissolved in toluene (0.15 to 0.5 mol/L), then acetic acid (1 to 1.5 eq.) is added. The mixture is stirred under reflux. The estimated reaction time varies between 12 and 48 hours. Satisfactory results were obtained in 18 hours. After it reaches room temperature, the reaction mixture is cooled to 0° C. and the precipitate formed is filtered and then washed with acetone.

Protocol SD:

The aminopropenone from the preceding stage, cyanoacetamide (1.1 eq.) and methanol (2 eq.) are dissolved in N,N-dimethylformamide (0.3 mol/L). This solution is added to a suspension of NaH (2 eq.) in N,N-dimethylformamide (3 mol/L). The whole is stirred at 95° C. for 18 hours.

Protocol SE:

The pyridinone from the preceding stage (Ex. 3-9 for Ex. 3-10; Ex. 3-19 for Ex. 3-20) and N-bromosuccinimide (1 to 1.1 eq.) are dissolved in N,N-dimethylformamide (0.1 to 0.4 mol/L). The reaction mixture is stirred under reflux. For a yield of at least 30-80%, the estimated reaction time varies between 4 and 16 hours. Satisfactory results were obtained in 4 hours. After returning to room temperature, the precipitate formed is drained and washed with water and/or heptane.

Protocol SF:

2-oxo-1,2-dihydropyridine (Ex. 2-1 for Ex. 3-1 to 3-4, 3-24, 3-25; Ex. 2-2 for Ex. 3-7; Ex. 2-4 for Ex. 3-12; Ex. 2-5 for Ex. 3-13; Ex. 2-6 for Ex. 3-15; Ex. 2-7 for Ex. 3-16; 3-18; 2-hydroxynicotinic acid for Ex. 3-9) is dissolved in toluene (0.06 to 0.4 mol/L), then silver oxide (1 to 1.2 eq.) and the halogenated derivative (for example, 1 to 1.2 eq.; methyl iodide for Ex. 3-1, 3-7, 3-9, 3-12, 3-15, 3-16, 3-19, 5-5; ethyl iodide for Ex. 3-24; isopropyl iodide for Ex. 3-25; tert-butyl bromide for Ex. 3-2; 1-iodohexane for Ex. 3-3; iodocyclohexane for Ex. 3-4) are added successively. The reaction mixture is stirred under reflux at a temperature which varies between 50° C. and 70° C., and the salts are removed by filtration. For a yield of at least 40-80% after purification according to purification protocol PA, the estimated reaction time varies between 1 and 48 hours. Satisfactory results were obtained in 16 hours. The reaction can advantageously be carried out under reflux of acetonitrile to improve the solubility of the reaction mixture.

Protocol SG:

2-oxo-1,2-dihydropyridine (Ex. 2-1 for Ex. 3-5) is dissolved in phosphoryl trichloride (10 eq.) in the presence of a catalytic amount of N,N-dimethylformamide. The reaction mixture is stirred under reflux for 16 hours.

Protocol SH:

Halopyridine (Ex. 3-5 for Ex. 3-8, 3-14) is dissolved in acetonitrile (0.06 to 0.4 mol/L) and potassium carbonate (2 to 3 eq.) is added. The thiol (for example 1.2 to 3 eq.; thiophenol for Ex. 3-8; ethanethiol for Ex. 3-14) is added dropwise and the whole is stirred under reflux. For a yield of at least 80%, the estimated reaction time varies between 18 and 48 hours. Satisfactory results were obtained in 18 hours.

Protocol SI:

The intermediate (0.15 mol/L; Ex. 3-1 for Ex. 3-11; Ex. 3-10 for Ex. 3-17, Ex. 3-18, Ex. 3-22, Ex. 3-23; Ex. 3-20 for 3-21), potassium carbonate (3 eq.) and water (11 eq.) are dissolved in N,N-dimethylformamide under inert atmosphere. Palladium acetate (0.1 eq.) is added, then the solution of boronic acid (phenylboronic acid for Ex. 3-11 and 3-21; 4-trifluoromethyllboronic acid for Ex. 3-17; 3-trifluoromethylphenylboronic acid for Ex. 3-18; 4-chlorophenylboronic acid for Ex. 3-22; naphthalen-2-ylboronic acid for Ex. 3-23) in N,N-dimethylformamide (1.5 eq., 1 mol/L) is added dropwise. The estimated reaction time varies between 16 and 48 hours. The reaction mixture is stirred under inert atmosphere at room temperature.

Protocol SJ:

The ester of 2-alkoxy-1,2-dihydropyridine (Ex. 3-1 for Ex. 4-1; Ex. 3-2 for Ex. 4-2; Ex. 3-3 for Ex. 4-3; Ex. 3-4 for Ex. 4-4; Ex. 3-6 for Ex. 4-5; Ex. 3-7 for Ex. 4-6; Ex. 3-8 for Ex. 4-7; Ex. 3-11 for Ex. 4-8; Ex. 3-12 for Ex. 4-9; Ex. 3-13 for Ex. 4-10; Ex. 3-14 for Ex. 4-12; Ex. 3- for Ex. 4-; Ex. 3-15 for Ex. 4-13; Ex. 3-16 for Ex. 4-14; Ex. 3-17 for Ex. 4-17; Ex. 3-18 for Ex. 4-18; Ex. 3-21 for Ex. 4-19; Ex. 3-22 for Ex. 4-20; Ex. 3-23 for Ex. 4-21; Ex. 3-24 for Ex. 4-22; Ex. 3-25 for Ex. 4-23) is dissolved in tetrahydrofuran (0.05 to 1.1 mol/L) and the solution is cooled to 0° C. Aluminum lithium hydride (1 to 2 eq.) is added in portions and the whole is stirred at room temperature. The reaction mixture is treated with water (2.5 eq.), 15% soda (17 eq.), then diluted with water (7.5 eq.) and stirring is continued. The estimated reaction time varies between 1 and 24 hours.

Protocol SK:

Pyridine carboxaldehyde (Ex. 5-1 for Ex. 4-11) is dissolved in tetrahydrofuran (0.45 mol/L) and the solution is cooled to −78° C. A solution of ethylmagnesium bromide (3.4 eq., 2M) is added dropwise. The whole is stirred for 18 hours at room temperature.

Protocol SL:

Hydroxymethylpyridine (Ex. 4-1 for Ex. 4-15) and triethylamine (1.5 eq.) are dissolved in tetrahydrofuran (1 mol/L), then paratoluene sulfonyl chloride (1.5 eq.) is added. The whole is stirred under reflux for 16 hours.

Protocol SM:

Hydroxymethylpyridine (Ex. 4-1 for Ex. 4-16) is dissolved in dichloromethane (0.2 mol/L), then the solution is cooled to 0° C. Phosphorus tribromide (1 eq.) is added. The whole is stirred at 0° C. After 0.2 hours, the reaction mixture is poured onto crushed ice and then extracted with dichloromethane.

Protocol SN:

Hydroxymethylpyridine (Ex. 4-1 for Ex. 5-1; Ex. 4-6 for Ex. 5-3; Ex. 4-8 for Ex. 5-4; Ex. 4-9 for Ex. 5-6; Ex. 4-10 for Ex. 5-7; Ex. 4-11 for Ex. 5-8; Ex. 4-12 for Ex. 5-9; Ex. 4-13 for Ex. 5-10; Ex. 4-14 for Ex. 5-11; Ex. 4.17 for Ex. 5-12; Ex. 4-18 for Ex. 5-13; Ex. 4-19 for Ex. 5-14; Ex. 4-20 for Ex. 5-15; Ex. 4-21 for Ex. 5-16; Ex. 4-22 for Ex. 5-17; Ex. 4-23 for Ex. 5-18) is dissolved in dichloromethane (0.06 to 0.5 mol/L), then pyridinium chlorochromate (PCC; 1.2 to 2 eq.) is added. The reaction mixture is stirred at room temperature. The estimated reaction time varies between 2 and 48 hours.

Protocol SO:

Hydroxymethylpyridine (Ex. 4-2 for Ex. 5-2) is dissolved in dichloromethane (1.5 mol/L), then the solution is cooled to 0° C. Dess-Martin reagent (1.1 eq.) is added dropwise and the whole is stirred at 0° C.

Protocol SP:

1,2-Dihydropyridine-carbonitrile (Ex. 2-3 for Ex. 5-5) is dissolved in formic acid (1.1 mol/L) and Raney nickel (50 M.%) is added (1.5 eq.). The whole is stirred for 2 hours under reflux before returning to room temperature.

Protocol SQ:

Phenol (4-benzyloxyphenol for Ex. 6-1 to 6-5; 3-nitrophenol for Ex. 6-12, 6-13; 4-nitrophenol for Ex. 6-6, 6-11; 4-nitro-2,6-dimethylphenol for Ex. 6-20), thiophenol (4-aminothiophenol for Ex. 6-10, 6-14, 6-16 to 6-19), aniline (4-hydroxy-10-tertiobutoxycarbonylaniline for Ex. 6-7, 6-8, 6-9), or acid (2,6-dimethoxynicotinic acid for Ex. 3-19) is dissolved in the appropriate solvent (0.2 to 1.2 mol/L) then the halogenated derivative or the tosylate (1.2 to 3 eq.; bromodifluoroethyl acetate for Ex. 6-18; methyl iodide for Ex. 3-19; ethyl 2-bromopropanoate for Ex. 6-3.6-7; ethyl bromoisobutyrate for Ex. 6-1, 6-9, 6-10; tert-butyl bromoisobutyrate for Ex. 6-2, 6-5, 6-11, 6-12, 6-16; tert-butyl bromoacetate for Ex. 6-13, 6-14; bromoethyl acetate for Ex. 6-4, 6-8, 6-17, 6-20; tert-butyl bromoacetate for Ex. 6-6; 2-bromo-2-phenylethyl acetate for Ex. 6-19) and potassium carbonate (2.5 to 6 eq.) are added. The reaction mixture is stirred vigorously at a suitable temperature and, if necessary, under reflux of acetonitrile, N,N-dimethylformamide, acetonitrile of an acetonitrile/N,N-dimethylformamide mixture (6%), or in the presence of tetrabutylammonium bromide (0.3 eq.). For the compounds according to the invention, the phenol, the thiophenol, the aniline, or the acid was prepared in Example 6, and the halogenated derivative or the tosylate was prepared in Example 4 or 5. The estimated reaction time varies between 0.1 and 48 hours and the reaction mixture is cooled to room temperature.

Protocol SR:

The ester from the preceding stage is dissolved in the appropriate solvent (0.3 to 1.2 mol/L of methanol, ethanol, dichloromethane, or methanol/dichloromethane mixture 1/1 or 2/1), then palladium on charcoal (10 wt. %) is added in catalytic amounts. The whole is stirred, under a hydrogen atmosphere at a suitable pressure. The estimated reaction time varies between 4 and 120 hours of stirring at room temperature. The catalyst is removed by filtration.

Protocol SS:

The protected amine (3-(4-aminophenyl)propanoic acid for Ex. 6-15) is dissolved in ethanol (0.3 to 0.6 mol/L), then an ethanolic solution of hydrochloric acid is added (2 eq.). The reaction mixture is stirred at room temperature. The estimated reaction time varies between 2 and 16 hours.

Protocol ST:

Triethylphosphonacetate (0.5 mol, L) is added dropwise to a suspension of sodium hydride (1 eq.) in tetrahydrofuran at 0° C. After stirring for 30 min at room temperature, the carbonylated derivative (1 eq.; 4-nitrobenzophenone for Ex. 6-21; 4-nitroacetophenone for Ex. 6-24; 3-methoxy-4-nitrobenzaldehyde for Ex. 6-23; 2-methoxy-4-nitrobenzaldehyde for Ex. 6-22) is added and the reaction mixture is refluxed for 16 hours.

Protocol SU:

The ester from the preceding stage is dissolved in ethanol (0.03 to 1 mol/L), then a 1N or 2N solution of soda (1 to 84 eq., preferably from 2 to 20 eq.) is added. The whole is stirred at room temperature. For a yield of at least 30-85% after purification according to one of the alternatives presented in example 2, the estimated reaction time varies between 1 and 96 hours. Satisfactory results were obtained in 16 hours. If necessary, tetrahydrofuran can advantageously be added to improve the solubility of the reaction mixture.

Protocol SV:

The phenol (0.1 to 0.9 mol/L) and triphenylphosphine (1.05 eq.) are dissolved in tetrahydrofuran under inert atmosphere. Diisopropyl azodicarboxylate (1.05 eq.) and alcohol solution in tetrahydrofuran (1.05 eq., 0.1 to 0.9 mol/L) are added dropwise successively. The whole is stirred at room temperature. For a yield of at least 30-80%, the estimated reaction time varies between 16 and 72 hours. Satisfactory results were obtained in 16 hours. If necessary, dichloromethane can be used advantageously to improve the solubility of the reaction mixture; use of a microwave (for example 0.1 hour at 50° C.) can greatly improve the performance of the reaction.

Protocol SW:

The tert-butyl ester from the preceding stage is dissolved in dichloromethane (0.08 to 0.2 mol/L), and trifluoroacetic acid (10 to 72 eq., preferably 10 eq.) is added. Stirring is maintained at room temperature. The reaction is carried out at room temperature with stirring. The precipitate is filtered, taken up in water (0.2 L/mol) and treated with 2N soda solution (3 eq.) for 0.5 hours. The whole is acidified with a 1N solution of citric acid, stirring vigorously, and then filtered. For a yield of at least 30-80%, the estimated reaction time varies between 16 and 24 hours. Satisfactory results were obtained in 16 hours. The reaction mixture can be treated, while stirring vigorously, with a 10% solution of potassium carbonate for 0.5 hours (pH=8-9) before being acidified.

Protocol SX:

The aldehyde and the aniline (1 to 1.5 eq.) are dissolved in dichloromethane (0.1 to 0.4 mo/L), under inert atmosphere. The reaction mixture is stirred at room temperature for 1 hour. Sodium triacetoxyborohydride (1.2 to 1.5 eq.) is added in portions, then the whole is stirred vigorously at room temperature. When the aniline required is available in its hydrochloride form, it is first salted-out by basic treatment. For a yield of at least 40-85% after purification according to one of the alternatives presented in example 2, the estimated reaction time varies between 2.5 and 72 hours. Satisfactory results were obtained in 16 hours. Working with an anhydrous solvent and/or in the presence of a molecular sieve 3A can greatly improve the performance of the reaction.

Protocol SY:

The ketone and the aniline (1.2 eq.) are dissolved in toluene (0.03 mo/L), in the presence of paratoluenesulfonic acid (1 eq.) and molecular sieve 3 Å, in a Dean-Stark apparatus. The reaction mixture is stirred at 110° C. for 16 hours. After cooling, the insoluble matter is filtered and the filtrate is concentrated under reduced pressure. The evaporation residue is taken up in dichloromethane. Sodium triacetoxyborohydride (1.5 eq.) is added in portions, then the whole is stirred vigorously at room temperature in the presence of molecular sieve 3 Å for 48 hours. When the aniline required is available in its hydrochloride form, it is first salted-out by basic treatment.

The raw reaction products obtained can be purified following one or more of the general purification protocols PA to PE. For this purpose, conventional preliminary steps of hydrolysis (without dilution, or with dilution, for example, with ethyl acetate) or washing (neutral, acid or basic, for example with water, saturated solution of sodium chloride, 1N solution of citric acid, saturated solution of ammonium chloride, 10% solution of potassium carbonate, 1N solution of sodium hydroxide), then extraction of the reaction mixture with a suitable solvent (diethyl ether or dichloromethane, for example), drying of the organic phases (for example, over magnesium sulfate), concentration (notably of the reaction mixture, notably by evaporation under reduced pressure), and/or removal of insoluble matter can advantageously be carried out (the salts are removed by filtration, for example).

In the case of protocol PA, silica gel flash chromatography (40-63 µm) was performed with various conditions of elution (mobile phase), as summarized in Table 1-1.

In the case of protocol PB, silica gel chromatography is performed by preparative HPLC (lichrospher, Merck; RP18 12 µm 100A, column: 25*250 mm; Stg. 2 for Cpd 5, Cpd 13, Cpd 14, Cpd 17, Cpd 18, Cpd 20, Cpd 23, Cpd 52; Stg. 1 for Cpd 37).

In the case of protocol PC, precipitation is performed in a mixture of solvents which are selected from the usual solvents by a person skilled in the art such as notably dichloromethane, heptane, cyclohexane, toluene, for example dichloromethane/heptane 4/6 (Stg. 1 for Ex. 2-1, 2-2, 2-6; Stg. 2 for Cpd 12, Cpd 16, Cpd 19, Cpd 22, Cpd 27, Cpd 30, Cpd 31, Cpd 49; Stg. 3 for Cpd 46, Cpd 47, Cpd 48, Cpd 51, Cpd 53), dichloromethane/toluene 4/6 (Stg. 2 for Ex. 2-5), or dichloromethane/cyclohexane 4/6 (Stg. 3 for Cpd 45, Cpd 54).

In the case of protocol PD, (re)crystallization is performed in a solvent selected from the usual solvents by a person skilled in the art such as isopropanol (Stg. 2 for Cpd 9), ethanol (Stg. 2 for Ex. 2-1, Cpd 25), acetone (Stg. 2 for Ex. 2-2), methanol (Stg. 2 for Ex. 2-6, Cpd 3, Cpd 6, Cpd 7), petroleum ether (Stg. 1 for Ex. 6-2, 6-13), dichloromethane, heptane (Stg. 1 for Ex. 6-11, 6-20), cyclohexane (Stg. 1 for Ex. 6-6, 6-7, 6-9), or a mixture for example with dichloromethane/heptane (Cpd 15, Cpd 21, Cpd 24, Cpd 28, Cpd 29, Cpd 32, Cpd 42, Cpd 43, Cpd 44)

In the case of protocol PE, the product that precipitates is filtered at the end of the reaction. The estimated reaction time varies between 12 and 24 hours. After the reaction mixture has cooled to 0° C., hydrolysis or acid hydrolysis of the reaction mixture (Stg. 3 for Ex. 2-1, 2.2, 2-5 to 2-7, Stg. 3 for Ex. 2-3, 2-4; Cpd 2, Cpd 4, Cpd 26; Stg. 1 for Ex. 3-20) or a sequence of basic hydrolysis/filtration/trituration of the filter cake in acid aqueous medium (for example in ethanol; Stg. 2 for Ex. 6-7, 6-8, 6-9; Stg. 1 for Ex. 6-15) is performed.

Example 2

Synthesis of the Intermediates of the 2-Oxo-1,2-Dihydropyridine Type According to the Invention The synthesis of these intermediates (FIG. 2) requires 2 or 3 stages, as summarized in Table 2-1:

TABLE 1-1

| Mobile Phase | Examples |
|---|---|
| dichloromethane/ methanol or (9/1 to 98/2) | Stg. 1 for Ex. 2-5, 4-1, 4-7, 5-5; Cpd 33; Stg. 2 for Cpd 1, Cpd 8, Cpd 10, Cpd 11, Cpd 15, Cpd 21, Cpd 22, Cpd 24, Cpd 28, Cpd 29, Cpd 32-36, Cpd 38-48, Cpd 50, Cpd 51, Cpd 53, Cpd 54 Stg. 3 for 2-7, |
| dichloromethane/ cyclohexane (8/2) | Stg. 2 for 5-5 |
| dichloromethane/ethyl acetate or cyclohexane/ethyl acetate (95/5 or 98/2) | Stg. 1 for Ex. 3-3, 3-4, 3-12, 5-1, 5-12, 5-13, 5-15, 5-175-6, 5-18, and 6-5; Cpd 3, Cpd 6, Cpd 7, Cpd 13-18, Cpd 32, Cpd 34, Cpd 36, Cpd 38, Cpd 42, Cpd 43, Cpd 46-48 Stg. 2 for Cpd 15 |
| dichloromethane/ethyl acetate or cyclohexane/ ethyl acetate (9/1 or 85/15) | Stg. 1 for Ex. 2-3, 3-2, 3-5, 3-7, 3-8, 3-11, 3-13, 3-14, 3.22, 3-23, 3-24, 4-5, 4-9, 4-11, 4-21, 5-2, 5-4, 5-7, 5-8, 5-9, 5-14, 5-16, 6-1, 6-3, 6-4, 6-12, 6-14, 6-18, 6-22; Cpd 1, Cpd 2, Cpd 4, Cpd 5, Cpd 8, Cpd 9, Cpd 10, Cpd 11, Cpd 12, Cpd 16, Cpd 19-26, Cpd 30, Cpd 31, Cpd 39, Cpd 40, Cpd 41, Cpd 44, Cpd 45, Cpd 49-54 Stg. 2 for Ex. 6-3, 6-12 |
| dichloromethane/ethyl acetate or cyclohexane/ ethyl acetate (7/3, 8/2, or 6/4) | Stg. 1 for Ex. 3-1, 3-9, 3-15, 3-16, 3-19, 3-25, 4-2, 4-6, 4-10, 4-12, 4-13, 4.14, 4-15, 4-19, 5-3, 5-10, 5-11, 6-10, 6-11, 6-13, 6-16, 6-17, 6-19, 6-21, 6-23, 6-24; Cpd 27, Cpd 28, Cpd 29, Cpd 35; Stg. 2 for Ex. 6-5 6-21, 6-24 |

TABLE 2-1

| Ex. | No. and type of Stage (Protocol) | Details |
| --- | --- | --- |
| 2-1 | 1: Preparation of 3-dimethylamino-1-phenylprop-2-en-1-one (Protocol SA and PC) | Yield: 92%. Appearance: yellow solid. $^1$H NMR: 2.93-3.14 (m, 6H); 5.73 (d, 1H, J = 12.4 Hz); 7.38-7.49 (m, 3H); 7.82 (d, 1H, J = 12.4 Hz); 7.89 (d, 2H, J = 7.9 Hz). |
|  | 2: Preparation of methyl 2-carbamoyl-5-dimethylamino-5-phenylpentane-2,4-dienoate (Protocol SB and PD) | Yield: 63% |
|  | 3: Obtaining methyl 2-oxo-6-phenyl-1,2-dihydropyridine-3-carboxylate (Protocol SC and PE) | Yield: 66%. Appearance: yellow solid. $^1$H NMR: 3.77 (s, 3H); 6.79 (d, 1H, J = 7.6 Hz); 7.51-7.53 (m, 3H); 7.82-7.85 (m, 2H); 8.14 (d, 1H, J = 7.6 Hz). |
| 2-2 | 1: Preparation of 3-dimethylamino-1-(4-trifluoromethylphenyl)prop-2-en-1-one (Protocol SA and PC) | Yield: 81%. Appearance: yellow solid. $^1$H NMR: 2.94 (s, 3H); 3.17 (s, 3H); 5.69 (d, 1H, J = 12.3 Hz); 7.66 (d, 2H, J = 8.2 Hz); 7.83 (d, 1H, J = 12.3 Hz); 7.97 (d, 2H, J = 8.2 Hz). |
|  | 2: Preparation of methyl 2-carbamoyl-5-dimethylamino-5-(4-trifluoromethylphenyl)pentane-2,4-dienoate (Protocol SB and PD) | Yield: 37%. Appearance: yellow solid. |
|  | 3: Obtaining methyl 2-oxo-6-(4-(trifluoromethyl)phenyl)-1,2-dihydropyridine-3-carboxylate (Protocol SC and PE) | Yield: 38%. Appearance: yellow solid. $^1$H NMR: 4.02 (s, 3H); 7.35 (d, 1H, J = 8.3 Hz); 7.75 (d, 2H, J = 8.3 Hz); 8.17 (d, 2H, J = 8.3 Hz); 8.31 (d, 1H, J = 8.3 Hz). |
| 2-3 | 1: Preparation of 1,2-diphenylprop-2-en-1-one (Protocol SA and PE) | Yield: 68%. Appearance: yellow solid. $^1$H NMR: 2.72 (s, 6H); 7.09-7.46 (m, 11H). |
|  | 2: Obtaining 2-oxo-5,6-diphenyl-1,2-dihydropyridine-3-carbonitrile (Protocol SD and PE) | Yield: 73%. Appearance: white solid. $^1$H NMR: 7.03-7.06 (m, 2H); 7.19-7.40 (m, 8H); 8.23 (s, 1H); 12.76 (s, 1H). |
| 2-4 | Methyl 5-bromo-2-oxo-6-phenyl-1,2-dihydropyridine-3-carboxylate (Protocol SE and PE) | Yield: 37%. Appearance: white solid. $^1$H NMR: 3.79 (s, 3H); 7.50-7.57 (m, 5H); 8.23 (s, 1H); 12.49 (s(I), 1H). |
| 2.5 | 1: Preparation of 3-dimethylamino-1-furyl-prop-2-en-1-one (Protocol SA and PA) | Yield: 69%. Appearance: yellow solid. $^1$H NMR: 2.93 (s, 3H); 3.14 (s, 3H); 5.68 (d, 1H, J = 12.6 Hz); 6.48 (m, 1H); 7.06 (m, 1H); 7.49 (m, 1H); 7.80 (d, 1H, J = 12.6 Hz). |
|  | 2: Preparation of methyl 2-carbamoyl-5-dimethylamino-5-furyl-pentane-2,4-dienoate (Protocol SB and PC) | Yield: 24%. Appearance: yellow solid. |
|  | 3: Obtaining methyl 6-furyl-2-oxo-1,2-dihydropyridine-3-carboxylate (Protocol SC and PE) | Yield: 47%. Appearance: yellow solid. $^1$H NMR: 3.98 (s, 3H); 6.59-6.60 (m, 1H); 7.15 (m, 1H); 7.40 (m, 1H); 7.59 (d, 1H, J = 1.1 Hz); 8.26 (d, 1H, J = 7.9 Hz). |
| 2-6 | 1: Preparation of 3-dimethylamino-1-parabiphenylprop-2-en-1-one (Protocol SA and PC) | Yield: 40%. Appearance: yellow solid. $^1$H NMR: 2.97-3.16 (m, 6H); 5.79 (d, 1H, J = 12.3 Hz); 7.35-7.40 (m, 1H); 7.46-7.49 (m, 2H); 7.63-7.67 (m, 4H); 7.85 (d, 1H, J = 12.3 Hz); 7.89 (d, 2H, J = 8.2 Hz). |
|  | 2: Preparation of methyl 2-carbamoyl-5-dimethylamino-5-(parabiphenyl)pentane-2,4-dienoate (Protocol SB and PD) | Yield: 43%. Appearance: yellow solid. |
|  | 3: Obtaining methyl 2-oxo-6-parabiphenyl-1,2-dihydropyridine-3-carboxylate. (Protocol SC and PE) | Yield: 59%. Appearance: yellow solid. $^1$H NMR: 4.00 (s, 3H); 7.17-7.24 (m, 1H); 7.38-7.42 (m, 1H); 7.46-7.51 (m, 2H); 7.66 (d, 2H, J = 7.3 Hz); 7.74 (d, 2H, J = 8.5 Hz); 8.09 (d, 2H, J = 8.5 Hz); 8.29 (d, 1H, J = 7.9 Hz). |
| 2-7 | 1: Preparation of 3-dimethylamino-1-(3-trifluoromethylphenyl)prop-2-en-1-one (Protocol SA and PA) | Yield: 53%. Appearance: brown oil. $^1$H NMR: 2.88 (s, 3H); 3.10 (s, 3H); 5.64 (d, 1H, J = 12.3 Hz); 7.48 (m, 1H); 7.64 (d, 1H, J = 7.9 Hz); 7.80 (d, 1H, J = 12.3 Hz); 8.03 (d, 1H, J = 7.6 Hz); 8.11 (s, 1H). |
|  | 2: Preparation of methyl 2-carbamoyl-5-dimethylamino-5-(3-trifluoromethylphenyl)-pentane-2,4-dienoate (Protocol SB and PA) | Yield: 23%. Appearance: yellow solid. |
|  | 3: Obtaining methyl 2-oxo-6-(4-(trifluoromethyl)phenyl)-1,2-dihydropyridine-3-carboxylate (Protocol SC and PE) | Yield: 58%. Appearance: beige solid. $^1$H NMR: 4.02 (s, 3H); 7.36 (d, 1H, J = 8.2 Hz); 7.62 (t, 1H, J = 7.9 Hz); 7.73 (d, 1H, J = 7.9 Hz); 8.25 (d, 1H, J = 7.9 Hz); 8.30-8.32 (m, 2H). |

Example 3

Figure 3A:
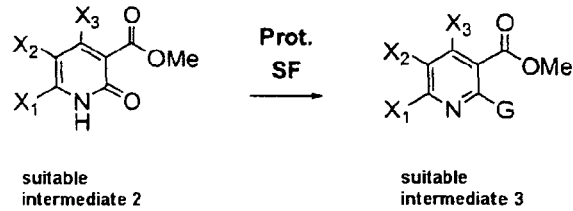
Figure 3B:
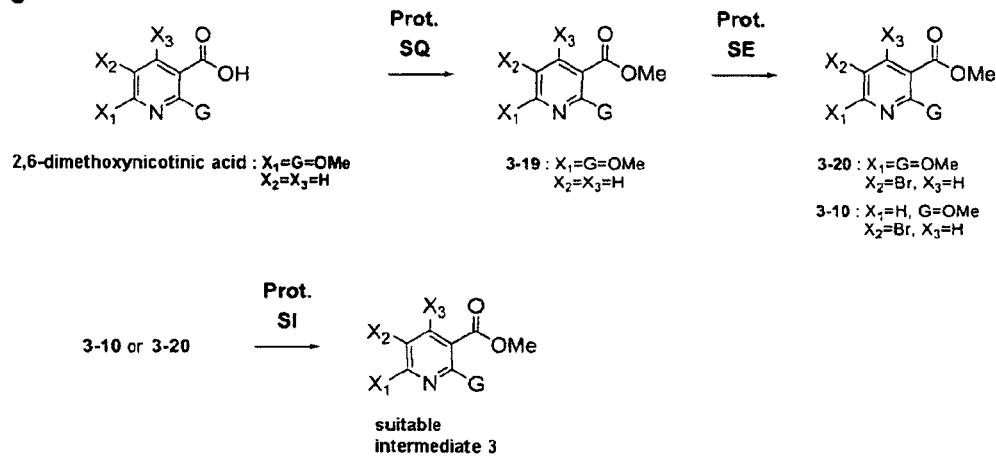
Figure 3C:
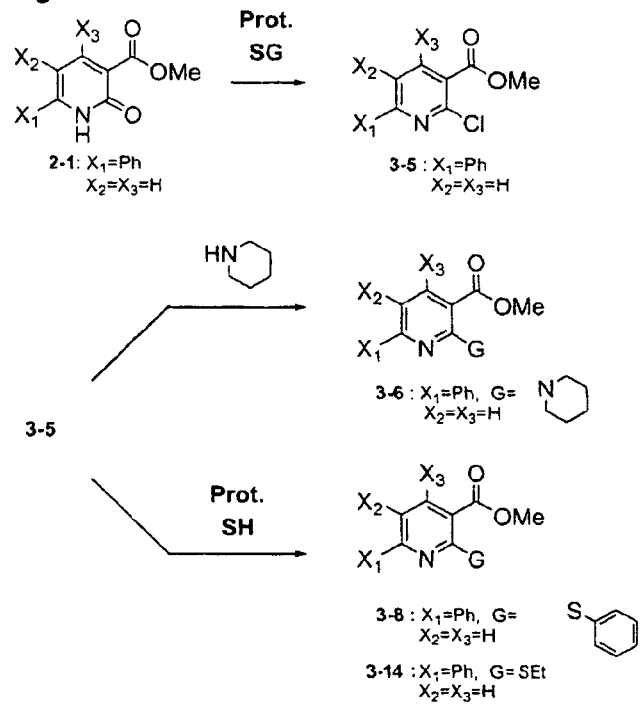
Figure 3D:
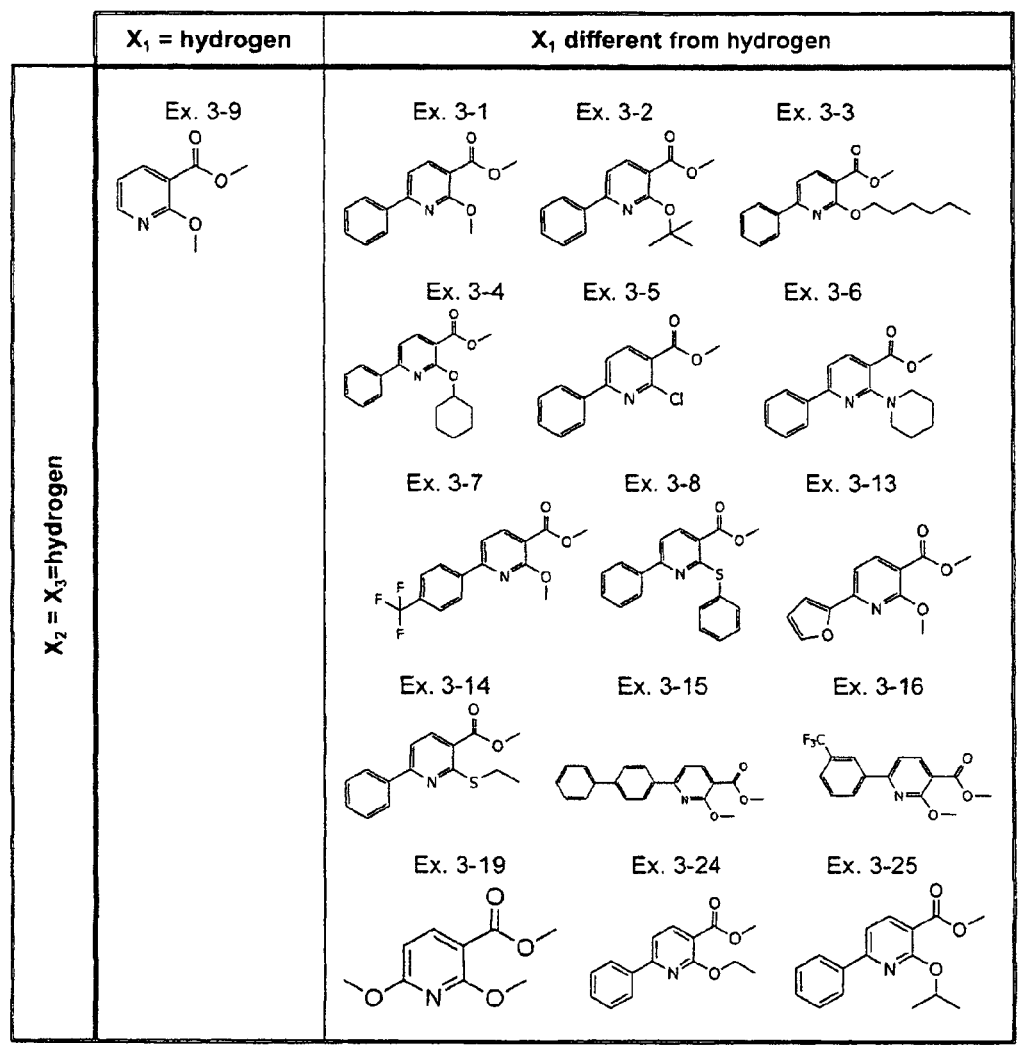
Figure 3E:
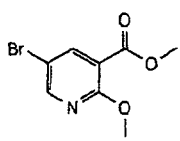

Synthesis of the Intermediates of the Alkoxy, Alkylthio, Alkylamino, Halo-Pyridine Type According to the Invention Synthesis of the intermediates in FIG. 3a is summarized in Table 3-1.

TABLE 3-1

| Ex. | Intermediates (Protocols) | Details |
|---|---|---|
| 3-1 | Methyl 2-methoxy-6-phenyl-pyridine-3-carboxylate (Protocol SF and PA) | Yield: 73%. Appearance: colorless oil. $^1$H NMR: 3.94 (s, 3H); 4.19 (s, 3H); 7.42-7.54 (m, 4H); 8.11 (dd, 2H, J = 1.7 Hz J = 7.9 Hz); 8.27 (d, 1H, J = 7.9 Hz). |
| 3-2 | Methyl 2-tert-butoxy-6-phenyl-pyridine-3-carboxylate (Protocol SF and PA) | Yield: 56%. Appearance: white solid. $^1$H NMR: 1.74 (s, 9H); 3.91 (s, 3H); 7.38 (d, 1H, J = 7.9 Hz); 7.45-7.52 (m, 3H); 8.06 (m, 2H); 8.19 (d, 1H, J = 7.9 Hz). |
| 3-3 | Methyl 2-hexyloxy-6-phenyl-pyridine-3-carboxylate (Protocol SF and PA) | Yield: 80%. Appearance: colorless oil. $^1$H NMR: 0.93 (t, 3H, J = 6.7 Hz); 1.34-1.42 (m, 4H); 1.50-1.57 (m, 2H); 1.85-1.94 (m, 2H); 3.93 (s, 3H); 4.58 (t, 2H, J = 6.7 Hz); 7.41 (d, 1H, J = 7.9 Hz); 7.43-7.53 (m, 3H); 8.09 (dd, 2H, J = 1.9 Hz, J = 8.1 Hz); 8.26 (d, 1H, J = 7.9 Hz). |
| 3-4 | Methyl 2-cyclohexyloxy-6-phenyl-pyridine-3-carboxylate (Protocol SF and PA) | Yield: 12%. Appearance: colorless oil. $^1$H NMR: 1.46-2.09 (m, 10H); 3.92 (s, 3H); 5.41-5.46 (m, 1H); 7.38 (d, 1H, J = 7.9 Hz); 7.45-7.53 (m, 3H); 8.06 (dd, 2H, J = 1.9 Hz, J = 8.2 Hz); 8.24 (d, 1H, J = 7.9 Hz). |
| 3-7 | Methyl 2-methoxy-6-(4-(trifluoromethyl)phenyl)-pyridine-3-carboxylate (Protocol SF and PA) | Yield: 67%. Appearance: white solid. $^1$H NMR: 3.94 (s, 3H); 4.18 (s, 3H); 7.46 (d, 1H, J = 7.6 Hz); 7.75 (d, 2H, J = 8.2 Hz); 8.21 (d, 2H, J = 8.2 Hz); 8.29 (d, 1H, J = 7.6 Hz). |
| 3-9 | Methyl 2-methoxy-pyridine-3-carboxylate (Protocol SE and PA) | Yield: 38%. Appearance: colorless oil. $^1$H NMR: 3.90 (s, 3H); 4.04 (s, 3H); 6.95 (dd, 1H, J = 4.8 Hz, J = 7.5 Hz); 8.15 (dd, 1H, J = 2.0 Hz J = 7.5 Hz); 8.31 (dd, 1H, J = 2.0 Hz J = 4.8 Hz). |
| 3-12 | Methyl 5-bromo-2-methoxy-6-phenyl-pyridine-3-carboxylate (Protocol SF and PA) | Yield: 48%. Appearance: white solid. $^1$H NMR: 3.94 (s, 3H); 4.07 (s, 3H); 7.45-7.50 (m, 3H); 7.78-7.82 (m, 2H); 8.43 (s, 1H). |
| 3-13 | Methyl 2-methoxy-6-furyl-pyridine-3-carboxylate (Protocol SF and PA) | Yield: 70%. Appearance: white solid. $^1$H NMR: 3.91 (s, 3H); 4.11 (s, 3H); 6.55-6.57 (m, 1H); 7.15 (d, 1H, J = 3.5 Hz); 7.33 (d, 1H, J = 7.9 Hz); 7.56 (m, 1H); 8.23 (d, 1H, J = 7.9 Hz). |
| 3-15 | Methyl 2-methoxy-6-(parabiphenyl)-pyridine-3-carboxylate (Protocol SF and PA) | Appearance: white solid. $^1$H NMR: 3.94 (s, 3H); 4.20 (s, 3H); 7.34-7.40 (m, 1H); 7.46-7.51 (m, 3H); 7.67 (d, 2H, J = 7.6 Hz); 7.73 (d, 2H, J = 8.2 Hz); 8.19 (d, 2H, J = 8.2 Hz); 8.28 (d, 1H, J = 7.6 Hz). |
| 3-16 | Methyl 2-methoxy-6-(3-(trifluoromethyl)phenyl)-pyridine-3-carboxylate (Protocol SF and PA) | Yield: 30%. Appearance: white solid $^1$H NMR: 3.93 (s, 3H); 4.17 (s, 3H); 7.43 (d, 1H, J = 7.7 Hz); 7.59 (m, 1H); 7.69 (d, 1H, J = 7.9 Hz); 8.24-8.26 (m, 1H); 8.27 (d, 1H, J = 7.7 Hz); 8.33 (s, 1H). |
| 3-24 | Methyl 2-ethoxy-6-phenyl-pyridine-3-carboxylate (Protocol SF and PA) | Yield: 86%. Appearance: white solid. $^1$H NMR: 1.51 (t, 3H, J = 7.0 Hz); 3.92 (s, 3H); 4.65 (q, 2H, J = 7.0 Hz); 7.40 (d, 1H, J = 7.9 Hz); 7.43-7.52 (m, 3H); 8.08 (dd, 2H, J = 2.1 Hz J = 8.2 Hz); 8.24 (d, 1H, J = 7.9 Hz). |
| 3-25 | Methyl 2-isopropoxy-6-phenyl-pyridine-3-carboxylate (Protocol SF and PA) | Yield: 74%. Appearance: colorless oil. $^1$H NMR: 1.47 (s, 3H); 1.49 (s, 3H); 3.91 (s, 3H); 5.58-5.66 (m, 1H); 7.37 (d, 1H, J = 7.9 Hz); 7.42-7.52 (m, 3H); 8.07 (dd, 2H, J = 2.0 Hz, J = 8.2 Hz); 8.22 (d, 1H, J = 7.9 Hz). |

Introduction of groups in position 5, and notably of groups of the aryl or alkyl type, can be performed by coupling of the Suzuki type between the appropriately selected boronic acid precursor and the appropriate 5-halopyridine. The intermediates 3-11, 3-17, 3-18, 3-21 to 3-23 were prepared from 5-bromopyridines 3-10 and 3-20. The synthesis of these intermediates (FIG. 3b) is summarized in Table 3-2.

TABLE 3-2

| Ex. | Intermediate (Protocol) | Details |
|---|---|---|
| 3-10 | Methyl 5-bromo-2-methoxy-pyridine-3-carboxylate (Protocol SE and PE) | Yield: 33%. Appearance: gray solid. $^1$H NMR: 3.81 (s, 3H); 3.91 (s, 3H); 8.24 (d, 1H, J = 2.3 Hz); 8.50 (d, 1H, J = 2.3 Hz). |

TABLE 3-2-continued

| Ex. | Intermediate (Protocol) | Details |
| --- | --- | --- |
| 3-11 | Methyl 2-methoxy-5-phenyl-pyridine-3-carboxylate (Protocol SI and PA) | Yield: 71%. Appearance: colorless oil.<br>$^1$H NMR: 3.94 (s, 3H); 4.11 (s, 3H); 7.36-7.42 (m, 1H); 7.45-7.50 (m, 2H); 7.55-7.58 (m, 2H); 8.39 (d, 1H, J = 2.6 Hz); 8.55 (d, 1H, J = 2.6 Hz). |
| 3-17 | Methyl 2-methoxy-5-(4-(trifluoromethyl)phenyl)-pyridine-3-carboxylate (Protocol SI and PA) | Yield: 21%. Appearance: white solid.<br>$^1$H NMR: 3.96 (s, 3H); 4.12 (s, 3H); 7.67 (d, 2H, J = 8.3 Hz); 7.74 (d, 2H, J = 8.3 Hz); 8.40 (d, 1H, J = 2.6 Hz); 8.57 (d, 1H, J = 2.6 Hz). |
| 3-18 | Methyl 2-methoxy-5-(3-(trifluoromethyl)phenyl)-pyridine-3-carboxylate (Protocol SI and PA) | Yield: 30%. Appearance: white solid.<br>$^1$H NMR: 3.92 (s, 3H); 4.12 (s, 3H); 7.57-7.67 (m, 2H); 7.73-7.75 (m, 1H); 7.80 (s, 1H); 8.39 (d, 1H, J = 2.6 Hz); 8.56 (d, 1H, J = 2.6 Hz). |
| 3-19 | Methyl 2,6-dimethoxy-pyridine-3-carboxylate (Protocol SQ and PA) | Yield: 69%. Appearance: white solid.<br>$^1$H NMR: 3.86 (s, 3H); 3.98 (s, 3H); 4.05 (s, 3H); 6.33 (d, 1H, J = 8.2 Hz); 8.14 (d, 1H, J = 8.2 Hz). |
| 3-20 | Methyl 5-bromo-2,6-dimethoxy-pyridine-3-carboxylate (Protocol SE and PE) | Yield: 81%. Appearance: white solid.<br>$^1$H NMR: 3.76 (s, 3H); 3.96 (s, 3H); 4.01 (s, 3H); 8.24 (s, 1H). |
| 3-21 | Methyl 5-phenyl-2,6-dimethoxy-pyridine-3-carboxylate (Protocol SI and PA) | Yield: 76%. Appearance: white solid.<br>$^1$H NMR: 3.88 (s, 3H); 4.03 (s, 3H); 4.11 (s, 3H); 7.31-7.36 (m, 1H); 7.39-7.44 (m, 2H); 7.52-7.55 (m, 2H); 8.26 (s, 1H). |
| 3-22 | Methyl 5-(4-chlorophenyl)-2-methoxy-pyridine-3-carboxylate (Protocol SI and PA) | Yield: 97%. Appearance: white solid.<br>$^1$H NMR: 3.95 (s, 3H); 4.10 (s, 3H); 7.44 (d, 2H, J = 8.8 Hz); 7.49 (d, 2H, J = 8.8 Hz); 8.35 (d, 1H, J = 2.4 Hz); 8.50 (d, 1H, J = 2.4 Hz). |
| 3-23 | Methyl 5-(naphthalen-2-yl)-2-methoxy-pyridine-3-carboxylate (Protocol SI and PA) | Yield: 84%. Appearance: white solid.<br>$^1$H NMR: 3.97 (s, 3H); 4.13 (s, 3H); 7.49-7.57 (m, 2H); 7.70 (dd, 1H, J = 2.0 Hz J = 8.5 Hz); 7.87-7.97 (m, 3H); 8.02 (s, 1H); 8.52 (d, 1H, J = 2.5 Hz); 8.68 (d, 1H, J = 2.5 Hz). |

Intermediates substituted in position 2 with alkylthio, alkylamino groups are accessible starting from the corresponding 2-halopyridine. The intermediates 3-6, 3-8 and 3-14 were prepared from 2-chloropyridine 3-5 (FIG. 3c), as summarized in Table 3-3.

TABLE 3-3

| Ex. | Intermediate (protocols) | Details |
| --- | --- | --- |
| 3-5 | Methyl 2-chloro-6-phenyl-pyridine-3-carboxylate (Protocol SG and PA) | Yield: 83%. Appearance: white solid.<br>$^1$H NMR: 3.99 (s, 3H); 7.48-7.53 (m, 3H); 7.75 (d, 1H, J = 8.1 Hz); 8.05-8.08 (m, 2H); 8.26 (d, 1H, J = 8.1 Hz). |
| 3-6 | Methyl 2-(piperidin-1-yl)-6-phenyl-pyridine-3-carboxylate (intermediate 3-5 is dissolved in piperidine (0.1 mol/L) and the whole is stirred under reflux for 16 hours; Protocol PA) | Yield: 95%. Appearance: yellow oil.<br>$^1$H NMR: 1.60-1.73 (m, 6H); 3.47-3.49 (m, 4H); 3.91 (s, 3H); 7.18 (d, 1H, J = 7.9 Hz); 7.41-7.49 (m, 3H); 8.05 (d, 1H, J = 7.9 Hz); 8.06 (dd, 2H, J = 1.6 Hz, J = 8.2 Hz). |
| 3-8 | Methyl 2-phenylthio-6-phenyl-pyridine-3-carboxylate (Protocol SH and PA) | Yield: quantitative. Appearance: colorless oil.<br>$^1$H NMR: 4.01 (s, 3H); 7.25-7.35 (m, 3H); 7.46-7.53 (m, 4H); 7.60-7.66 (m, 4H); 8.28 (d, 1H, J = 8.2 Hz). |
| 3-14 | Methyl 2-ethylthio-6-phenyl-pyridine-3-carboxylate (Protocol SH and PA) | Yield: 90%. Appearance: beige solid.<br>$^1$H NMR: 1.47 (t, 3H, J = 7.3 Hz); 3.34 (q, 2H, J = 7.3 Hz); 3.95 (s, 3H); 7.47-7.54 (m, 4H); 8.11-8.14 (m, 2H); 8.28 (d, 1H, J = 8.2 Hz). |

Example 4

Figure 4A:
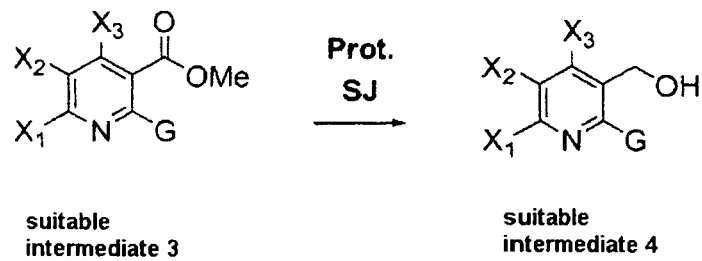

Synthesis of the Intermediates of the 3-Hydroxymethyl-, 3-Halomethyl- and 3-Arylsulfonylmethyl-Pyridine Type According to the Invention Synthesis of the intermediates in FIG. 4a is summarized in Table 4-1.

TABLE 4-1

| Ex. | Intermediate (Protocol) | Details |
|---|---|---|
| 4-1 | (2-methoxy-6-phenylpyridin-3-yl)methanol (Protocol SJ and PA) | Yield: 96%. Appearance: yellow solid. $^1$H NMR: 4.12 (s, 3H); 4.71 (s, 2H); 7.36-7.50 (m, 4H); 7.64 (d, 1H, J = 7.3 Hz); 8.06 (m, 2H). |
| 4-2 | (2-tert-butoxy-6-phenylpyridin-3-yl)methanol (Protocol SJ and PA) | Yield: 91%. Appearance: white solid. $^1$H NMR: 1.73 (s, 9H); 4.64 (s, 2H); 7.33 (d, 1H, J = 7.5 Hz); 7.37-7.50 (m, 3H); 7.58 (d, 1H, J = 7.5 Hz); 8.02 (m, 2H). |
| 4-3 | (2-hexyloxy-6-phenylpyridin-3-yl)methanol (Protocol SJ) | Yield: quantitative. Appearance: white solid. $^1$H NMR: 0.92 (t, 3H, J = 6.7 Hz); 1.27-1.53 (m, 6H); 1.80-1.90 (m, 2H); 4.52 (t, 2H, J = 6.7 Hz); 4.70 (d, 2H, J = 6.2 Hz); 7.34 (d, 1H, J = 7.3 Hz); 7.37-7.49 (m, 3H); 7.62 (d, 1H, J = 7.6 Hz); 8.02-8.05 (m, 2H). |
| 4-4 | (2-cyclohexyloxy-6-phenylpyridin-3-yl)methanol (Protocol SJ) | Yield: 88%. Appearance: clear oil. $^1$H NMR: 1.37-1.69 (m, 6H); 1.79-1.83 (m, 2H); 2.05 (m, 2H); 4.68 (d, 2H, J = 6.4 Hz); 5.32-5.38 (m, 1H); 7.32 (d, 1H, J = 7.3 Hz); 7.36-7.49 (m, 3H); 7.60 (d, 1H, J = 7.6 Hz); 8.01 (m, 2H). |
| 4-5 | (6-phenyl-2-(piperidin-1-yl)pyridin-3-yl)methanol (Protocol SJ and PA) | Yield: 46%. Appearance: white solid. $^1$H NMR: 1.62-1.83 (m, 6H); 3.18-3.22 (t, 4H, J = 5.4 Hz); 4.80 (s, 2H); 4.94 (s, 1H); 7.36-7.49 (m, 4H); 7.57 (d, 1H, J = 7.9 Hz); 8.04 (m, 2H). |
| 4-6 | (2-methoxy-6-(4-(trifluoromethyl)phenyl)pyridin-3-yl)methanol (Protocol SJ and PA) | Yield: 93%. Appearance: white solid. $^1$H NMR: 4.12 (s, 3H); 4.72 (s, 2H); 7.41 (d, 1H, J = 7.6 Hz); 7.68-7.73 (m, 3H); 8.16 (d, 2H, J = 8.2 Hz). |
| 4-7 | (6-phenyl-2-(phenylthio)pyridin-3-yl)methanol (Protocol SJ and PA) | Yield: 39%. Appearance: white solid. $^1$H NMR: 4.84 (s, 2H); 7.31-7.36 (m, 3H); 7.38-7.46 (m, 3H); 7.55-7.63 (m, 3H); 7.73-7.78 (m, 3H). |
| 4-8 | (2-methoxy-5-phenylpyridin-3-yl)methanol (Protocol SJ) | Yield: quantitative. Appearance white solid. $^1$H NMR: 4.05 (s, 3H); 4.73 (s, 2H); 7.34-7.39 (m, 1H); 7.43-7.47 (m, 2H); 7.53-7.56 (m, 2H); 7.83 (d, 1H, J = 2.3 Hz); 8.32 (d, 1H, J = 2.3 Hz). |
| 4-9 | (5-bromo-2-methoxy-6-phenylpyridin-3-yl)methanol (Protocol SJ and PA) | Yield: 50%. Appearance: white solid. $^1$H NMR: 4.00 (s, 3H); 4.68 (s, 2H); 7.42-7.50 (m, 3H); 7.74-7.77 (m, 2H); 7.86 (s, 1H). |
| 4-10 | (2-methoxy-6-furylpyridin-3-yl)methanol (Protocol SJ and PA) | Yield: 78%. Appearance: white solid. $^1$H NMR: 2.25 (t, 1H, J = 6.3 Hz); 4.05 (s, 3H); 4.66 (d, 2H, J = 6.3 Hz); 6.51-6.53 (m, 1H); 7.01-7.02 (m, 1H); 7.29 (d, 1H, J = 7.6 Hz); 7.5-7.51 (m, 1H); 7.60 (d, 1H, J = 7.6 Hz). |
| 4-12 | (2-(ethylthio)-6-phenylpyridin-3-yl)methanol (Protocol SJ and PA) | Yield: 75%. Appearance: yellow oil. $^1$H NMR: 1.47 (t, 3H, J = 7.3 Hz); 3.39 (q, 2H, J = 7.3 Hz); 4.72 (s, 2H); 7.39-7.51 (m, 4H); 7.67 (d, 1H, J = 7.9 Hz); 8.07 (d, 2H, J = 7.0 Hz). |
| 4-13 | (2-methoxy-6 (parabiphenyl) pyridin-3-yl)methanol (Protocol SJ and PA) | Yield: 59%. Appearance: white solid. $^1$H NMR: 2.29 (t, 1H, J = 6.6 Hz); 4.14 (s, 3H); 4.71 (d, 2H, J = 6.6 Hz); 7.36-7.50 (m, 4H); 7.65-7.72 (m, 5H); 8.14 (d, 2H, J = 6.7 Hz). |
| 4-14 | (2-methoxy-6-(3-(trifluoromethyl)phenyl)pyridin-3-yl)methanol (Protocol SJ and PA) | Yield: 85%. Appearance: white solid. $^1$H NMR: 2.26 (t, 1H, J = 6.6 Hz); 4.12 (s, 3H); 4.72 (d, 2H, J = 6.6 Hz); 7.41 (d, 1H, J = 7.3 Hz); 7.56-7.70 (m, 3H); 8.22 (d, 1H, J = 7.9 Hz); 8.31 (s, 1H). |
| 4-17 | (2-methoxy-5-(4-(trifluoromethyl)phenyl)pyridin-3-yl)methanol (Protocol SJ) | Yield: quantitative. Appearance: white solid. $^1$H NMR: 4.02 (s, 3H); 4.72 (d, 2H, J = 5.3 Hz); 7.60 (d, 2H, J = 8.3 Hz); 7.67 (d, 2H, J = 8.3 Hz); 7.86 (d, 1H, J = 2.5 Hz); 8.30 (d, 1H, J = 2.5 Hz). |
| 4-18 | (2-methoxy-5-(3-(trifluoromethyl)phenyl)pyridin-3-yl)methanol (Protocol SJ) | Yield: 77%. Appearance: white solid. $^1$H NMR: 4.05 (s, 3H); 4.74 (s, 2H); 7.54-7.63 (m, 2H); 7.71-7.73 (m, 1H); 7.78 (s, 1H); 7.85 (d, 1H, J = 2.5 Hz); 8.33 (d, 1H, J = 2.5 Hz). |
| 4-19 | (2,6-dimethoxy-5-phenylpyridin-3-yl)methanol (Protocol SJ and PA) | Yield: 77%. Appearance: white solid. $^1$H NMR: 3.98 (s, 3H); 4.04 (s, 3H); 4.65 (s, 2H); 7.30-7.33 (m, 1H); 7.38-7.43 (m, 2H); 7.52-7.57 (m, 3H). |
| 4-20 | (5-(4-chlorophenyl)-2-methoxypyridin-3-yl)methanol (Protocol SJ) | Yield: 84%. Appearance: colorless oil. $^1$H NMR: 4.04 (s, 3H); 4.72 (d, 2H, J = 6.5 Hz); 7.42 (d, 2H, J = 8.8 Hz); 7.47 (d, 2H, J = 8.8 Hz); 7.79 (d, 1H, J = 2.3 Hz); 8.28 (d, 1H, J = 2.3 Hz). |

TABLE 4-1-continued

| Ex. | Intermediate (Protocol) | Details |
| --- | --- | --- |
| 4-21 | (2-methoxy-5-(naphthalen-2-yl)pyridin-3-yl)methanol (Protocol SJ and PA) | Yield: 75%. Appearance: white solid.<br>$^1$H NMR: 4.07 (s, 3H); 4.77 (s, 2H); 7.49-7.53 (m, 2H); 7.69 (dd, 1H, J = 1.9 Hz, J = 8.5 Hz); 7.86-7.99 (m, 5H); 8.45 (d, 1H, J = 2.5 Hz). |
| 4-22 | (2-ethoxy-6-phenylpyridin-3-yl)methanol (Protocol SJ) | Yield: 91%. Appearance: white solid.<br>$^1$H NMR: 1.47 (t, 3H, J = 7.2 Hz); 4.59 (q, 2H, J = 7.2 Hz); 4.69 (d, 2H, J = 5.6 Hz); 7.34 (d, 1H, J = 7.6 Hz); 7.37-7.49 (m, 3H); 7.62 (d, 1H, J = 7.6 Hz); 8.01-8.05 (m, 2H). |
| 4-23 | (2-isopropoxy-6-phenylpyridin-3-yl)methanol (Protocol SJ) | Yield: quantitative. Appearance: colorless oil.<br>$^1$H NMR: 1.43 (s, 3H); 1.45 (s, 3H); 4.67 (d, 2H, J = 6.4 Hz); 5.56-5.64 (m, 1H); 7.32 (d, 1H, J = 7.5 Hz); 7.36-7.49 (m, 3H); 7.60 (d, 1H, J = 7.5 Hz); 8.00-8.04 (m, 2H). |

Figure 4B:
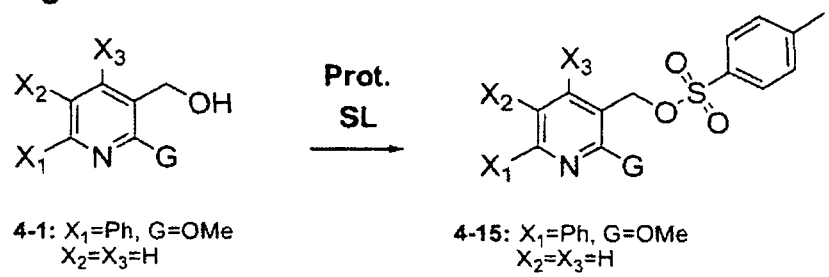
Figure 4C:
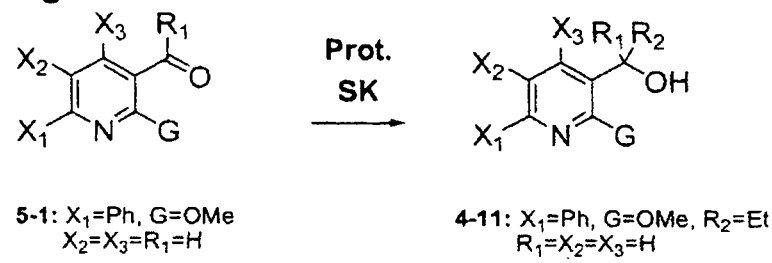
Figure 4D:
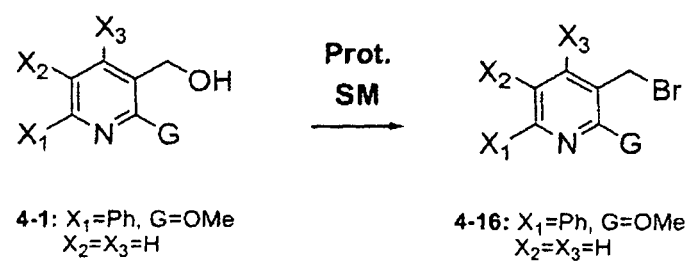
Figure 4E:
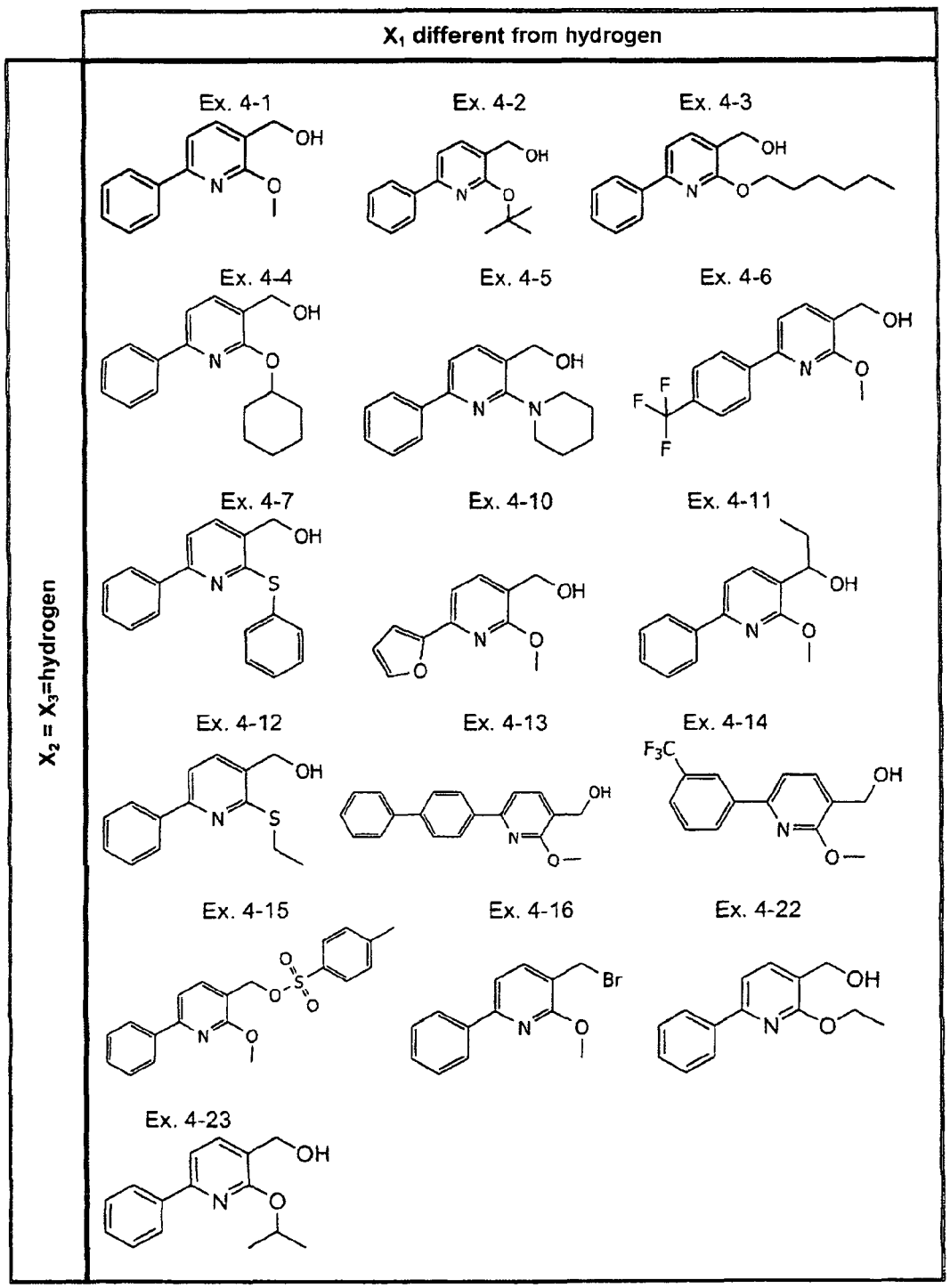
Figure 4F:
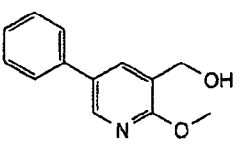

Synthesis of the intermediates in FIGS. 4b, 4c and 4d is summarized in Table 4-2

TABLE 4-2

| Ex. | Intermediate (Protocol) | Details |
| --- | --- | --- |
| 4-11 | 1-(2-methoxy-6-phenylpyridin-3-yl)propan-1-ol (Protocol SK and PA) | Yield: 66%. Appearance: beige solid<br>$^1$H NMR: 0.99 (t, 3H, J = 7.3 Hz); 1.86 (m, 2H); 4.10 (s, 3H); 4.77 (t, 1H, J = 6.4 Hz); 7.37-7.50 (m, 4H); 7.65 (d, 1H, J = 7.6 Hz); 8.06 (d, 2H, J = 7.0 Hz). |
| 4-15 | (2-methoxy-6-phenylpyridin-3-yl)methyl-4-methylbenzenesulfonate (Protocol SL and PA) | Yield: 31%. Appearance: yellow oil.<br>$^1$H NMR: 2.51 (s, 3H); 4.13 (s, 3H); 4.67 (s, 2H); 7.37-7.51 (m, 6H); 7.72 (d, 1H, J = 7.6 Hz); 7.95 (d, 2H, J = 8.5 Hz); 8.07 (m, 2H). |
| 4-16 | 3-(bromomethyl)-2-methoxy-6-phenylpyridine (Protocol SM) | Yield: 91%. Appearance: white solid.<br>$^1$H NMR: 4.14 (s, 3H); 4.57 (s, 2H); 7.36 (d, 1H, J = 7.6 Hz); 7.42-7.53 (m, 3H); 7.68 (d, 1H, J = 7.6 Hz); 8.06 (m, 2H). |

Example 5

Figure 5A:
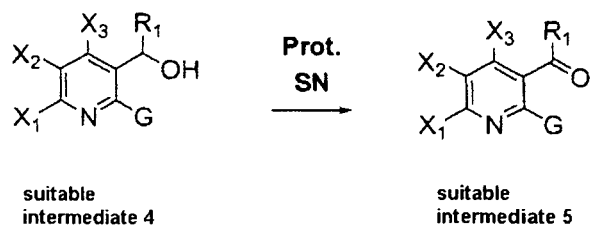

Synthesis of the Intermediates of the Pyridine 3-Carboxaldehyde and Ketone Type According to the Invention Synthesis of the intermediates in FIG. 5a is summarized in Table 5-1.

TABLE 5-1

| Ex. | Intermediates (Protocols) | Details |
| --- | --- | --- |
| 5-1 | 2-methoxy-6-phenyl-pyridine-3-carboxaldehyde (Protocol SN and PA) | Yield: 63%. Appearance: white solid.<br>$^1$H NMR: 4.20 (s, 3H); 7.50 (m, 4H); 8.11 (m, 2H); 8.19 (d, 1H, J = 7.9 Hz); 10.40 (s, 1H). |
| 5-3 | 2-methoxy-6-(4-(trifluoromethyl)phenyl)-pyridine-3-carboxaldehyde (Protocol SN and PA) | Yield: 94%. Appearance: white solid.<br>$^1$H NMR: 4.16 (s, 3H); 7.48 (d, 1H, J = 7.9 Hz); 7.72 (d, 2H, J = 8.2 Hz); 8.16-8.19 (m, 3H); 10.38 (s, 1H). |
| 5-4 | 2-methoxy-5-phenyl-pyridine-3-carboxaldehyde (Protocol SN and PA) | Yield: 63%. Appearance: white solid.<br>$^1$H NMR: 4.14 (s, 3H); 7.38-7.43 (m, 1H); 7.46-7.51 (m, 2H); 7.55-7.59 (m, 2H); 8.34 (d, 1H, J = 2.6 Hz); 8.63 (d, 1H, J = 2.6 Hz); 10.44 (s, 1H). |
| 5-6 | 5-bromo-2-methoxy-6-phenylpyridine-3-carboxaldehyde (Protocol SN and PA) | Yield: 63%. Appearance: white solid.<br>$^1$H NMR: 4.10 (s, 3H); 7.48-7.51 (m, 3H); 7.77-7.82 (m, 2H); 8.35 (s, 1H); 10.33 (s, 1H). |
| 5-7 | 2-methoxy-6-furyl-pyridine-3-carboxaldehyde (Protocol SN and PA) | Yield: 86%. Appearance: yellow solid.<br>$^1$H NMR: 4.07 (s, 3H); 6.73-6.75 (m, 1H); 7.34 (d, 1H, J = 3.2 Hz); 7.48 (d, 1H, J = 7.9 Hz); 7.97 (m, 1H); 8.14 (d, 1H, J = 7.9 Hz); 10.21 (s, 1H). |
| 5-8 | 1-(2-methoxy-6-phenylpyridin-3-yl)propan-1-one (Protocol SN and PA) | Yield: 92%. Appearance: white solid.<br>$^1$H NMR: 1.21 (t, 3H, J = 7.2 Hz); 3.09 (q, 2H, J = 7.2 Hz); 4.17 (s, 3H); 7.45-7.52 (m, 4H); 8.10 (d, 2H, J = 7.9 Hz); 8.22 (d, 1H, J = 7.9 Hz). |

TABLE 5-1-continued

| Ex. | Intermediates (Protocols) | Details |
|---|---|---|
| 5-9 | 2-ethylthio-6-phenyl-pyridine-3-carboxaldehyde (Protocol SN and PA) | Yield: 86%. Appearance: yellow oil.<br>$^1$H NMR: 1.49 (t, 3H, J = 7.3 Hz); 3.42 (q, 2H, J = 7.3 Hz); 7.51-7.55 (m, 3H); 7.62 (d, 1H, J = 7.9 Hz); 8.08 (d, 1H, J = 7.9 Hz); 8.12-8.15 (m, 2H); 10.27 (s, 1H). |
| 5-10 | 2-methoxy-6-(parabiphenyl)-pyridine-3-carboxaldehyde (Protocol SN and PA) | Yield: 79%. Appearance: white solid.<br>$^1$H NMR: 4.22 (s, 3H); 7.41-7.43 (m, 1H); 7.49-.756 (m, 3H); 7.66-7.69 (m, 2H); 7.73-7.76 (m, 2H); 8.20-8.22 (m, 3H); 10.41 (s, 1H). |
| 5-11 | 2-methoxy-6-(3-(trifluoromethyl)phenyl)-pyridine-3-carboxaldehyde (Protocol SN and PA) | Yield: 68%. Appearance: white solid.<br>$^1$H NMR: 4.21 (s, 3H); 7.53 (d, 1H, J = 7.9 Hz); 7.64 (t, 1H, J = 7.9 Hz); 7.73 (d, 1H, J = 7.9 Hz); 8.23 (d, 1H, J = 7.9 Hz); 8.29 (d, 1H, J = 7.9 Hz); 8.37 (s, 1H); 10.41 (s, 1H). |
| 5-12 | 2-methoxy-5-(4-(trifluoromethyl)phenyl)-pyridine-3-carboxaldehyde (Protocol SN and PA) | Yield: 70%. Appearance: white solid.<br>$^1$H NMR: 4.15 (s, 3H); 7.68 (d, 2H, J = 8.2 Hz); 7.73 (d, 2H, J = 8.2 Hz); 8.35 (d, 1H, J = 2.7 Hz); 8.65 (d, 1H, J = 2.7 Hz); 10.44 (s, 1H). |
| 5-13 | 2-methoxy-5-(3-(trifluoromethyl)phenyl)-pyridine-3-carboxaldehyde (Protocol SN and PA) | Yield: 58%. Appearance: white solid.<br>$^1$H NMR: 4.15 (s, 3H); 7.55-7.68 (m, 2H); 7.74 (d, 1H, J = 7.3 Hz); 7.81 (s, 1H); 8.34 (d, 1H, J = 2.6 Hz); 8.64 (d, 1H, J = 2.6 Hz); 10.45 (s, 1H). |
| 5-14 | 2,6-dimethoxy-5-phenyl-pyridine-3-carboxaldehyde (Protocol SN and PA) | Yield: 93%. Appearance: white solid.<br>$^1$H NMR: 4.07 (s, 3H); 4.12 (s, 3H); 7.32-7.45 (m, 3H); 7.50-7.54 (m, 2H); 8.13 (s, 1H); 10.27 (s, 1H). |
| 5-15 | 2-methoxy-5-(4-chlorophenyl)-pyridine-3-carboxaldehyde (Protocol SN and PA) | Yield: 58%. Appearance: white solid.<br>$^1$H NMR: 4.14 (s, 3H); 7.45 (d, 2H, J = 8.8 Hz); 7.49 (d, 2H, J = 8.8 Hz); 8.30 (d, 1H, J = 2.6 Hz); 8.59 (d, 1H, J = 2.6 Hz); 10.43 (s, 1H). |
| 5-16 | 2-methoxy-5-(naphthalen-2-yl)-pyridine-3-carboxaldehyde (Protocol SN and PA) | Yield: 75%. Appearance: white solid.<br>$^1$H NMR: 4.16 (s, 3H); 7.50-7.57 (m, 2H); 7.70 (dd, 1H, J = 1.9 Hz J = 8.5 Hz); 7.87-7.97 (m, 3H); 8.03 (d, 1H, J = 1.5 Hz); 8.46 (d, 1H, J = 2.6 Hz); 8.76 (d, 1H, J = 2.6 Hz); 10.47 (s, 1H). |
| 5-17 | 2-ethoxy-6-phenyl-pyridine-3-carboxaldehyde (Protocol SN and PA) | Yield: 87%. Appearance: white solid.<br>$^1$H NMR: 1.52 (t, 3H, J = 7.0 Hz); 4.67 (q, 2H, J = 7.0 Hz); 7.44-7.54 (m, 4H); 8.07-8.11 (m, 2H); 8.18 (d, 1H, J = 7.9 Hz); 10.42 (s, 1H). |
| 5-18 | 2-isopropoxy-6-phenyl-pyridine-3-carboxaldehyde (Protocol SN and PA) | Yield: 77%. Appearance: colorless oil.<br>$^1$H NMR: 1.48 (s, 3H); 1.50 (s, 3H); 5.64-5.72 (m, 1H); 7.43-7.53 (m, 4H); 8.07-8.10 (m, 2H); 8.17 (d, 1H, J = 7.9 Hz); 10.40 (s, 1H). |

Figure 5B:
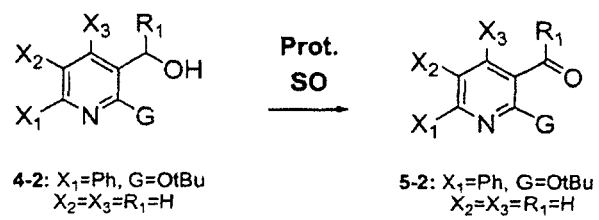
Figure 5C:
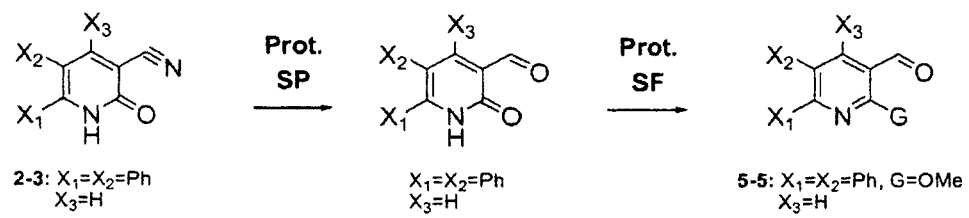
Figure 5D:
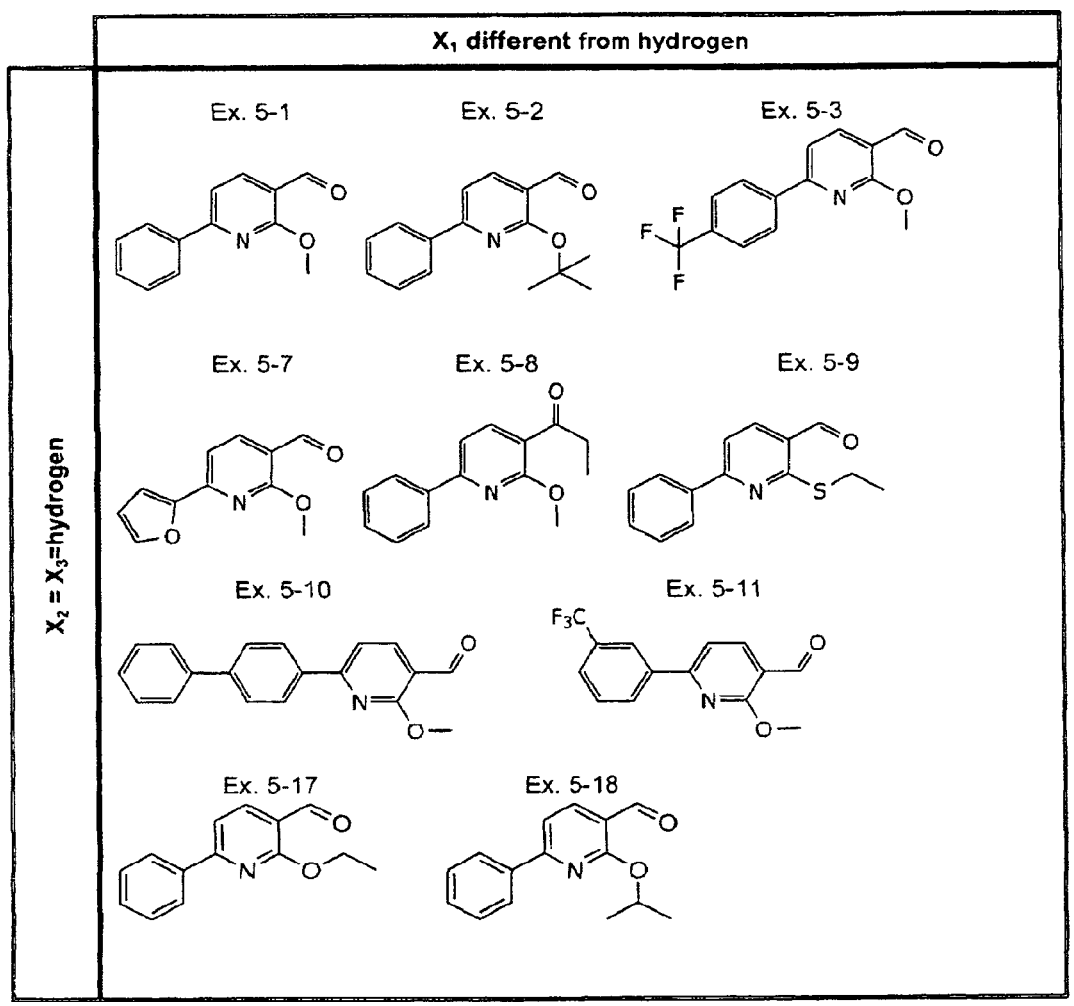
Figure 5E:
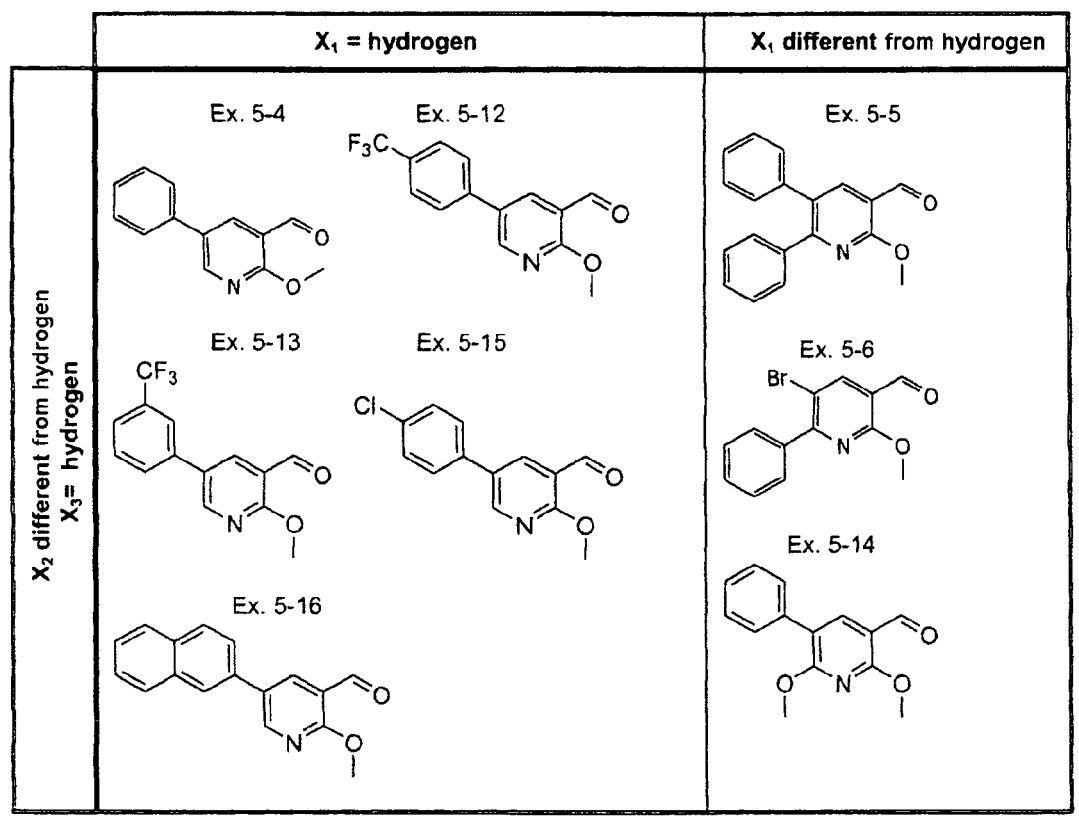

Synthesis of the intermediates in FIGS. 5b and 5c is summarized in Table 5-2.

TABLE 5-2

| Ex. No. and type of Stage (Protocol) | Details |
|---|---|
| 5-2 2-tert-butoxy-6-phenyl-pyridine-3-carboxaldehyde (Protocol SO and PA) | Yield: 83%. Appearance: white solid.<br>$^1$H NMR: 1.76 (s, 9H); 7.42-7.53 (m, 4H); 8.07 (m, 2H); 8.16 (d, 1H, J = 8.2 Hz); 10.36 (s, 1H). |
| 5-5 Stage 1: Preparation of 5,6-diphenyl-2-oxo-pyridine-3-carboxaldehyde (Protocol SP and PA) | Yield: 59%. Appearance: yellow solid.<br>$^1$H NMR: 7.07-7.10 (m, 2H); 7.25-7.43 (m, 8H); 8.23 (s, 1H); 10.27 (s, 1H). |
| Stage 2: Obtaining 2-methoxy-5,6-diphenyl-pyridine-3-carboxaldehyde (Protocol SF and PA) | Yield: 16%. Appearance: white solid.<br>$^1$H NMR: 4.18 (s, 3H); 7.14-7.20 (m, 2H); 7.26-7.34 (m, 6H); 7.44-7.47 (m, 2H); 8.16 (s, 1H); 10.44 (s, 1H). |

Example 6

Synthesis of the Intermediates of the Phenol, Thiophenol, Aniline Type

Figure 6A:
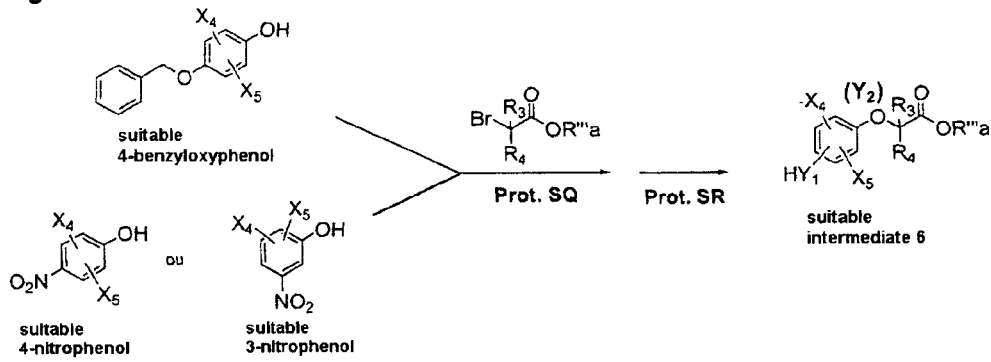
Figure 6B:
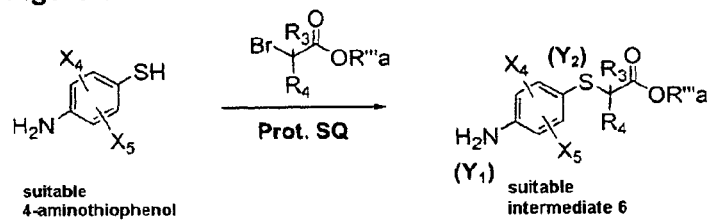
Figure 6C:
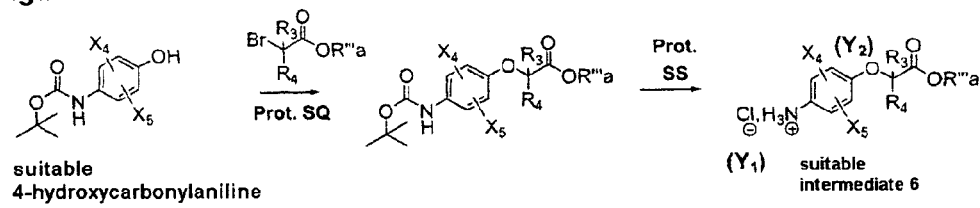
Figure 6D:
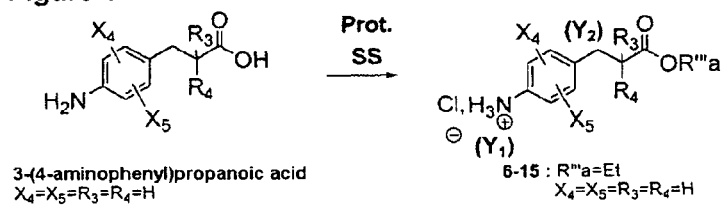
Figure 6E:
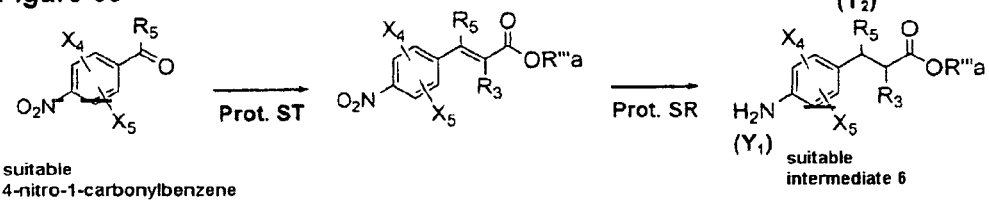
Figure 6F:
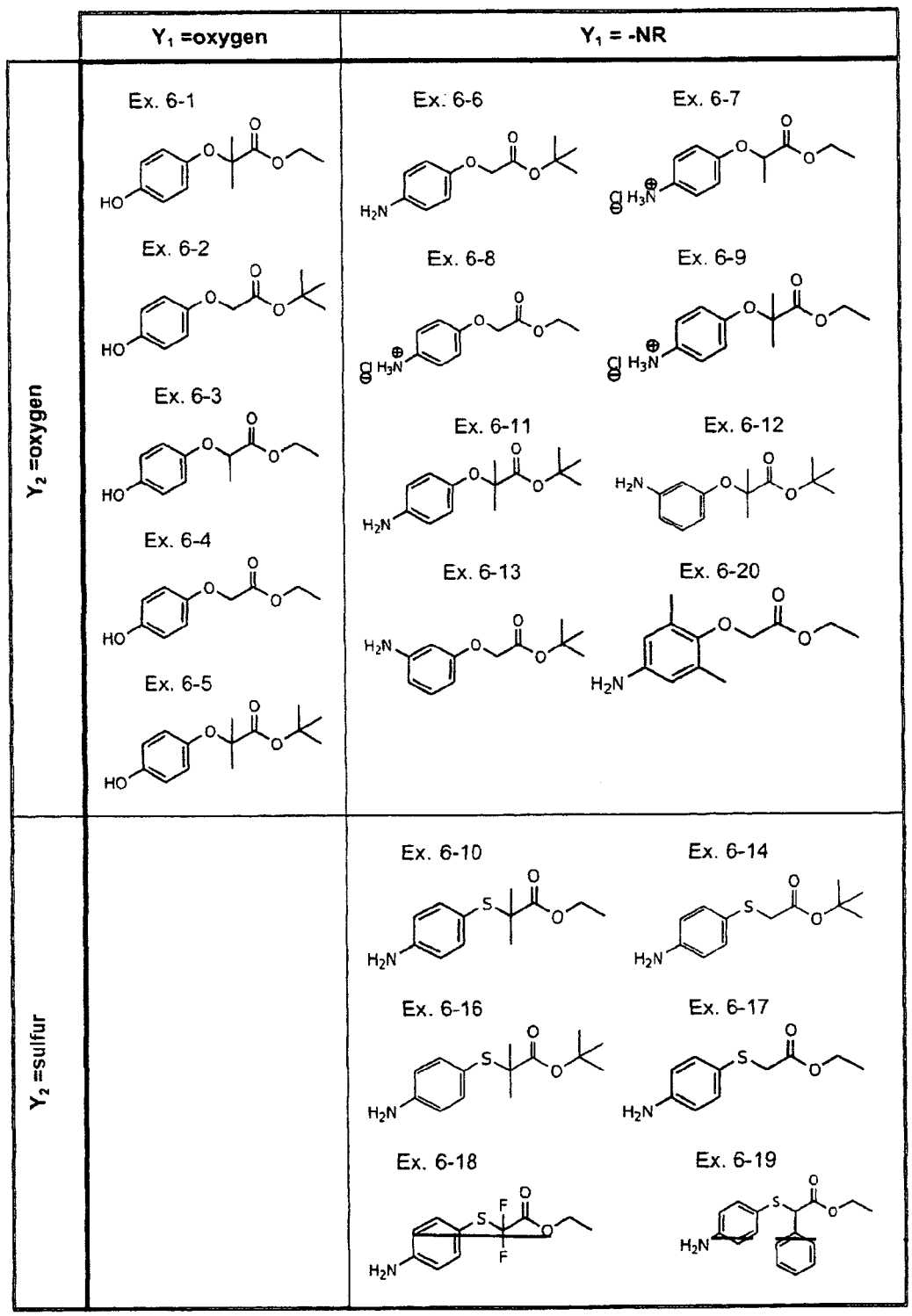
Figure 6G:
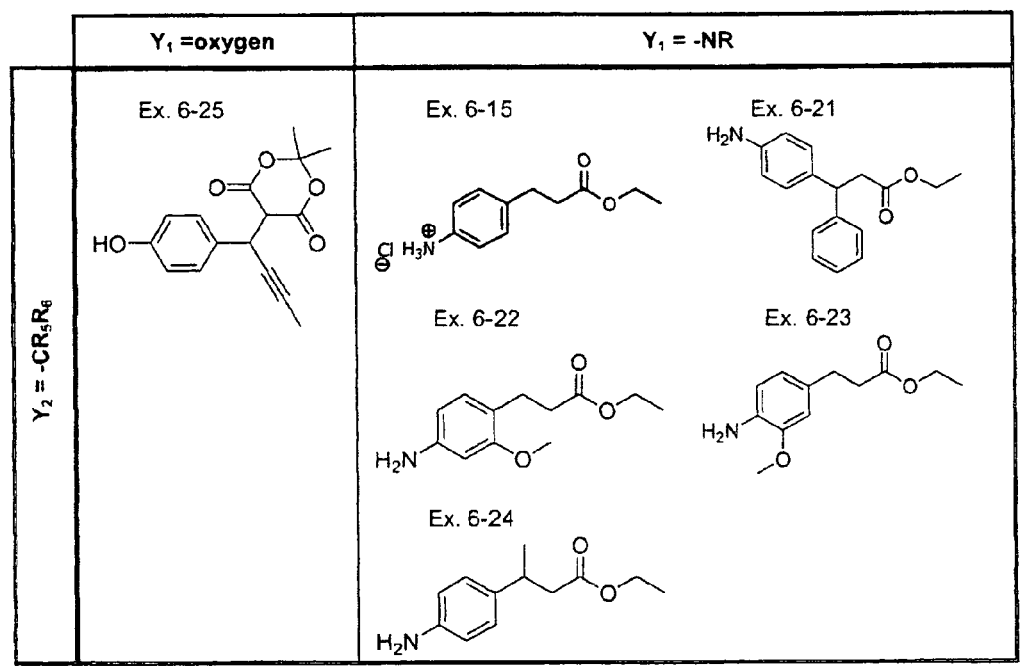

Synthesis of the intermediates in FIGS. 6a, 6c, and 6e requires 2 stages and is summarized in Table 6-1.

TABLE 6-1

| Ex. | No. and type of Stage (Protocol) | Details |
|---|---|---|
| 6-1 | Stage 1: Preparation of ethyl 2-(4-(benzyloxy)phenoxy)-2-methylpropanoate (Protocol SQ and PA) | Yield: 70%. Appearance: colorless oil. $^1$H NMR: 1.3 (t, 3H, J = 7.3 Hz); 1.56 (s, 6H); 4.26 (q, 2H, J = 7.3 Hz); 5.02 (s, 2H); 6.87 (s, 4H); 7.32-7.36 (m, 5H). |
|  | Stage 2: Obtaining ethyl 2-(4-hydroxyphenoxy)-2-methylpropanoate (Protocol SR) | Yield: 94%. Appearance: pink solid. $^1$H NMR: 1.29 (t, 3H, J = 7.0 Hz); 1.53 (s, 6H); 4.26 (q, 2H, J = 7.0 Hz); 6.70 (d, 2H, J = 9.0 Hz); 6.80 (d, 2H, J = 9.0 Hz). |
| 6-2 | Stage 1: Preparation of tert-butyl 2-(4-(benzyloxy)phenoxy)ethanoate (Protocol SQ) | Yield: quantitative. Appearance: colorless oil. $^1$H NMR: 1.5 (s, 9H); 4.48 (s, 2H); 5.03 (s, 2H); 6.84-6.94 (m, 4H); 7.33-7.46 (m, 5H). |
|  | Stage 2: Obtaining tert-butyl 2-(4-hydroxyphenoxy)ethanoate (Protocol SR and PD) | Yield: 97%. Appearance: white solid. $^1$H NMR: 1.48 (s, 9H); 4.47 (s, 2H); 6.75-6.83 (m, 4H). |
| 6-3 | Stage 1: Preparation of ethyl 2-(4-(benzyloxy)phenoxy)propanoate (Protocol SQ and PA) | Yield: 92%. Appearance: colorless oil. $^1$H NMR: 1.28 (t, 3H, J = 7.2 Hz); 1.63 (d, 3H, J = 6.9 Hz); 4.24 (q, 2H, J = 7.2 Hz); 4.68 (q, 1H, J = 6.9 Hz); 5.03 (s, 2H); 6.85-6.94 (m, 4H); 7.32-7.46 (m, 5H). |
|  | Stage 2: Obtaining ethyl 2-(4-hydroxyphenoxy)propanoate (Protocol SR and PA) | Yield: 86%. Appearance: yellow oil. $^1$H NMR: 1.26 (t, 3H, J = 7.0 Hz); 1.59 (d, 3H, J = 6.7 Hz); 4.23 (q, 2H, J = 7.3 Hz); 4.67 (q, 1H, J = 6.7 Hz); 6.71-6.78 (m, 4H). |
| 6-4 | Stage 1: Preparation of ethyl 2-(4-(benzyloxy)phenoxy)ethanoate (Protocol SQ and PA) | Yield: 80%. Appearance: white solid. $^1$H NMR: 1.32 (t, 3H, J = 7.0 Hz); 4.28 (q, 2H, J = 7.0 Hz); 4.59 (s, 2H); 5.03 (s, 2H); 6.86-6.95 (m, 4H); 7.28-7.50 (m, 5H). |
|  | Stage 2: Obtaining ethyl 2-(4-hydroxyphenoxy) ethanoate (Protocol SR) | Yield: 95%. Appearance: white solid. $^1$H NMR: 1.31 (t, 3H, J = 7.2 Hz); 4.28 (q, 2H, J = 7.2 Hz); 4.57 (s, 2H); 5.03 (s, 1H); 6.74-6.83 (m, 4H). |
| 6-5 | Stage 1: Preparation of tert-butyl 2-(4-(benzyloxy)phenoxy)2-methylpropanoate (Protocol SQ and PA) | Yield: 71%. Appearance: white solid. $^1$H NMR: 1.47 (s, 9H); 1.53 (s, 6H); 5.02 (s, 2H); 6.87 (s, 4H); 7.33-7.46 (m, 5H). |
|  | Stage 2: Obtaining tert-butyl 2-(4-hydroxyphenoxy)-2-methylpropanoate (Protocol SR and PA) | Yield: 64%. Appearance: white solid. $^1$H NMR: 1.48 (s, 9H); 1.52 (s, 6H); 3.80 (s, 1H); 6.69-6.73 (m, 2H); 6.78-6.83 (m, 2H). |
| 6-6 | Stage 1: Preparation of tert-butyl 2-(4-nitrophenoxy)ethanoate (Protocol SQ and PD) | Yield: 60%. Appearance: ochre solid. $^1$H NMR: 1.5 (s, 9H); 4.63 (s, 2H); 6.96 (d, 2H, J = 9.3 Hz); 8.22 (d, 2H, J = 9.3 Hz). |
|  | Stage 2: Obtaining tert-butyl 2-(4-aminophenoxy)ethanoate (Protocol SR) | Yield: quantitative. Appearance: pink/red solid $^1$H NMR: 1.49 (s, 9H); 3.35 (s (broad), 2H); 4.44 (s, 2H); 6.57 (d, 2H, J = 8.8 Hz); 6.76 (d, 2H, J = 8.8 Hz). |
| 6-7 | Stage 1: Preparation of ethyl 2-(4-(tertbutylcarbonylamino)phenoxy) propanoate (Protocol SQ and PD) | Yield: 80%. Appearance: white solid. $^1$H NMR: 1.26 (t, 3H, J = 7.3 Hz); 1.52 (s, 9H); 1.62 (d, 3H, J = 6.8 Hz); 4.21 (q, 2H, J = 7.3 Hz); 4.70 (q, 1H, J = 6.8 Hz); 6.37 (s (broad), 1H); 6.83 (d, 2H, J = 9.0 Hz); 7.26 (d, 2H, J = 9.0 Hz). |
|  | Stage 2: Obtaining ethyl 2-(4-aminophenoxy)propanoate hydrochloride (Protocol SS and PE) | Yield: 99%. Appearance: white solid. $^1$H NMR: 1.17 (t, 3H, J = 7.2 Hz); 1.15 (d, 3H, J = 6.7 Hz); 4.13 (q, 2H, J = 7.2 Hz); 4.99 (q, 1H, J = 6.7 Hz); 6.99 (d, 2H, J = 8.8 Hz); 7.31 (d, 2H, J = 8.8 Hz); 10.28 (s (broad), 3H). |
| 6-8 | Stage 1: Preparation of ethyl 2-(4-(tertbutylcarbonylamino)phenoxy) ethanoate (Protocol SQ) | Yield: quantitative. Appearance: white solid. $^1$H NMR: 1.29 (t, 3H, J = 7.0 Hz); 1.51 (s, 9H); 4.27 (q, 2H, J = 7.0 Hz); 4.59 (s, 2H); 6.44 (s (broad), 1H); 6.85 (d, 2H, J = 8.8 Hz); 7.28 (d, 2H, J = 8.8 Hz). |
|  | Stage 2: Obtaining ethyl 2-(4-aminophenoxy)ethanoate hydrochloride (Protocol SS and PE) | Yield: 86%. Appearance: pink solid $^1$H NMR: 1.20 (t, 3H, J = 7.0 Hz); 4.16 (q, 2H, J = 7.0 Hz); 4.81 (s, 2H); 7.03 (d, 2H, J = 8.8 Hz); 7.33 (d, 2H, J = 8.8 Hz); 10.26 (s (broad), 3H). |
| 6-9 | Stage 1: Preparation of ethyl 2-(4-(tertbutylcarbonylamino)phenoxy)-2-methyl-propanoate (Protocol SQ and PD) | Yield: 95%. Appearance: colorless oil. $^1$H NMR: 1.28 (t, 3H, J = 7.0 Hz); 1.52 (s, 9H); 1.56 (s, 6H); 4.23 (q, 2H, J = 7.0 Hz); 6.39 (s (broad), 1H); 6.83 (d, 2H, J = 9.0 Hz); 7.24 (d, 2H, J = 9.0 Hz). |

TABLE 6-1-continued

| Ex. | No. and type of Stage (Protocol) | Details |
|---|---|---|
| | Stage 2: Obtaining ethyl 2-(4-aminophenoxy)-2-methylpropanoate hydrochloride (Protocol SS and PE) | Yield: 89%. Appearance: white solid.<br>$^1$H NMR: 1.17 (t, 3H, J = 7.0 Hz); 1.53 (s, 6H); 4.15 (q, 2H, J = 7.0 Hz); 6.88 (d, 2H, J = 8.8 Hz); 7.29 (d, 2H, J = 8.8 Hz); 10.24 (s (broad), 3H). |
| 6-11 | Stage 1: Preparation of tert-butyl 2-(4-nitrophenoxy)-2-methylpropanoate (Protocol SQ and PA) | Yield: 65%. Appearance: yellow solid<br>$^1$H NMR: 1.43 (s, 9H); 1.65 (s, 6H); 6.86 (d, 2H, J = 7.3 Hz); 8.22 (d, 2H, J = 7.3 Hz). |
| | Stage 2: Obtaining tert-butyl 2-(4-aminophenoxy)-2-methylpropanoate (Protocol SR and PD) | Yield: 91%. Appearance: brown solid.<br>$^1$H NMR: 1.46 (s, 9H); 1.5 (s, 6H); 4.33 (s (broad), 2H); 6.69 (d, 2H, J = 8.8 Hz); 6.78 (d, 2H, J = 8.8 Hz). |
| 6-12 | Stage 1: Preparation of tert-butyl 2-(3-nitrophenoxy)-2-methylpropanoate (Protocol SQ and PA) | Yield: 11%. Appearance: green solid.<br>$^1$H NMR: 1.47 (s, 9H); 1.62 (s, 6H); 7.17-7.20 (m, 1H); 7.40 (t, 1H, J = 8.2 Hz); 7.68 (t, 1H, J = 2.3 Hz); 7.83-7.86 (m, 1H). |
| | Stage 2: Obtaining tert-butyl 2-(3-aminophenoxy)-2-methylpropanoate (Protocol SR and PD) | Yield: 37%. Appearance: green solid.<br>$^1$H NMR: 1.46 (s, 9H); 1.5 (s, 6H); 4.33 (s (broad), 2H); 6.69 (d, 2H, J = 8.8 Hz); 6.78 (d, 2H, J = 8.8 Hz). |
| 6-13 | Stage 1: Preparation of tert-butyl 2-(3-nitrophenoxy)ethanoate (Protocol SQ and PC) | Yield: 96%. Appearance: red-orange solid.<br>$^1$H NMR: 1.51 (s, 9H); 4.62 (s, 2H); 7.27 (dd, 1H, J = 2.0 Hz, J = 8.2 Hz); 7.46 (t, 1H, J = 8.2 Hz); 7.71 (t, 1H, J = 2.0 Hz); 7.88 (d, 1H, J = 8.2 Hz). |
| | Stage 2: Obtaining tert-butyl 2-(3-aminophenoxy)ethanoate (Protocol SR and PA) | Yield: 72%. Appearance: pink/red oil.<br>$^1$H NMR: 1.49 (s, 9H); 4.48 (s, 2H); 5.35 (s (broad), 2H); 6.48 (m, 3H); 7.12 (d, 2H, J = 7.9 Hz). |
| 6-20 | Stage 1: Preparation of ethyl 2-(4-nitro-2,6-dimethylphenoxy)ethanoate (Protocol SQ and PD) | Yield: 99%. Appearance: yellow solid.<br>$^1$H NMR: 1.34 (t, 3H, J = 7.0 Hz); 2.40 (s, 6H); 4.31 (q, 2H, J = 7.0 Hz); 4.47 (s, 2H); 7.93 (s, 2H). |
| | Stage 2: Obtaining ethyl 2-(4-amino-2,6-dimethylphenoxy)ethanoate (Protocol SR) | Yield: quantitative. Appearance: colorless oil.<br>$^1$H NMR: 1.33 (t, 3H, J = 7.0 Hz); 2.22 (s, 6H); 4.30 (q, 2H, J = 7.0 Hz); 4.33 (s, 2H); 6.34 (s, 2H). |
| 6-21 | Stage 1: Preparation of ethyl 3-(4-nitrophenyl)-3-phenylacrylate (Protocol ST and PD) | Yield: 57%. Appearance: yellow oil.<br>$^1$H NMR: 1.17 (t, 3H, J = 7.3 Hz); 4.08 (q, 2H, J = 7.3 Hz); 6.49 (s, 1H); 7.33-7.43 (m, 2H); 7.54 (t, 2H, J = 7.9 Hz); 7.64-7.69 (m, 1H); 7.95 (d, 2H, J = 8.8 Hz); 8.27 (d, 2H, J = 8.8 Hz). |
| | Stage 2: Obtaining ethyl 3-(4-aminophenyl)-3-phenylpropanoate (Protocol SR) | Yield: 53%. Appearance: colorless oil.<br>$^1$H NMR: 1.12 (t, 3H, J = 7.0 Hz); 2.99 (d, 2H, J = 8.2 Hz); 7.03 (q, 2H, J = 7.3 Hz); 4.45 (t, 1H, J = 7.9 Hz); 6.61 (d, 2H, J = 8.5 Hz); 7.02 (d, 2H, J = 8.5 Hz); 7.14-7.30 (m, 5H). |
| 6-22 | Stage 1: Preparation of ethyl 3-(2-methoxy-4-nitrophenyl)acrylate (Protocol ST and PA) | Yield: 20%. Appearance: yellow solid.<br>$^1$H NMR: 1.36 (t, 3H, J = 7.2 Hz); 4.01 (s, 3H); 4.30 (q, 2H, J = 7.2 Hz); 6.64 (d, 1H, J = 16.2 Hz); 7.63 (d, 1H, J = 8.5 Hz); 7.78 (d, 1H, J = 2.0 Hz); 7.85 (dd, 1H, J = 2.0 Hz J = 8.5 Hz); 7.95 (d, 1H, J = 16.2 Hz). |
| | Stage 2: Obtaining ethyl 3-(4-amino-2-methoxyphenyl)propanoate (Protocol SR) | Yield: 64%. Appearance: colorless oil.<br>$^1$H NMR: 1.25 (t, 3H, J = 7.0 Hz); 2.54 (t, 2H, J = 7.3 Hz); 2.83 (t, 2H, J = 7.3 Hz); 3.78 (s, 3H); 4.12 (q, 2H, J = 7.0 Hz); 6.20-6.24 (m, 2H); 6.92 (d, 1H, J = 8.8 Hz). |
| 6-23 | Stage 1: Preparation of ethyl 3-(3-methoxy-4-nitrophenyl)acrylate (Protocol ST and PA) | Yield: 43%. Appearance: yellow solid.<br>$^1$H NMR: 1.36 (t, 3H, J = 7.3 Hz); 4.00 (s, 3H); 4.30 (q, 2H, J = 7.3 Hz); 6.52 (d, 1H, J = 16.1 Hz); 7.18-7.21 (m, 2H); 7.65 (d, 1H, J = 16.1 Hz); 7.88 (d, 1H, J = 8.8 Hz). |
| | Stage 2: Obtaining ethyl 3-(4-amino-3-methoxyphenyl)propanoate (Protocol SR) | Yield: 99%. Appearance: colorless oil.<br>$^1$H NMR: 1.25 (t, 3H, J = 7.0 Hz); 2.58 (m, 2H); 2.87 (m, 2H); 3.84 (s, 3H); 4.13 (q, 2H, J = 7.0 Hz); 6.66-6.64 (m, 3H). |
| 6-24 | Stage 1: Preparation of ethyl 3-(4-nitrophenyl)but-2-enoate (Protocol SQ and PD) | Yield: 84%. Appearance: yellow solid.<br>$^1$H NMR: 1.34 (s, 3H, J = 7.2 Hz); 2.59 (d, 3H, J = 1.5 Hz); 4.24 (q, 2H, J = 7.2 Hz); 6.19 (d, 1H, J = 1.5 Hz); 7.62 (d, 2H, J = 8.9 Hz); 8.23 (d, 2H, J = 8.9 Hz). |
| | Stage 2: Obtaining ethyl 3-(4-aminophenyl)butanoate (Protocol SR) | Yield: 59%. Appearance: colorless oil<br>$^1$H NMR: 1.20 (t, 3H, J = 7.0 Hz); 1.26 (d, 3H, J = 7.0 Hz); 2.44-2.60 (m, 2H); 3.12-3.22 (m, 1H); 3.57 (m, 2H); 4.08 (q, 2H, J = 7.0 Hz); 6.64 (d, 2H, J = 8.3 Hz); 7.02 (d, 2H, J = 8.3 Hz). |

Synthesis of the intermediates in FIGS. 6b and 6d requires a single stage and it is summarized in Table 6-2.

TABLE 6-2

| Ex. | Intermediates (Protocol) | Details |
|---|---|---|
| 6-10 | Ethyl 2-(4-aminophenylthio)-2-methylpropanoate (Protocol SQ and PA) | Yield: 87%. Appearance: colorless oil.<br>$^1$H NMR: 1.13 (t, 3H, J = 7.1 Hz); 1.33 (s, 6H); 4.00 (q, 2H, J = 7.1 Hz); 5.47 (s, 2H); 6.51 (d, 2H, J = 8.5 Hz); 7.04 (d, 2H, J = 8.5 Hz). |
| 6-14 | Tert-butyl 2-(4-aminophenylthio)acetate (Protocol SQ and PA) | Yield: 28%. Appearance: yellow oil.<br>$^1$H NMR: 1.40 (s, 9H); 3.37 (s, 2H); 3.77 (s(broad), 2H); 6.59 (d, 2H, J = 8.5 Hz); 7.28 (d, 2H, J = 8.5 Hz). |
| 6-15 | Ethyl 3-(4-aminophenyl)propanoate hydrochloride (Protocol SS and PE) | Yield: 86%. Appearance: white solid.<br>$^1$H NMR: 1.12 (t, 3H, J = 7.3 Hz); 2.60 (t, 2H, J = 7.3 Hz); 2.85 (t, 2H, J = 7.3 Hz); 4.00 (q, 2H, J = 7.3 Hz); 7.27 (d, 2H, J = 8.2 Hz); 7.33 (d, 2H, J = 8.2 Hz). |
| 6-16 | Tert-butyl 2-(4-aminophenylthio)-2-methylpropanoate (Protocol SQ and PA) | Yield: 79%. Appearance: white solid.<br>$^1$H NMR: 1.39 (s, 6H); 1.43 (s, 9H); 3.81 (s(broad), 2H); 6.60 (d, 2H, J = 8.5 Hz); 7.28 (d, 2H, J = 8.5 Hz). |
| 6-17 | Ethyl 2-((4 amino)phenylthio)ethanoate (Protocol SQ and PA) | Yield: 41%. Appearance: colorless oil.<br>$^1$H NMR: 1.21 (t, 3H, J = 7.2 Hz); 3.45 (s, 2H); 3.75 (s, 2H); 4.13 (q, 2H, J = 7.2 Hz); 6.61 (d, 2H, J = 8.5 Hz); 7.29 (d, 2H, J = 8.5 Hz) |
| 6-18 | Ethyl 2-(4-aminophenylthio)-2,2-difluoroacetate (Protocol SQ and PA) | Yield: 29%. Appearance: colorless oil<br>$^1$H NMR: 1.29 (t, 3H, J = 7.0 Hz); 4.26 (q, 2H, J = 7.0 Hz); 6.66 (d, 2H, J = 8.8 Hz); 7.37 (d, 2H, J = 8.5 Hz). |
| 6-19 | Ethyl 2-(4-aminophenylthio)-2-phenylethanoate (Protocol SQ and PA) | Yield: 37%. Appearance: yellow oil.<br>$^1$H NMR: 1.18 (t, 3H, J = 7.3 Hz); 3.75 (s (broad), 2H); 4.06-4.18 (m, 2H); 4.73 (s, 1H); 6.54 (d, 2H, J = 8.8 Hz); 7.21 (d, 2H, J = 8.5 Hz); 7.27-7.34 (m, 3H); 7.41-7.44 (m, 2H). |

For Example 6-25 (5-(1-(4-hydroxyphenyl)but-2-ynyl)-2,2-dimethyl-1,3-dioxane-4,6-dione), synthesis of this compound requires 2 stages. In the first (preparation of 5-(4-hydroxybenzylidene)-2,2-dimethyl-1,3-dioxane-4,6-dione), a solution of 4-hydroxybenzaldehyde in water (1 mol/L) is heated to 75° C. Meldrum's acid (1.05 eq.) is added in portions, then the reaction mixture is stirred at 75° C. for 2 hours. The reaction mixture is cooled and stirred for 2 hours at 0° C. The precipitate is drained, then washed with ice water and heptane (Yield: 90%; Appearance: yellow solid; $^1$H NMR: 1.80 (s, 6H); 6.94 (d, 2H, J=8.8 Hz); 8.19 (d, 2H, J=8.8 Hz); 8.39 (s, 1H)). In the second (obtaining 5-(1-(4-hydroxyphenyl)but-2-ynyl)-2,2-dimethyl-1,3-dioxane-4,6-dione), a solution of the preceding intermediate in tetrahydrofuran (0.5 mol/L) is added under inert atmosphere, dropwise (0.25 hours), to a solution of 1-propylmagnesium bromide in tetrahydrofuran (0.5 mol/L, 2 eq.). After stirring for 0.25 hours at room temperature, the reaction mixture is diluted with aqueous solution of ammonium chloride (0.6 N, 3 eq.), extracted with cyclohexane, and acidified (pH=2) with sodium bisulfate. The evaporation residue is used without other forms of purification (Yield: 98%; Appearance: yellow solid; $^1$H NMR: 1.64 (s, 3H); 1.82 (s, 3H); 1.83 (s, 3H); 4.46 (d, 1H, J=2.6 Hz); 4.73 (d, 1H, J=2.6 Hz); 6.76 (d, 2H, J=8.5 Hz); 7.39 (d, 2H, J=8.5 Hz); 8.24 (s, 1H)).

Example 7

Synthesis of the Compounds According to the Invention

Synthesis of the compounds according to the invention in FIG. 7a requires 2 or 3 stages and is summarized in Table 7-1.

TABLE 7-1

| Cpd | No. and type of Stage (Ex.; Protocol) | Details |
|---|---|---|
| 4 | 1: Preparation of tert-butyl 2-(4-((2-methoxy-6-phenylpyridin-3-yl)methylamino)-phenoxy)ethanoate (Ex. 5-1 and Ex. 6-6 with Protocol SX and PA) | Yield: quantitative. Appearance: yellow oil<br>$^1$H NMR: 1.49 (s, 9H); 4.11 (s, 3H); 4.30 (s, 2H); 4.43 (s, 2H); 6.61 (d, 2H, J = 8.8 Hz); 6.78 (d, 2H, J = 8.8 Hz); 7.31 (d, 1H, J = 7.6 Hz); 7.34-7.49 (m, 3H); 7.61 (d, 1H, J = 7.6 Hz); 8.02 (m, 2H). |
|  | 2: Obtaining 2-(4-(((2-methoxy-6-phenylpyridin-3yl)methyl)amino)phenoxy)ethanoic acid (Protocol SW and PE) | Yield: 81%. Appearance: white solid<br>$^1$H NMR: 4.03 (s, 3H); 4.18 (s, 2H); 4.47 (s, 2H); 6.50 (d, 2H, J = 8.8 Hz); 6.68 (d, 2H, J = 8.8 Hz); 7.55-7.35 (m, 4H); 7.64 (d, 1H, J = 7.6 Hz); 8.06 (m, 2H). |
| 8 | 1: Preparation of ethyl 2-(4-((2-tert-butoxy-6-phenylpyridin-3-yl)methylamino)-phenoxy)ethanoate (Ex. 5-2 and Ex. 6-8 with Protocol SX and PA) | Yield: 51%. Appearance: white solid<br>$^1$H NMR: 1.29 (t, 3H, J = 7.0 Hz); 1.71 (s, 9H); 4.23-4.29 (m, 4H); 4.53 (s, 2H); 6.64 (d, 2H, J = 9.1 Hz); 6.80 (d, 2H, J = 9.1 Hz); 7.27 (d, 1H, J = 7.6 Hz); 7.35-7.47 (m, 3H); 7.57 (d, 1H, J = 7.6 Hz); 8.0 (d, 2H, J = 7.3 Hz). |

TABLE 7-1-continued

| Cpd No. | and type of Stage (Ex.; Protocol) | Details |
|---|---|---|
| | 2: Obtaining 2-(4-((2-tert-butyloxy-6-phenylpyridin-3-yl)methyl)amino)phenoxy)ethanoic acid (Protocol SU and PA) | Yield: 63%. Appearance: white solid.<br>$^1$H NMR: 1.67 (s, 9H); 4.12 (s, 2H); 4.43 (s, 2H); 6.48 (d, 2H, J = 9.1 Hz); 6.67 (d, 2H, J = 9.1 Hz); 7.35-7.49 (m, 4H); 7.60 (d, 1H, J = 7.9 Hz); 7.99 (d, 2H, J = 7.3 Hz). |
| 9 | 1: Preparation of ethyl 2-(4-((2-tert-butoxy-6-phenylpyridin-3-yl)methylamino)-phenoxy)-2-methyl-propanoate (Ex. 5-2 and Ex. 6-9 with Protocol SX and PA) | Yield: 79%. Appearance: orange-colored oil.<br>$^1$H NMR: 1.28 (t, 3H, J = 7.3 Hz); 1.52 (s, 6H); 1.71 (s, 9H); 4.19-4.26 (m, 4H); 6.55 (d, 2H, J = 9.0 Hz); 6.77 (d, 2H, J = 9.0 Hz); 7.27 (d, 1H, J = 7.6 Hz); 7.35-7.48 (m, 3H); 7.56 (d, 1H, J = 7.6 Hz); 7.99 (d, 2H, J = 7.7 Hz). |
| | 2: Obtaining 2-(4-(((2-tert-butyloxy-6-phenylpyridin-3-yl)methyl)amino)phenoxy)-2-methyl-propanoic acid (Protocol SU and PD) | Yield: 46%. Appearance: yellow solid.<br>$^1$H NMR: 1.36 (s, 6H); 1.66 (s, 9H); 4.11 (s, 2H); 6.46 (d, 2H, J = 8.8 Hz); 6.67 (d, 2H, J = 8.8 Hz); 7.35-7.49 (m, 4H); 7.61 (d, 1H, J = 7.6 Hz); 8.0 (d, 2H, J = 7.0 Hz). |
| 10 | 1: Preparation of ethyl 2-(4-((2-tert-butoxy-6-phenylpyridin-3-yl)methylamino)-phenoxy)propanoate (Ex. 5-2 and Ex. 6-7 with Protocol SX and PA) | Yield: 52%. Appearance: yellow oil.<br>$^1$H NMR: 1.24 (t, 3H, J = 7.3 Hz); 1.57 (d, 3H, J = 6.7 Hz); 1.71 (s, 9H); 4.17-4.23 (m, 4H); 4.61 (q, 1H, J = 6.7 Hz); 6.60 (d, 2H, J = 9.0 Hz); 6.77 (d, 2H, J = 9.0 Hz); 7.26 (d, 1H, J = 7.6 Hz); 7.37-7.47 (m, 3H); 7.56 (d, 1H, J = 7.6 Hz); 7.99 (d, 2H, J = 7.0 Hz). |
| | 2: Obtaining 2-(4-(((2-tert-butyloxy-6-phenylpyridin-3-yl)methyl)amino)phenoxy)propanoic acid (Protocol SU and PA) | Yield: 18%. Appearance: white solid.<br>$^1$H NMR: 1.4 (d, 3H, J = 6.7 Hz); 1.66 (s, 9 Hz); 4.11 (s, 2H); 4.50-4.57 (m, 1H); 6.48 (d, 2H, J = 8.8 Hz); 6.64 (d, 2H, J = 8.8 Hz); 7.35-7.40 (m, 1H); 7.44-7.49 (m, 3H); 7.6 (d, 1H, J = 7.6 Hz); 7.99 (d, 2H, J = 7.3 Hz). |
| 11 | 1: Preparation of ethyl 2-(4-((2-methoxy-6-phenylpyridin-3-yl)methylamino)phenylthio)-2-methyl-propanoate (Ex. 5-1 and Ex. 6-10 with Protocol SX and PA) | Yield: 87%. Appearance: orange-colored oil<br>$^1$H NMR: 1.22 (t, 3H, J = 7.3 Hz); 1.45 (s, 6H); 4.04-4.16 (m, 5H); 4.35 (s, 2H); 6.56 (d, 2H, J = 8.5 Hz); 7.26 (d, 2H, J = 8.5 Hz); 7.31 (d, 1H, J = 7.6 Hz); 7.37-7.51 (m, 3H); 7.59 (d, 1H, J = 7.6 Hz); 8.19 (d, 2H, J = 8.5 Hz). |
| | 2: Obtaining 2-(4-(((2-methoxy-6-phenylpyridin-3-yl)methyl)amino)phenylthio)-2-methyl-propanoic acid (Protocol SU and PA) | Yield: 57%. Appearance: beige solid<br>$^1$H NMR: 1.29 (s, 6H); 4.04 (s, 3H); 4.24 (d, 2H, J = 5.8 Hz); 6.54 (m, 3H); 7.14 (d, 2H, J = 8.5 Hz); 7.37-7.54 (m, 4H); 7.64 (d, 1H, J = 7.6 Hz); 8.08 (d, 2H, J = 7.0 Hz), 12.34 (s, 1H). |
| 12 | 1: Preparation of tert-butyl 2-(4-((2-methoxy-6-phenylpyridin-3-yl)methylamino)phenoxy)-2-methyl-propanoate (Ex. 5-1 and Ex. 6-11 with Protocol SX and PA) | Yield: 71%. Appearance: yellow oil.<br>$^1$H NMR: 1.44 (s, 9H); 1.49 (s, 6H); 4.09 (s, 3H); 4.32 (s, 2H); 6.61-6.72 (m, 2H); 6.79 (d, 2H, J = 9.1 Hz); 7.30 (d, 1H, J = 7.6 Hz); 7.36-7.48 (m, 3H); 7.62-7.65 (m, 1H); 8.03 (d, 2H, J = 8.2 Hz). |
| | 2: Obtaining 2-(4-(((2-methoxy-6-phenylpyridin-3-yl)methyl)amino)phenoxy)-2-methyl-propanoic acid (Protocol SW and PC) | Yield: 70%. Appearance: white solid<br>$^1$H NMR: 1.36 (s, 6H); 4.03 (s, 3H); 4.17 (s, 2H); 5.89 (s(broad), 1H); 6.47 (d, 2H, J = 9.1 Hz); 6.67 (d, 2H, J = 9.1 Hz); 7.37-7.54 (m, 4H); 7.66 (d, 1H, J = 7.6 Hz); 8.07 (d, 2H, J = 7.0 Hz). |
| 16 | 1: Preparation of tert-butyl 2-(4-((2-methoxy-6-phenylpyridin-3-yl)methylamino)-phenylthio)ethanoate (Ex. 5-1 and Ex. 6-14 with Protocol SX and PA) | Yield: 99%. Appearance: yellow oil.<br>$^1$H NMR: 1.40 (s, 9H); 3.38 (s, 2H); 4.12 (s, 3H); 4.34 (s, 2H); 6.58 (d, 2H, J = 8.8 Hz); 7.29-7.31 (m, 3H); 7.37-7.48 (m, 3H); 7.58 (d, 1H, J = 7.6 Hz); 8.04 (d, 2H, J = 8.5 Hz). |
| | 2: Obtaining 2-(4-(((2-methoxy-6-phenylpyridin-3-yl)methyl)amino)phenylthio)ethanoic acid (Protocol SW and PC) | Yield: 64%. Appearance: white solid<br>$^1$H NMR: 3.49 (s, 2H); 4.11 (s, 3H); 4.34 (s, 2H); 6.58 (d, 2H, J = 8.0 Hz); 7.30-7.48 (m, 6H); 7.58 (d, 1H, J = 7.1 Hz); 8.03 (d, 2H, J = 8.0 Hz). |
| 19 | 1: Preparation of ethyl 3-(4-((2-methoxy-6-phenylpyridin-3-yl)methylamino)phenyl)propanoate (Ex. 5-1 and Ex. 6-15 with Protocol SX and PA) | Yield: 53%. Appearance: yellow oil.<br>$^1$H NMR: 1.24 (t, 3H, J = 7.3 Hz); 2.56 (t, 2H, J = 8.2 Hz); 2.84 (t, 2H, J = 8.2 Hz); 4.09-4.16 (m, 5H); 4.33 (s, 2H); 6.64 (d, 2H, J = 8.2 Hz); 7.03 (d, 2H, J = 8.2 Hz); 7.30 (d, 1H, J = 7.6 Hz); 7.36-7.48 (m, 3H); 7.63 (d, 1H, J = 7.6 Hz); 8.04 (d, 2H, J = 7.3 Hz). |
| | 2: Obtaining 3-(4-(((2-methoxy-6-phenylpyridin-3-yl)methyl)amino)phenyl) propanoic acid (Protocol SU and PC) | Yield: 73%. Appearance: yellow solid.<br>$^1$H NMR: 2.62 (t, 2H, J = 7.6 Hz); 2.85 (t, 2H, J = 7.6 Hz); 4.10 (s, 3H); 4.34 (s, 2H); 6.66 (d, 2H, J = 8.2 Hz); 7.03 (d, 2H, J = 8.2 Hz); 7.30 (d, 1H, J = 7.6 Hz); 7.36-7.48 (m, 3H); 7.63 (d, 1H, J = 7.6 Hz); 8.04 (m, 2H). |
| 22 | 1: Preparation of tert-butyl 2-(4-((2-methoxy-6-(4-(trifluoromethyl)phenyl)pyridin-3-yl)methylamino)phenylthio)-2-methylpropanoate (Ex. 5-3 and Ex. 6-16 with Protocol SX and PA) | Yield: 92%; Appearance: yellow oil;<br>$^1$H NMR: 1.39 (s, 6H); 1.43 (s, 9H); 4.12 (s, 3H); 4.37 (s, 2H); 6.56 (d, 2H, J = 8.5 Hz); 7.30 (d, 2H, J = 8.5 Hz); 7.34 (d, 1H, J = 7.6 Hz); 7.62 (d, 1H, J = 7.6 Hz); 7.71 (d, 2H, J = 8.2 Hz); 8.50 (d, 2H, J = 8.2 Hz). |

TABLE 7-1-continued

| Cpd | No. and type of Stage (Ex.; Protocol) | Details |
|---|---|---|
|  | 2: Obtaining 2-(4-(((2-methoxy-6-(4-(trifluoromethyl)phenyl)pyridin-3-yl)methyl)amino)phenylthio)-2-methylpropanoic acid (Protocol SW and PB) | Yield: 55%; Appearance: yellow solid.<br>$^1$H NMR: 1.47 (s, 6H); 4.11 (s, 3H); 4.36 (s, 2H); 6.57 (d, 2H, J = 8.8 Hz); 7.3-7.35 (m, 3H); 7.61 (d, 1H, J = 7.6 Hz); 7.69 (d, 2H, J = 8.0 Hz); 8.12 (d, 2H, J = 8.0 Hz |
| 23 | 1: Preparation of tert-butyl 2-(4-((2-methoxy-6-(4-(trifluoromethyl)phenyl)pyridin-3-yl)methylamino)phenylthio)ethanoate (Ex. 5-3 and Ex. 6-14 with Protocol SX and PA) | Yield: 96%. Appearance: yellow-orange oil.<br>$^1$H NMR: 1.41 (s, 9H); 3.37 (s, 2H); 4.12 (s, 3H); 4.42 (s, 2H); 6.57 (d, 2H, J = 8.6 Hz); 7.30-7.35 (m, 3H); 7.62 (d, 1H, J = 7.6 Hz); 7.71 (d, 2H, J = 8.5 Hz); 8.14 (d, 2H, J = 7.9 Hz). |
|  | 2: Obtaining 2-(4-(((2-methoxy-6-(4-(trifluoromethyl)phenyl)pyridin-3-yl)methyl)amino)phenylthio)ethanoic acid (Protocol SW and PB) | Yield: 21%. Appearance: yellow solid.<br>$^1$H NMR: 3.50 (s, 2H); 4.12 (s, 3H); 4.36 (s, 2H); 6.58 (d, 2H, J = 8.8 Hz); 7.32-7.36 (m, 3H); 7.61 (d, 1H, J = 7.6 Hz); 7.70 (d, 2H, J = 8.2 Hz); 8.14 (d, 2H, J = 8.2 Hz). |
| 26 | 1: Preparation of ethyl 2-(4-((2-methoxy-5-phenylpyridin-3-yl)methylamino)-phenylthio)ethanoate (Ex. 5-4 and Ex. 6-17 with Protocol SX and PA) | Yield: 73%. Appearance: yellow oil<br>$^1$H NMR: 1.19 (t, 3H, J = 7.3 Hz); 3.48 (s, 2H); 4.03 (s, 3H); 4.12 (q, 2H, J = 7.3 Hz); 4.37 (s, 2H); 6.77 (d, 2H, J = 7.9 Hz); 7.29-7.50 (m, 8H); 7.84 (d, 1H, J = 2.0 Hz); 8.30 (d, 1H, J = 2.0 Hz). |
|  | 2: Obtaining 2-(4-(((2-methoxy-5-phenylpyridin-3-yl)methyl)amino)phenylthio) ethanoic acid (Protocol SU and PE) | Yield: 66%. Appearance: white solid.<br>$^1$H NMR: 3.44 (s, 2H); 3.97 (s, 3H); 4.24 (d, 2H, J = 5.0 Hz); 6.39 (s broad, 1H); 6.56 (d, 2H, J = 8.6 Hz); 7.17 (d, 2H, J = 8.6 Hz); 7.31-7.37 (m, 1H); 7.41-7.46 (m, 2H); 7.54 (d, 2H, J = 7.3 Hz); 7.86 (d, 1H, J = 2.3 Hz); 8.36 (d, 1H, J = 2.3 Hz); 12.44 (s, 1H). |
| 27 | 1: Preparation of ethyl 2-(4-((2-methoxy-6-phenylpyridin-3-yl)methylamino)phenylthio)-2-2-difluoroethanoate (Ex. 5-1 and Ex. 6-18 with Protocol SX and PA) | Yield: 88%. Appearance: yellow oil.<br>$^1$H NMR: 1.26 (t, 3H, J = 7.3 Hz); 4.11 (s, 3H); 4.24 (q, 2H, J = 7.3 Hz); 4.37 (s, 2H); 6.65 (d, 2H, J = 8.8 Hz); 7.32 (d, 1H, J = 7.6 Hz); 7.38-7.49 (m, 5H); 7.58 (d, 1H, J = 7.3 Hz); 8.04 (d, 2H, J = 7.0 Hz). |
|  | 2: Obtaining 2-(4-(((2-methoxy-6-phenylpyridin-3-yl)-methyl)amino)phenylthio)-2,2-difluoro-ethanoic acid (Protocol SU and PC) | Yield: 36%. Appearance: white solid.<br>$^1$H NMR: 4.04 (s, 3H); 4.27 (s, 2H); 6.62 (d, 2H, J = 8.5 Hz); 7.26 (d, 2H, J = 8.5 Hz); 7.37-7.54 (m, 4H); 7.62 (d, 1H, J = 7.6 Hz); 8.07 (d, 2H, J = 7.3 Hz). |
| 28 | 1: Preparation of ethyl 2-(4-((2-methoxy-5-6-diphenylpyridin-3-yl)methylamino)-phenylthio)ethanoate (Ex. 5-5 and Ex. 6-17 with Protocol SX and PA) | Yield: 73%. Appearance: colorless oil.<br>$^1$H NMR: 1.19 (t, 3H, J = 7.0 Hz); 3.46 (s, 2H); 4.08 (s, 3H); 4.12 (q, 2H, J = 7.0 Hz); 4.38 (s, 2H); 6.66 (d, 2H, J = 8.5 Hz); 7.09-7.12 (m, 2H); 7.18-7.25 (m, 6H); 7.34 (d, 2H, J = 8.8 Hz); 7.37-7.40 (m, 2H); 7.59 (s, 1H). |
|  | 2: Obtaining 2-(4-(((2-methoxy-5,6-diphenylpyridin-3-yl)methyl)amino)phenylthio)ethanoic acid (Protocol SU and PA)<br>3: Protocol PC | Yield: 6.56%. Appearance: white solid.<br>$^1$H NMR: 3.38 (s, 2H); 4.00 (s, 3H); 4.26 (d, 2H, J = 5.6 Hz); 6.31 (m, 1H); 6.55 (d, 2H, J = 8.5 Hz); 7.05 (dd, 2H, J = 2.3 Hz J = 7.9 Hz); 7.13 (d, 2H, J = 8.5 Hz); 7.23-7.32 (m, 8H); 7.59 (s, 1H). |
| 29 | 1: Preparation of ethyl 2-(4-((2-methoxy-5-6-diphenylpyridin-3-yl)methyl amino)-phenylthio)ethanoate (Ex. 5-6 and Ex. 6-17 with Protocol SX and PA) | Yield: 58%. Appearance: colorless oil.<br>$^1$H NMR: 1.23 (t, 3H, J = 7.1 Hz); 3.50 (s, 2H); 4.00 (s, 3H); 4.15 (q, 2H, J = 7.1 Hz); 4.34 (s, 2H); 6.72 (m, 2H); 7.31-7.46 (m, 5H); 7.74-7.87 (m, 3H). |
|  | 2: Obtaining 2-(4-(((2-methoxy-5-bromo-6-phenylpyridin-3-yl)methyl)amino) phenylthio)-ethanoic acid (Protocol SU and PA)<br>3: Protocol PC | Yield: 34%. Appearance: white solid.<br>$^1$H NMR: 3.46 (s, 2H); 3.93 (s, 3H); 4.22 (d, 2H, J = 5.8 Hz); 6.45 (t, 1H, J = 5.8 Hz); 6.56 (d, 2H, J = 8.6 Hz); 7.19 (d, 2H, J = 8.6 Hz); 7.42-7.50 (m, 3H); 7.67 (m, 2H); 7.80 (s, 1H); 12.51 (s, 1H). |
| 30 | 1: Preparation of ethyl 2-(4-((2-methoxy-6-furylpyridin-3-yl)methylamino)-phenylthio)ethanoate (Ex. 5-e and Ex. 6-17 with Protocol SX and PA) | Yield: 85%. Appearance: yellow oil.<br>$^1$H NMR: 1.21 (t, 3H, J = 7.0 Hz); 3.49 (s, 2H); 4.02 (s, 3H); 4.15 (q, 2H, J = 7.0 Hz); 4.32 (s, 2H); 6.50-6.53 (m, 1H); 6.76 (d, 2H, J = 8.6 Hz); 7.00 (d, 1H, J = 2.9 Hz); 7.20 (d, 1H, J = 7.6 Hz); 7.31 (d, 2H, J = 8.6 Hz); 7.49-7.54 (m, 1H); 7.60 (d, 1H, J = 7.6 Hz). |
|  | 2: Obtaining 2-(4-(((2-methoxy-6-furylpyridin-3-yl)methyl)amino)phenylthio)ethanoic acid (Protocol SU and PC) | Yield: 57%. Appearance: beige solid.<br>$^1$H NMR: 3.44 (s, 2H); 3.98 (s, 3H); 4.19 (d, 2H, J = 5.6 Hz); 6.39 (t, 1H, J = 5.6 Hz); 6.51 (d, 2H, J = 8.8 Hz); 6.61-6.63 (m, 1H); 7.02 (d, 1H, J = 3.2 Hz); 7.16 (d, 2H, J = 8.8 Hz); 7.28 (d, 1H, J = 7.6 Hz); 7.59 (d, 1H, J = 7.6 Hz); 7.78 (m, 1H). |
| 31 | 1: Preparation of ethyl 3-(4-((2-methoxy-6-furylpyridin-3-yl)methylamino)-phenyl)propanoate (Ex. 5-6 and Ex. 6-15 with Protocol SX and PA) | Yield: 68%. Appearance: yellow oil.<br>$^1$H NMR: 1.13 (t, 3H, J = 7.1 Hz); 2.46 (t, 2H, J = 7.3 Hz); 2.66 (t, 2H, J = 7.3 Hz); 3.99 (s, 3H); 4.00 (q, 2H, J = 7.1 Hz); 4.17 (d, 2H, J = 6.0 Hz); 6.03 (t, 1H, J = 6.0 Hz); 6.46 (d, 2H, J = 8.3 Hz); 6.61-6.63 (m, 1H); 6.90 (d, 2H, J = 8.3 Hz); 7.02 (d, 1H, J = 3.2 Hz); 7.26 (d, 1H, J = 7.6 Hz); 7.59 (d, 1H, J = 7.6 Hz); 7.79 (s, 1H). |

TABLE 7-1-continued

| Cpd | No. and type of Stage (Ex.; Protocol) | Details |
|---|---|---|
| | 2: Obtaining 3-(4-(((2-methoxy-6-furylpyridin-3-yl)methyl)amino)phenyl)propanoic acid (Protocol SU and PC) | Yield: 24%. Appearance: beige solid.<br>¹H NMR: 2.41 (t, 2H, J = 7.6 Hz); 2.64 (t, 2H, J = 7.6 Hz); 3.99 (s, 3H); 4.17 (s, 2H); 6.03 (s (broad), 1H); 6.47 (d, 2H, J = 8.2 Hz); 6.63 (m, 1H); 6.91 (d, 2H, J = 8.2 Hz); 7.03 (d, 1H, J = 3.2 Hz); 7.26 (d, 1H, J = 7.6 Hz); 7.60 (d, 1H, J = 7.6 Hz); 7.79 (s, 1H). |
| 32 | 1: Preparation of ethyl 2-(4-((2-methoxy-6-phenylpyridin-3-yl)methylamino)-phenylthio)-2-phenylethanoate (Ex. 5-1 and Ex. 6-19 with Protocol SX and PA) | Yield: 75%. Appearance: yellow oil.<br>¹H NMR: 1.16 (t, 3H, J = 7.0 Hz); 4.05-4.20 (m, 5H); 4.33 (s, 2H); 4.69 (s, 1H); 6.53 (d, 2H, J = 8.6 Hz); 7.22 (d, 2H, J = 8.6 Hz); 7.28-7.33 (m, 4H); 7.39-7.49 (m, 5H); 7.56 (d, 1H, J = 7.6 Hz); 8.02-8.05 (m, 2H). |
| | 2: Obtaining 2-(4-(((2-methoxy-6-phenylpyridin-3-yl)methyl)amino)phenylthio)-2-phenyl-ethanoic acid (Protocol SU and PA)<br>3: Protocol PC | Yield: 58%. Appearance: white solid.<br>¹H NMR: 4.03 (s, 3H); 4.21 (d, 2H, J = 5.6 Hz); 4.71 (s, 1H); 6.43-6.48 (m, 3H); 7.07 (d, 2H, J = 8.8 Hz); 7.25-7.59 (m, 10H); 8.07 (d, 2H, J = 7.0 Hz). |
| 35 | 1: Preparation of ethyl 2-(4-((2-methoxy-6-phenylpyridin-3-yl)methylamino)-2,6-dimethyl-phenoxy)ethanoate (Ex. 5-1 and Ex. 6-20 with Protocol SX and PA) | Yield: 96%. Appearance: yellow oil.<br>¹H NMR (300 MHz, CDCl3, d in ppm): 1.33 (t, 3H, J = 7.0 Hz); 2.23 (s, 6H); 4.11 (s, 3H); 4.26-4.34 (m, 6H); 6.31 (s, 2H); 7.32 (d, 1H, J = 7.6 Hz); 7.38-7.48 (m, 3H); 7.61 (d, 1H, J = 7.6 Hz); 8.03-8.07 (d, 2H, J = 7.0 Hz). |
| | 2: Obtaining 2-(4-(((2-methoxy-6-phenylpyridin-3-yl)methyl)amino)-2,6-dimethyl-phenoxy) ethanoic acid (Protocol SU and PA) | Yield: 6%. Appearance: white solid.<br>¹H NMR: 2.08 (s, 6H); 4.03 (s, 3H); 4.15 (m, 4H); 6.21 (s, 2H); 7.36-7.54 (m, 4H); 7.63 (d, 1H, J = 7.6 Hz); 8.06-8.09 (m, 2H). |
| 36 | 1: Preparation of ethyl 3-(4-((2-methoxy-6-(4-(trifluoromethyl)phenyl)pyridin-3-yl)methylamino)phenyl)propanoate (Ex. 5-3 and Ex. 6-15 with Protocol SX and PA) | Yield: 43%. Appearance: orange-colored oil.<br>¹H NMR: 1.24 (t, 3H, J = 7.1 Hz); 2.56 (t, 2H, J = 7.5 Hz); 2.85 (t, 2H, J = 7.5 Hz); 4.09 (s, 3H); 4.12 (q, 2H, J = 7.1 Hz); 4.37 (s, 2H); 6.73-6.94 (m, 2H); 7.05 (d, 2H, J = 8.1 Hz); 7.32 (d, 2H, J = 7.5 Hz); 7.66-7.72 (m, 3H); 8.13 (d, 2H, J = 8.0 Hz). |
| | 2: Obtaining 3-(4-(((2-methoxy-6-(4-trifluoromethyl)phenyl)pyridin-3-yl)methyl)amino)-phenyl)-propanoic acid (Protocol SU and PA) | Yield: 58%. Appearance: white solid.<br>¹H NMR: 2.39 (t, 2H, J = 7.3 Hz); 2.63 (t, 2H, J = 7.3 Hz); 4.06 (s, 3H); 4.22 (d, 2H, J = 5.9 Hz); 6.05 (t, 1H, J = 5.9 Hz); 6.48 (d, 2H, J = 8.3 Hz); 6.91 (d, 2H, J = 8.3 Hz); 7.62-7.69 (m, 2H); 7.83 (d, 2H, J = 8.4 Hz); 8.29 (d, 2H, J = 8.4 Hz). |
| 38 | 1: Preparation of ethyl 3-(4-((2-(ethylthio)-6-phenylpyridin-3-yl)methylamino)-phenyl)propanoate (Ex. 5-9 and Ex. 6-15 with Protocol SX and PA) | Yield: 84%. Appearance: yellow solid.<br>¹H NMR: 1.24 (t, 3H, J = 7.3 Hz); 1.50 (t, 3H, J = 7.3 Hz); 2.56 (t, 2H, J = 7.6 Hz); 2.85 (t, 2H, J = 7.6 Hz); 3.41 (q, 2H, J = 7.3 Hz); 4.13 (q, 2H, J = 7.3 Hz); 4.32 (s, 2H); 6.57 (d, 2H, J = 8.5 Hz); 7.02 (d, 2H, J = 8.5 Hz); 7.40-7.50 (m, 4H); 7.60 (d, 1H, J = 7.9 Hz); 8.04-8.07 (m, 2H). |
| | 2: Obtaining 3-(4-(((2-(ethylthio)-6-phenylpyridin-3-yl)methyl)amino)phenyl)-propanoic acid (Protocol SU and PA) | Yield: 40%. Appearance: beige solid.<br>¹H NMR: 1.40 (t, 3H, J = 7.3 Hz); 2.41 (t, 2H, J = 7.3 Hz); 2.64 (t, 2H, J = 7.3 Hz); 3.30-3.38 (m, 2H); 4.16 (d, 2H, J = 5.9 Hz); 6.15 (t, 1H, J = 5.9 Hz); 6.44 (d, 2H, J = 8.5 Hz); 6.92 (d, 2H, J = 8.5 Hz); 7.39-7.51 (m, 3H); 7.59-7.68 (m, 2H); 8.09 (d, 2H, J = 7.0 Hz); 12.00 (s, 1H). |
| 39 | 1: Preparation of ethyl 3-(4-((2-methoxy-6-(parabiphenyl)pyridin-3-yl)methyl-amino)phenyl)-propanoate (Ex. 5-10 and Ex. 6-15 with Protocol SX and PA) | Yield: 84%. Appearance: yellow oil.<br>¹H NMR: 1.25 (t, 3H, J = 7.0 Hz); 2.57 (t, 2H, J = 7.3 Hz); 2.86 (t, 2H, J = 7.3 Hz); 4.10-4.17 (m, 5H); 4.34 (s, 2H); 6.61 (d, 2H, J = 8.5 Hz); 7.03 (d, 2H, J = 8.5 Hz); 7.34-7.41 (m, 2H); 7.48 (m, 2H); 7.62-7.72 (m, 5H); 8.13 (d, 2H, J = 8.5 Hz). |
| | 2: Obtaining 3-(4-(((2-methoxy-6-(parabiphenyl)pyridin-3-yl)methyl)amino)phenyl)-propanoic acid (Protocol SU and PA) | Yield: 60%. Appearance: beige solid.<br>¹H NMR: 2.41 (t, 2H, J = 7.3 Hz); 2.64 (t, 2H, J = 7.3 Hz); 4.06 (s, 3H); 4.21 (d, 2H, J = 5.6 Hz); 6.03 (t, 1H, J = 5.6 Hz); 6.49 (d, 2H, J = 8.5 Hz); 6.91 (d, 2H, J = 8.5 Hz); 7.36-7.41 (m, 1H); 7.49 (t, 2H, J = 7.0 Hz); 7.58 (d, 1H, J = 7.6 Hz); 7.64 (d, 1H, J = 7.6 Hz); 7.72-7.79 (m, 4H); 8.17 (d, 2H, J = 8.5 Hz). |
| 40 | 1: Preparation of ethyl 3-(4-((2-methoxy-6-(3-(trifluoromethyl)phenyl)pyridin-3-yl)methylamino)phenyl)propanoate (Ex. 5-11 and Ex. 6-15 with Protocol SX and PA) | Yield: 86%. Appearance: yellow oil.<br>¹H NMR: 1.24 (t, 3H, J = 7.3 Hz); 2.56 (t, 2H, J = 7.3 Hz); 2.85 (t, 2H, J = 7.3 Hz); 4.09-4.17 (m, 5H); 4.35 (s, 2H); 6.59 (d, 2H, J = 8.5 Hz); 7.02 (d, 2H, J = 8.5 Hz); 7.33 (d, 1H, J = 7.6 Hz); 7.54-7.66 (m, 3H); 8.20 (d, 1H, J = 7.6 Hz); 8.30 (s, 1H). |
| | 2: Obtaining 3-(4-(((2-methoxy-6-(3-(trifluoromethyl)phenyl)pyridin-3-yl)methyl)amino)-phenyl)propanoic acid (Protocol SU and PA) | Yield: 53%. Appearance: beige solid.<br>¹H NMR: 2.63 (t, 2H, J = 7.6 Hz); 2.86 (t, 2H, J = 7.6 Hz); 4.12 (s, 3H); 4.34 (s, 2H); 6.59 (d, 2H, J = 8.5 Hz); 7.03 (d, 2H, J = 8.5 Hz); 7.34 (d, 1H, J = 7.6 Hz); 7.54-7.66 (m, 3H); 8.20 (d, 1H, J = 7.6 Hz); 8.30 (s, 1H). |

TABLE 7-1-continued

| Cpd | No. and type of Stage (Ex.; Protocol) | Details |
|---|---|---|
| 41 | 1: Preparation of ethyl 3-(4-((2-methoxy-5-phenylpyridin-3-yl)methylamino)-phenyl)propanoate (Ex. 5-4 and Ex. 6-15 with Protocol SX and PA) | Yield: 72%. Appearance: colorless oil.<br>$^1$H NMR (300 MHz, CDCl$_3$, d in ppm): 1.22 (t, 3H, J = 7.3 Hz); 2.56 (t, 2H, J = 7.3 Hz); 2.84 (t, 2H, J = 7.3 Hz); 4.05 (s, 3H); 4.11 (q, 2H, J = 7.3 Hz); 4.34 (s, 2H); 6.60 (d, 2H, J = 8.5 Hz); 7.02 (d, 2H, J = 8.5 Hz); 7.31-7.36 (m, 1H); 7.39-7.50 (m, 4H); 7.80 (d, 1H, J = 2.4 Hz); 8.29 (d, 1H, J = 2.4 Hz). |
|  | 2: Obtaining 3-(4-(((2-methoxy-5-phenylpyridin-3-yl)methyl)amino)phenyl)-propanoic acid (Protocol SU and PA) | Yield: 57%. Appearance: white solid<br>$^1$H NMR: 2.39 (t, 2H, J = 7.9 Hz); 2.63 (t, 2H, J = 7.3 Hz); 3.97 (s, 3H); 4.22 (d, 2H, J = 5.0 Hz); 6.00 (m, 1H); 6.51 (d, 2H, J = 8.5 Hz); 6.91 (d, 2H, J = 8.5 Hz); 7.33 (m, 1H); 7.43 (m, 2H); 7.54 (d, 2H, J = 7.3 Hz); 7.86 (d, 1H, J = 2.3 Hz); 8.34 (d, 1H, J = 2.3 Hz). |
| 42 | 1: Preparation of ethyl 3-(4-((2-methoxy-6-phenylpyridin-3-yl)methylamino)phenyl)-3-phenylpropanoate (Ex. 5-1 and Ex. 6-14 with Protocol SX and PA) | Yield: 75%. Appearance: colorless oil.<br>$^1$H NMR: 1.11 (t, 3H, J = 7.0 Hz); 3.00 (d, 2H, J = 8.1 Hz); 4.03 (q, 2H, J = 7.0 Hz); 4.10 (s, 3H); 4.31 (s, 2H); 4.45 (t, 1H, J = 8.1 Hz); 6.57 (d, 2H, J = 8.6 Hz); 7.05 (d, 2H, J = 8.6 Hz); 7.15-7.32 (m, 6H); 7.36-7.49 (m, 4H); 7.60 (d, 1H, J = 7.6 Hz); 8.04 (d, 1H, J = 7.0 Hz). |
|  | 2: Obtaining 3-(4-((2(-methoxy-6-phenylpyridin-3-yl)methyl)amino)phenyl)-3-phenyl-propanoic acid (Protocol SU and PA)<br>3: Protocol PC | Yield: 36%. Appearance: white solid.<br>$^1$H NMR: 2.88 (dd, 2H, J = 7.9 Hz J = 9.4 Hz); 4.03 (s, 3H); 4.17-4.25 (m, 3H); 6.05 (m, 1H); 6.46 (d, 2H, J = 8.5 Hz); 6.98 (d, 2H, J = 8.5 Hz); 7.08-7.16 (m, 1H); 7.22-7.26 (m, 4H); 7.36-7.50 (m, 4H); 7.61 (d, 1H, J = 7.6 Hz); 8.05 (d, 2H, J = 7.0 Hz). |
| 43 | 1: Preparation of ethyl 3-(2-methoxy-4-((2-methoxy-6-phenylpyridin-3-yl)methyl-amino)phenyl)propanoate (Ex. 5-1 and Ex. 6-22 with Protocol SX and PA) | Yield: 57%. Appearance: yellow oil.<br>$^1$H NMR: 1.24 (t, 3H, J = 7.3 Hz); 2.55 (m, 2H); 2.83 (m, 2H); 3.76 (s, 3H); 4.08-4.15 (m, 5H); 4.33 (s, 2H); 6.17-6.20 (m, 2H); 6.94 (d, 1H, J = 7.6 Hz); 7.32 (d, 1H, J = 7.3 Hz); 7.36-7.49 (m, 3H); 7.63 (d, 1H, J = 7.6 Hz); 8.03-8.06 (m, 2H). |
|  | 2: Obtaining 3-(2-methoxy-4-(((2-methoxy-6-phenylpyridin-3-yl)methyl)amino)-phenyl)propanoic acid (Protocol SU and PA)<br>3: Protocol PC | Yield: 44%. Appearance: yellowish solid.<br>$^1$H NMR: 2.33 (m, 2H); 2.60 (m, 2H); 3.67 (s, 3H); 4.04 (s, 3H); 4.21 (d, 2H, J = 5.0 Hz); 6.00 (dd, 1H, J = 1.9 Hz J = 8.1 Hz); 6.05 (m, 1H); 6.26 (d, 1H, J = 1.9 Hz); 6.78 (d, 1H, J = 8.1 Hz); 7.37-7.54 (m, 4H); 7.66 (d, 1H, J = 7.6 Hz); 8.07 (d, 2H, J = 7.3 Hz); 11.97 (s(l), 1H). |
| 44 | 1: Preparation of ethyl 3-(3-methoxy-4-((2-methoxy-6-phenylpyridin-3-yl)methyl-amino)phenyl)propanoate (Ex. 5-1 and Ex. 6-23 with Protocol SX and PA) | Yield: 51%. Appearance: yellow oil.<br>$^1$H NMR: 1.25 (t, 3H, J = 7.1 Hz); 2.58 (m, 2H); 2.87 (m, 2H); 3.88 (s, 3H); 4.11 (s, 3H); 4.12 (q, 2H, J = 7.1 Hz); 4.35 (s, 2H); 6.48 (d, 1H, J = 8.2 Hz); 6.64-6.67 (m, 2H); 7.30 (d, 1H, J = 7.6 Hz); 7.35-7.48 (m, 3H); 7.60 (d, 1H, J = 7.3 Hz); 8.02-8.05 (m, 2H). |
|  | 2: Obtaining 3-(3-methoxy-4-(((2-methoxy-6-phenylpyridin-3-yl)methyl)amino)-phenyl)propanoic acid (Protocol SU and PA)<br>3: Protocol PC | Yield: 46%. Appearance: white solid.<br>$^1$H NMR: 2.44 (t, 2H, J = 7.9 Hz); 2.67 (t, 2H, J = 7.9 Hz); 3.80 (s, 3H); 4.04 (s, 3H); 4.26 (m, 2H); 5.36 (m, 1H); 6.26 (d, 1H, J = 8.1 Hz); 6.53 (dd, 1H, J = 1.4 Hz J = 8.1 Hz); 6.71 (d, 1H, J = 1.4 Hz); 7.36-7.50 (m, 4H); 7.56 (d, 1H, J = 7.6 Hz); 8.06 (d, 2H, J = 7.7 Hz); 12.01 (s, 1H). |
| 45 | 1: Preparation of ethyl 3-(4-((2-methoxy-6-phenylpyridin-3-yl)methylamino)-phenyl)butanoate (Ex. 5-1 and Ex. 6-24 with Protocol SX and PA) | Yield: 56%. Appearance: yellow oil;<br>$^1$H NMR: 1.19 (t, 3H, J = 7.2 Hz); 1.26 (d, 3H, J = 7.0 Hz); 2.43-2.60 (m, 2H); 3.14-3.22 (m, 1H); 4.08 (q, 2H, J = 7.2 Hz); 4.11 (s, 3H); 4.33 (s, 2H); 6.60 (d, 2H, J = 8.5 Hz); 7.03 (d, 2H, J = 8.5 Hz); 7.31 (d, 1H, J = 7.3 Hz); 7.36-7.49 (m, 3H); 7.62 (d, 1H, J = 7.6 Hz); 8.04 (d, 2H, J = 8.5 Hz). |
|  | 2: Obtaining 3-(4-(((2-methoxy-6-phenylpyridin-3-yl)methyl)amino)phenyl)butanoic acid (Protocol SU and PA)<br>3: Protocol PC | Yield: 52%; Appearance: white solid.<br>$^1$H NMR: 1.12 (d, 3H, J = 6.7 Hz); 2.37 (m, 2H); 2.93-3.00 (m, 1H); 4.04 (s, 3H); 4.20 (d, 2H, J = 4.4 Hz); 6.00 (m, 1H); 6.48 (d, 2H, J = 8.2 Hz); 6.93 (d, 2H, J = 8.2 Hz); 7.37-7.53 (m, 4H); 7.63 (d, 1H, J = 7.6 Hz); 8.06 (d, 2H, J = 7.3 Hz); 11.93 (s, 1H). |
| 46 | 1: Preparation of ethyl 3-(4-((2-methoxy-5-(4-(trifluoromethyl)phenyl)pyridin-3-yl)methylamino)phenyl)propanoate (Ex. 5-12 and Ex. 6-15 with Protocol SX and PA) | Yield: 74%. Appearance: yellow oil.<br>$^1$H NMR: 1.22 (t, 3H, J = 7.0 Hz); 2.55 (m, 2H); 2.84 (m, 2H); 4.06 (s, 3H); 4.11 (q, 2H, J = 7.0 Hz); 4.36 (s, 2H); 6.62 (d, 2H, J = 8.5 Hz); 7.02 (d, 2H, J = 8.5 Hz); 7.58 (d, 2H, J = 8.2 Hz); 7.67 (d, 2H, J = 8.2 Hz); 7.81 (d, 1H, J = 2.3 Hz); 8.30 (d, 1H, J = 2.3 Hz). |

TABLE 7-1-continued

| Cpd | No. and type of Stage (Ex.; Protocol) | Details |
|---|---|---|
|  | 2: Obtaining 3-(4-(((2-methoxy-5-(4-(trifluoromethyl) phenyl)pyridin-3-yl)methyl) amino) phenyl)propanoic acid (Protocol SU and PA)<br>3: Protocol PC | Yield: 44%. Appearance: white solid.<br>$^1$H NMR: 2.39 (t, 2H, J = 7.6 Hz); 2.63 (t, 2H, J = 7.6 Hz); 3.99 (s, 3H); 4.23 (d, 2H, J = 5.7 Hz); 5.99 (t, 1H, J = 5.7 Hz); 6.51 (d, 2H, J = 8.4 Hz); 6.91 (d, 2H, J = 8.4 Hz); 7.75-7.82 (m, 4H); 7.95 (d, 1H, J = 2.5 Hz); 8.44 (d, 1H, J = 2.5 Hz); 12.00 (s, 1H). |
| 47 | 1: Preparation of ethyl 3-(4-((2-methoxy-5-(3-(trifluoromethyl)phenyl)pyridin-3-yl)methylamino)-phenyl)propanoate (Ex. 5-13 and Ex. 6-15 with Protocol SX and PA)<br>2: Obtaining 3-(4-(((2-methoxy-5-(3-(trifluoromethyl) phenyl) pyridin-3-yl)methyl)amino)-phenyl) propanoic acid (Protocol SU and PA)<br>3: Protocol PC | Yield: 65%. Appearance: yellow oil.<br>$^1$H NMR: 1.22 (t, 3H, J = 7.0 Hz); 2.55 (m, 2H); 2.84 (m, 2H); 4.06 (s, 3H); 4.11 (q, 2H, J = 7.0 Hz); 4.36 (s, 2H); 6.60 (d, 2H, J = 8.5 Hz); 7.02 (d, 2H, J = 8.5 Hz); 7.51-7.66 (m, 3H); 7.70 (s, 1H); 7.79 (d, 1H, J = 2.5 Hz); 8.29 (d, 1H, J = 2.5 Hz).<br>Yield: 52%. Appearance: white solid.<br>$^1$H NMR: 2.39 (m, 2H); 2.63 (m, 2H); 3.98 (s, 3H); 4.23 (d, 2H, J = 5.7 Hz); 5.98 (t, 1H, J = 5.7 Hz); 6.52 (d, 2H, J = 8.3 Hz); 6.91 (d, 2H, J = 8.3 Hz); 7.67-7.69 (m, 2H); 7.85-7.89 (m, 2H); 7.96 (d, 1H, J = 2.3 Hz); 8.44 (d, 1H, J = 2.3 Hz); 11.98 (s, 1H). |
| 48 | 1: Preparation of ethyl 3-(4-((2,6-dimethoxy-5-phenylpyridin-3-yl)methylamino)-phenyl)propanoate (Ex. 5-14 and Ex. 6-15 with Protocol SX and PA)<br><br>2: Obtaining 3-(4-(((2,6-dimethoxy-5-phenylpyridin-3-yl)methyl)amino)phenyl)-propanoic acid (Protocol SU and PA)<br>3: Protocol PC | Yield: 48%. Appearance: colorless oil.<br>$^1$H NMR: 1.23 (t, 3H, J = 7.0 Hz); 2.56 (t, 2H, J = 7.3 Hz); 2.84 (t, 2H, J = 7.3 Hz); 3.97 (s, 3H); 4.00 (s, 3H); 4.12 (q, 2H, J = 7.0 Hz); 4.25 (s, 2H); 6.61 (d, 2H, J = 8.5 Hz); 7.01 (d, 2H, J = 8.5 Hz); 7.28-7.31 (m, 1H); 7.36-7.41 (m, 2H); 7.50 (m, 2H); 7.58 (s, 1H).<br>Yield: 46%. Appearance: beige solid.<br>$^1$H NMR: 2.39 (t, 2H, J = 7.6 Hz); 2.62 (t, 2H, J = 7.6 Hz); 3.90 (s, 3H); 3.99 (s, 3H); 4.13 (d, 2H, J = 5.7 Hz); 5.87 (t, 1H, J = 5.7 Hz); 6.49 (d, 2H, J = 8.2 Hz); 6.89 (d, 2H, J = 8.2 Hz); 7.24-7.29 (m, 1H); 7.34-7.44 (m, 4H); 7.62 (s, 1H); 12.05 (s, 1H). |
| 49 | 1: Preparation of ethyl 3-(4-((5-(4-chlorophenyl)-2-methoxypyridin-3-yl)methyl-amino)phenyl)propanoate (Ex. 5-15 and Ex. 6-15 with Protocol SX and PA)<br><br>2: Obtaining 3-(4-(((5-(4-chlorophenyl)-2-methoxypyridin-3-yl)methyl)amino)phenyl)-propanoic acid (Protocol SU and PC) | Yield: 68%. Appearance: colorless oil.<br>$^1$H NMR: 1.22 (t, 3H, J = 7.2 Hz); 2.55 (m, 2H); 2.84 (m, 2H); 4.05 (s, 3H); 4.11 (q, 2H, J = 7.2 Hz); 4.34 (s, 2H); 6.58 (d, 2H, J = 8.5 Hz); 7.01 (d, 2H, J = 8.5 Hz); 7.39 (m, 4H); 7.75 (d, 1H, J = 2.5 Hz); 8.25 (d, 1H, J = 2.5 Hz).<br>Yield: 32%. Appearance: white solid.<br>$^1$H NMR: 2.62 (m, 2H); 2.85 (m, 2H); 4.05 (s, 3H); 4.33 (s, 2H); 6.59 (d, 2H, J = 8.4 Hz); 7.02 (d, 2H, J = 8.4 Hz); 7.38 (m, 4H); 7.75 (d, 1H, J = 2.4 Hz); 8.25 (d, 1H, J = 2.4 Hz). |
| 50 | 1: Preparation of ethyl 3-(4-((2-methoxy-5-(naphthalen-2-yl)pyridin-3-yl)methyl-amino)phenyl)propanoate (Ex. 5-16 and Ex. 6-15 with Protocol SX and PA)<br>2: Obtaining 3-(4-(((2-methoxy-5-(naphthalen-2-yl)pyridin-3-yl)methyl) amino)phenyl)-propanoic acid (Protocol SU and PC) | Yield: 80%. Appearance: colorless oil.<br>$^1$H NMR: 1.20 (t, 3H, J = 7.2 Hz); 2.56 (m, 2H); 2.84 (m, 2H); 4.08 (s, 3H); 4.10 (q, 2H, J = 7.2 Hz); 4.38 (s, 2H); 6.64 (d, 2H, J = 8.4 Hz); 7.03 (d, 2H, J = 8.4 Hz); 7.45-7.54 (m, 2H); 7.62 (dd, 1H, J = 1.8 Hz J = 8.5 Hz); 7.84-7.93 (m, 5H); 8.41 (d, 1H, J = 2.4 Hz).<br>Yield: 53%. Appearance: white solid.<br>$^1$H NMR: 2.40 (m, 2H); 2.63 (m, 2H); 4.00 (s, 3H); 4.25 (m, 2H); 6.02 (m, 1H); 6.53 (d, 2H, J = 8.5 Hz); 6.92 (d, 2H, J = 8.5 Hz); 7.47-7.55 (m, 2H); 7.72 (dd, 1H, J = 1.5 Hz J = 8.5 Hz); 7.90-8.09 (m, 5H); 8.50 (d, 1H, J = 2.3 Hz); 11.99 (s, 1H). |
| 51 | 1: Preparation of ethyl 3-(4-((2-ethoxy-6-phenylpyridin-3-yl)methylamino)-phenyl)propanoate (Ex. 5-17 and Ex. 6-15 with Protocol SX and PA)<br><br>2: Obtaining 3-(4-(((2-ethoxy-6-phenylpyridin-3-yl)methyl)amino)phenyl)propanoic acid (Protocol SU and PA)<br>3: Protocol PC | Yield: 49%. Appearance: colorless oil.<br>$^1$H NMR: 1.24 (t, 3H, J = 7.1 Hz); 1.47 (t, 3H, J = 7.0 Hz); 2.56 (m, 2H); 2.84 (m, 2H); 4.12 (q, 2H, J = 7.1 Hz); 4.33 (s, 2H); 4.58 (q, 2H, J = 7.0 Hz); 6.60 (d, 2H, J = 8.5 Hz); 7.02 (d, 2H, J = 8.5 Hz); 7.27-7.30 (m, 1H); 7.35-7.48 (m, 3H); 7.60 (d, 1H, J = 7.6 Hz); 8.00-8.03 (m, 2H).<br>Yield: 77%. Appearance: white solid.<br>$^1$H NMR: 1.41 (t, 3H, J = 7.0 Hz); 2.41 (m, 2H); 2.64 (m, 2H); 4.20 (s, 2H); 4.52 (q, 2H, J = 7.0 Hz); 5.99 (s, 1H); 6.48 (d, 2H, J = 8.2 Hz); 6.91 (d, 2H, J = 8.2 Hz); 7.36-7.50 (m, 4H); 7.62 (d, 1H, J = 7.6 Hz); 8.04 (d, 2H, J = 7.3 Hz); 12.01 (s, 1H). |
| 54 | 1: Preparation of ethyl 3-(4-((2-isopropoxy-6-phenylpyridin-3-yl)methylamino)-phenyl)propanoate (Ex. 5-18 and Ex. 6-15 with Protocol SX and PA)<br><br>2: Obtaining 3-(4-(((2-isopropyloxy-6-phenylpyridin-3-yl)methyl)amino)phenyl)-propanoic acid (Protocol SU and PA)<br>3: Protocol PC | Yield: 65%. Appearance: colorless oil.<br>$^1$H NMR: 1.24 (t, 3H, J = 7.1 Hz); 1.44 (s, 3H); 1.46 (s, 3H); 2.57 (m, 2H); 2.84 (m, 2H); 4.13 (q, 2H, J = 7.1 Hz); 4.31 (s, 2H); 5.55-5.63 (m, 1H); 6.59 (d, 2H, J = 8.5 Hz); 7.02 (d, 2H, J = 8.5 Hz); 7.27 (d, 1H, J = 7.6 Hz); 7.35-7.47 (m, 3H); 7.59 (d, 1H, J = 7.6 Hz); 8.01 (m, 2H).<br>Yield: 75%. Appearance: white solid.<br>$^1$H NMR: 1.39 (s, 3H); 1.41 (s, 3H); 2.41 (m, 2H); 2.64 (m, 2H); 4.17 (s, 2H); 5.44-5.52 (m, 1H); 5.97 (m, 1H); 6.48 (d, 2H, J = 8.4 Hz); 6.92 (d, 2H, J = 8.4 Hz); 7.35-7.47 (m, 4H); 7.62 (d, 1H, J = 7.6 Hz); 8.02 (d, 2H, J = 7.0 Hz); 12.01 (s, 1H). |

Synthesis of the compounds according to the invention in FIGS. 7b and 7c requires 2 stages and is summarized in Table 7-2.

TABLE 7-2

| Cpd | No. and type of Stage (Ex.; Protocol) | Details |
| --- | --- | --- |
| 13 | 1: Preparation of tert-butyl 2-(3-((2-methoxy-6-phenylpyridin-3-yl)methylamino)phenoxy)-2-methyl-propanoate (Ex. 5-1 and Ex. 6-12 with Protocol SX and PA) | Yield: 49%. Appearance: yellow oil.<br>$^1$H NMR: 1.45 (s, 9H); 1.55 (s, 6H); 4.11 (s, 3H); 4.18 (s, 1H); 4.31 (s, 2H); 6.20-6.31 (m, 3H); 7.01 (m, 1H); 7.31 (d, 1H, J = 7.6 Hz); 7.37-7.49 (m, 3H); 7.61 (d, 1H, J = 7.6 Hz); 8.05 (d, 2H, J = 8.8 Hz). |
| | 2: Obtaining 2-(3-(((2-methoxy-6-phenylpyridin-3-yl)methyl)amino)phenoxy)-2-methyl-propanoic acid (Protocol SU and PB) | Yield: 33%. Appearance: white solid.<br>$^1$H NMR: 1.42 (s, 6H); 4.17 (d, 2H, J = 5.5 Hz); 5.98-6.02 (m, 2H); 6.16-6.20 (m, 2H); 6.90 (t, 1H, J = 7.9 Hz); 7.37-7.53 (m, 4H); 7.62 (d, 1H, J = 7.6 Hz); 8.07 (d, 2H, J = 7.3 Hz). |
| 14 | 1: Preparation of tert-butyl 2-(3-((2-methoxy-6-phenylpyridin-3-yl)methylamino)-phenoxy)ethanoate (Ex. 5-1 and Ex. 6-13 with Protocol SX and PA) | Yield: 80%. Appearance: yellow oil.<br>$^1$H NMR: 1.49 (s, 9H); 4.12 (s, 3H); 4.33 (s, 2H); 4.47 (s, 2H); 6.22-6.33 (m, 3H); 7.08 (t, 1H, J = 7.6 Hz); 7.31 (d, 1H, J = 7.6 Hz); 7.37-7.49 (m, 3H); 7.61 (d, 1H, J = 7.6 Hz); 8.05 (d, 2H, J = 7.0 Hz). |
| | 2: Obtaining 2-(3-(((2-methoxy-6-phenylpyridin-3-yl)methyl)amino)phenoxy) ethanoic acid (Protocol SU and PB) | Yield: 60%. Appearance: white solid.<br>$^1$H NMR: 4.12 (s, 3H); 4.34 (s, 2H); 4.61 (s, 2H); 6.24-6.37 (m, 3H); 7.09 (m, 1H); 7.31 (d, 1H, J = 7.6 Hz); 7.36-7.48 (m, 3H); 7.60 (d, 1H, J = 7.6 Hz); 8.04 (d, 2H, J = 6.7 Hz). |
| 34 | 1: Preparation of ethyl 3-(4-(1-(2-methoxy-6-phenylpyridin-3-yl)propylamino)-phenyl)propanoate (Ex. 5-8 and Ex. 6-15 with Protocol SY and PA) | Yield: 14%. Appearance: yellow oil |
| | 2: Obtaining 3-(4-(1-((2-methoxy-6-phenylpyridin-3-yl)propyl)amino)phenyl)-propanoic acid (Protocol SU and PB) | Yield: 58%. Appearance: white solid.<br>$^1$H NMR: 0.94 (t, 3H, J = 7.3 Hz); 1.65-1.78 (m, 2H); 2.35 (t, 2H, J = 7.3 Hz); 2.58 (t, 2H, J = 7.3 Hz); 4.06 (s, 3H); 4.46 (m, 1H); 5.96 (d, 1H, J = 7.9 Hz); 6.39 (d, 2H, J = 8.5 Hz); 6.83 (d, 2H, J = 8.5 Hz); 7.36-7.51 (m, 4H); 7.66 (d, 1H, J = 7.9 Hz); 8.06 (d, 2H; J = 7.0 Hz). |

Synthesis of the compounds according to the invention in FIG. 7d requires 2 or 3 stages and is summarized in Table 7-3.

TABLE 7-3

| Cpd | No. and type of Stage (Ex.; Protocol) | Details |
| --- | --- | --- |
| 2 | 1: Preparation of tert-butyl 2-(4-((2-methoxy-6-phenylpyridin-3-yl)methoxy)phenoxy)-ethanoate (Ex. 4-1 and Ex. 6-2 with Protocol SV and PA) | Yield: 54%. Appearance: white solid.<br>$^1$H NMR: 1.47 (s, 9H); 4.11 (s, 3H); 4.59 (s, 2H); 5.02 (s, 2H); 6.88 (d, 2H, J = 9.1 Hz); 6.95 (d, 2H, J = 9.1 Hz); 7.34-7.49 (m, 4H); 7.76 (d, 1H, J = 7.6 Hz); 8.02 (m, 2H). |
| | 2: Obtaining 2-(4-((2-methoxy-6-phenylpyridin-3-yl)methoxy)phenoxy)ethanoic acid (Protocol SW and PE) | Yield: 83%. Appearance: white solid.<br>$^1$H NMR: 4.03 (s, 3H); 4.60 (s, 2H); 5.03 (s, 2H); 6.84 (d, 2H, J = 9.1 Hz); 6.96 (d, 2H, J = 9.1 Hz); 7.40-7.55 (m, 3H); 7.58 (d, 1H, J = 7.6 Hz); 7.84 (d, 1H, J = 7.6 Hz); 8.10 (d, 2H, J = 7.0 Hz); 12.83 (s (broad), 1H). |
| 6 | 1: Preparation of ethyl 2-(4-((2-tert-butoxy-6-phenylpyridin-3-yl)methoxy)phenoxy)-2-methyl-propanoate (Ex. 4-2 and Ex. 6-1 with Protocol SV and PA) | Yield: 33%. Appearance: yellow oil.<br>$^1$H NMR: 1.29 (t, 3H, J = 7.2 Hz); 1.57 (s, 6H); 1.71 (s, 9H); 4.26 (q, 2H, J = 7.2 Hz); 5.02 (s, 2H); 6.85-6.92 (m, 4H); 7.34-7.50 (m, 4H); 7.76 (d, 1H, J = 7.6 Hz); 8.03 (d, 2H, J = 7.3 Hz). |
| | 2: Obtaining 2-(4-((2-tert-butyloxy-6-phenylpyridin-3-yl)methoxy)phenoxy)-2-methyl-propanoic acid (Protocol SU and PD) | Yield: 67%. Appearance: white solid.<br>$^1$H NMR: 1.44 (s, 6H); 1.63 (s, 9H); 4.97 (s, 2H); 6.83 (d, 2H, J = 9.1 Hz); 6.93 (d, 2H, J = 9.1 Hz); 7.42-7.57 (m, 4H); 7.80 (d, 1H, J = 7.6 Hz); 8.03 (d, 2H, J = 7.3 Hz); 12.94 (s, 1H). |
| 7 | 1: Preparation of ethyl 2-(4-((2-tert-butoxy-6-phenylpyridin-3-yl)methoxy)phenoxy)ethanoate (Ex. 4-2 and Ex. 6-4 with Protocol SV and PA) | Yield: 80%. Appearance: white solid.<br>$^1$H NMR: 1.32 (t, 3H, J = 7.2 Hz); 1.71 (s, 9H); 4.29 (q, 2H, J = 7.2 Hz); 4.59 (s, 2H); 5.02 (s, 2H); 6.88 (d, 2H, J = 9.2 Hz); 6.95 (d, 2H, J = 9.2 Hz); 7.34-7.49 (m, 4H); 7.76 (d, 1H, J = 7.6 Hz); 8.02 (d, 2H, J = 7.3 Hz). |

TABLE 7-3-continued

| Cpd | No. and type of Stage (Ex.; Protocol) | Details |
|---|---|---|
| | 2: Obtaining 2-(4-(((2-tert-butyloxy-6-phenylpyridin-3-yl)methoxy)phenoxy)ethanoic acid (Protocol SU and PD) | Yield: 33%. Appearance: white solid.<br>$^1$H NMR: 1.64 (s, 9H); 4.59 (s, 2H); 4.97 (s, 2H); 6.85 (d, 2H, J = 9.1 Hz); 6.94 (d, 2H, J = 9.1 Hz); 7.39-7.56 (m, 4H); 7.79 (d, 1H, J = 7.6 Hz); 8.03 (d, 2H, J = 7.3 Hz); 12.94 (s, 1H). |
| 15 | 1: Preparation of tert-butyl 2-(4-((2-hexyloxy-6-phenylpyridin-3-yl)methoxy)-phenyl)-phenoxy)ethanoate (Ex. 4-3 and Ex. 6-2 with Protocol SV and PA) | Yield: 39%. Appearance: yellow oil.<br>$^1$H NMR: 0.91 (t, 3H, J = 7.0 Hz); 1.26-1.55 (m, 6H); 1.49 (s, 9H); 1.84 (m, 2H); 4.47 (s, 2H); 4.51 (t, 2H, J = 6.5 Hz); 5.06 (s, 2H); 6.85 (d, 2H, J = 9.4 Hz); 6.94 (d, 2H, J = 9.4 Hz); 7.34-7.48 (m, 4H); 7.77 (d, 1H, J = 7.6 Hz); 8.03 (d, 2H, J = 7.0 Hz). |
| | 2: Obtaining 2-(4-((2-hexyloxy-6-phenylpyridin-3-yl)methoxy)phenoxy)ethanoic acid (Protocol SW and PA)<br>3: Protocol PC | Yield: 31%. Appearance: white solid.<br>$^1$H NMR: 0.91 (t, 3H, J = 6.7 Hz); 1.34-1.49 (m, 6H); 1.79-1.88 (m, 2H); 4.51 (t, 2H, J = 6.7 Hz); 4.63 (s, 2H); 5.07 (s, 2H); 6.89 (d, 2H, J = 9.2 Hz); 6.95 (d, 2H, J = 9.2 Hz); 7.34-7.48 (m, 4H); 7.76 (d, 1H, J = 7.6 Hz); 8.03 (d, 2H, J = 7.2 Hz). |
| 17 | 1: Preparation of tert-butyl 2-(4-((2-hexyloxy-6-phenylpyridin-3-yl)methoxy)-phenoxy)-2-methyl-propanoate (Ex. 4-3 and Ex. 6-5 with Protocol SV and PA) | Yield: 37%; Appearance: yellow oil.<br>$^1$H NMR: 0.91 (t, 3H, J = 7.0 Hz); 1.30-1.46 (m, 6H); 1.46 (s, 9H); 1.52 (s, 6H); 1.83 (m, 2H); 4.51 (t, 2H, J = 6.4 Hz); 5.06 (s, 2H); 6.87 (m, 4H); 7.35-7.49 (m, 4H); 7.78 (d, 1H, J = 7.6 Hz); 8.03 (d, 2H, J = 7.9 Hz). |
| | 2: Obtaining 2-(4-((2-hexyloxy-6-phenylpyridin-3-yl)methoxy)phenoxy)-2-methyl-propanoic acid (Protocol SW and PB) | Yield: 26%; Appearance: white solid.<br>$^1$H NMR: 0.91 (t, 3H, J = 7.0 Hz); 1.26-1.56 (m, 12H); 1.79-1.89 (m, 2H); 4.52 (t, 2H, J = 6.7 Hz); 5.08 (s, 2H); 6.94 (m, 4H); 7.35-7.48 (m, 4H); 7.78 (d, 1H, J = 7.6 Hz); 8.04 (d, 2H, J = 8.5 Hz). |
| 18 | 1: Preparation of tert-butyl 2-(4-((2-cyclohexyloxy-6-phenylpyridin-3-yl)methoxy)-phenoxy)ethanoate (Ex. 4-4 and Ex. 6-2 with Protocol SV and PA) | Yield: 39%. Appearance: yellow oil.<br>$^1$H NMR: 1.50 (s, 9H); 1.50-1.72 (m, 6H); 1.80-1.83 (m, 2H); 2.03-2.04 (m, 2H); 4.48 (s, 2H); 5.07 (s, 2H); 5.33 (m, 1H); 6.88 (d, 2H, J = 9.2 Hz); 6.95 (d, 2H, J = 9.2 Hz); 7.34 (d, 1H, J = 7.6 Hz); 7.36-7.49 (d, 3H); 7.78 (d, 1H, J = 7.6 Hz); 8.02 (d, 2H, J = 8.5 Hz). |
| | 2: Obtaining 2-(4-((2-cyclohexyloxy-6-phenylpyridin-3-yl)methoxy)phenoxy)ethanoic acid (Protocol SW and PB) | Yield: 16%. Appearance: white solid.<br>$^1$H NMR: 1.26-2.03 (m, 10H); 4.64 (s, 2H); 5.07 (s, 2H); 5.32-5.36 (m, 1H); 6.88-6.99 (m, 4H); 7.32-7.48 (m, 4H); 7.76 (d, 1H, J = 7.6 Hz); 8.01 (d, 2H, J = 7.0 Hz). |
| 20 | 1: Preparation of ethyl 2-(4-((6-phenyl-2-(piperidin-1-yl)pyridin-3-yl)methoxy)-phenoxy)ethanoate (Ex. 4-5 and Ex. 6-4 with Protocol SV and PA) | Yield: 60%. Appearance: white solid.<br>$^1$H NMR: 0.84 (m, 3H); 1.34-1.76 (m, 6H); 3.27 (m, 4H); 4.27 (q, 2H, J = 7.0 Hz); 4.57 (s, 2H); 5.07 (s, 2H); 6.85-6.94 (m, 4H); 7.39-7.48 (m, 4H); 7.82-7.86 (m, 1H); 8.05 (d, 2H, J = 6.7 Hz). |
| | 2: Obtaining 2-(4-((6-phenyl-2-(piperidin-1-yl)pyridin-3-yl)methoxy)phenoxy)-ethanoic acid (Protocol SU and PB) | Yield: 21%. Appearance: white solid.<br>$^1$H NMR: 1.59-1.67 (m, 6H); 3.17 (m, 4H); 4.49 (s, 2H); 5.00 (s, 2H); 6.82 (d, 2H, J = 9.2 Hz); 6.92 (d, 2H, J = 9.2 Hz); 7.37-7.49 (m, 3H); 7.57 (d, 1H, J = 7.7 Hz); 7.82 (d, 1H, J = 7.7 Hz); 8.07 (d, 2H, J = 7.0 Hz). |
| 21 | 1: Preparation of tert-butyl 2-(4-((2-methoxy-6-(4-(trifluoromethyl)phenyl)pyridin-3-yl)methoxy)-phenoxy)-2-methyl propanoate (Ex. 4-6 and Ex. 6-5 with Protocol SV and PA) | Yield: 47%; Appearance: white solid.<br>$^1$H NMR: 1.47 (s, 9H); 1.53 (s, 6H); 4.09 (s, 3H); 5.07 (s, 2H); 6.85-6.92 (m, 4H); 7.43 (d, 1H, J = 7.6 Hz); 7.72 (d, 2H, J = 8.2 Hz); 7.84 (d, 1H, J = 7.6 Hz); 8.17 (d, 2H, J = 8.2 Hz). |
| | 2: Obtaining 2-(4-((2-methoxy-6-(4-(trifluoromethyl) phenyl) pyridin-3-yl)methoxy)-phenoxy)-2-methylpropanoic acid (Protocol SW and PA)<br>3: Protocol PC | Yield: 34%. Appearance: white solid.<br>$^1$H NMR: 1.56 (s, 6H); 4.12 (s, 3H); 5.19 (s, 2H); 6.95 (s, 4H); 7.43 (d, 1H, J = 7.6 Hz); 7.72 (d, 2H, J = 8.2 Hz); 7.84 (d, 1H, J = 7.6 Hz); 8.17 (d, 2H, J = 8.2 Hz). |
| 24 | 1: Preparation of tert-butyl 2-(4-((2-methoxy-6-(4-(trifluoromethyl)phenyl)pyridin-3-yl)methoxy)phenoxy)ethanoate (Ex. 4-6 and Ex. 6-2 with Protocol SV and PA) | Yield: 53%. Appearance: white solid.<br>$^1$H NMR: 1.50 (s, 9H); 4.11 (s, 3H); 4.48 (s, 2H); 5.07 (s, 2H); 6.58-6.96 (m, 4H); 7.42 (d, 1H, J = 7.6 Hz); 7.71 (d, 2H, J = 8.2 Hz); 7.83 (d, 1H, J = 7.6 Hz); 8.16 (d, 2H, J = 8.2 Hz). |
| | 2: Obtaining 2-(4-((2-methoxy-6-(4-(trifluoromethyl)phenyl)pyridin-3-yl)methoxy)-phenoxy)ethanoic acid (Protocol SW and PA)<br>3: Protocol PC | Yield: 12%. Appearance: white solid.<br>$^1$H NMR: 4.12 (s, 3H); 4.64 (s, 2H); 5.09 (s, 2H); 6.92-6.96 (m, 4H); 7.42 (d, 1H, J = 7.6 Hz); 7.71 (d, 2H, J = 8.2 Hz); 7.82 (d, 1H, J = 7.6 Hz); 8.17 (d, 2H, J = 8.2 Hz). |

TABLE 7-3-continued

| Cpd | No. and type of Stage (Ex.; Protocol) | Details |
|---|---|---|
| 25 | 1: Preparation of ethyl 2-(4-((2-phenylthio-6-(phenyl)pyridin-3-yl)methoxy)-phenoxy)ethanoate (Ex. 4-7 and Ex. 6-4 with Protocol SV and PA) | Yield: 27%. Appearance: white solid. $^1$H NMR: 1.31 (t, 3H, J = 7.2 Hz); 4.28 (q, 2H, J = 7.2 Hz); 4.59 (s, 2H); 5.14 (s, 2H); 6.89 (d, 2H, J = 9.4 Hz); 6.96 (d, 2H, J = 9.4 Hz); 7.32-7.35 (m, 3H); 7.40-7.45 (m, 3H); 7.56 (d, 1H, J = 7.9 Hz); 7.60-7.63 (m, 2H); 7.75-7.81 (m, 3H). |
|  | 2: Obtaining 2-(4-((2-phenylthio-6-(phenyl)pyridin-3-yl)methoxy)phenoxy)ethanoic acid (Protocol SU and PD) | Yield: 71%; Appearance: white solid $^1$H NMR: 4.65 (s, 2H); 5.15 (s, 2H); 6.91 (d, 2H, J = 9.2 Hz); 6.98 (d, 2H, J = 9.2 Hz); 7.33-7.35 (m, 3H); 7.40-7.45 (m, 3H); 7.56 (d, 1H, J = 8.2 Hz); 7.59-7.63 (m, 2H); 7.74-7.81 (m, 3H). |
| 52 | 1: Preparation of ethyl 3-(4-((2-methoxy-5-phenylpyridin-3-yl)methoxy)phenyl)-hex-4-ynoate (Ex. 4-8 and Ex. 6-25 with Protocol SV and PA) | Yield: 18%; Appearance: yellow oil. $^1$H NMR: 1.22 (t, 3H, J = 7.3 Hz); 1.84 (d, 3H, J = 2.3 Hz); 2.66 (dd, 1H, J = 7.0 Hz, J = 14.9 Hz); 2.76 (dd, 1H, J = 8.2 Hz, J = 14.9 Hz); 4.05-4.18 (m, 6H); 5.10 (s, 2H); 6.96 (d, 2H, J = 8.8 Hz); 7.30-7.39 (m, 3H); 7.42-7.47 (m, 2H); 7.53-7.56 (m, 2H); 7.98 (d, 1H, J = 2.3 Hz); 7.34 (d, 1H, J = 2.3 Hz). |
|  | 2: Obtaining 3-(4-((2-methoxy-5-phenylpyridin-3-yl)methoxy)phenyl)hex-4-ynoic acid (Protocol SU and PB) | Yield: 26%. Appearance: white solid. $^1$H NMR (300 MHz, DMSO d$_6$, □ in ppm): 1.77 (s, 3H); 2.59 (d, 2H, J = 7.6 Hz); 3.96 (m, 4H); 5.07 (s, 2H); 6.99 (d, 2H, J = 8.5 Hz); 7.29 (d, 2H, J = 8.5 Hz); 7.34-7.39 (m, 1H); 7.47 (m, 2H); 7.65 (d, 2H, J = 7.6 Hz); 8.08 (d, 1H, J = 1.8 Hz); 8.47 (d, 1H, J = 1.8 Hz); 12.24 (s, 1H). |
| 53 | 1: Preparation of ethyl 3-(4-((2-methoxy-6-phenylpyridin-3-yl)methoxy)phenyl)-hex-4-ynoate (Ex. 4-1 and Ex. 6-25 with Protocol SV and PA) | Yield: 36%. Appearance: colorless oil. $^1$H NMR: 1.23 (t, 3H, J = 7.0 Hz); 1.84 (d, 3H, J = 2.3 Hz); 2.66 (dd, 1H, J = 7.0 Hz, J = 14.9 Hz); 2.76 (dd, 1H, J = 8.2 Hz, J = 14.9 Hz); 4.07-4.18 (m, 6H); 5.10 (s, 2H); 6.95 (d, 2H, J = 8.5 Hz); 7.31 (d, 2H, J = 8.5 Hz); 7.37-7.50 (m, 4H); 7.78 (d, 1H, J = 7.6 Hz); 8.04-8.08 (m, 2H). |
|  | 2: Obtaining 3-(4-((2-methoxy-6-phenylpyridin-3-yl)methoxy)phenyl)hex-4-ynoic acid (Protocol SU and PA) 3: Protocol PC | Yield: 42%. Appearance: white solid. $^1$H NMR: 2.39 (d, 3H, J = 2.3 Hz); 3.21 (d, 2H, J = 7.6 Hz); 4.54-4.59 (m, 1H); 4.65 (s, 3H); 5.68 (s, 2H); 7.58 (d, 2H, J = 8.8 Hz); 7.90 (d, 2H, J = 8.8 Hz); 8.01-8.13 (m, 3H); 8.21 (d, 1H, J = 7.6 Hz); 8.46 (d, 1H, J = 7.6 Hz); 8.71-8.74 (m, 2H); 12.88 (s, 1H). |

Synthesis of the compounds according to the invention in FIGS. 7e and 7f requires 1 or 2 stages and is summarized in Table 7-4.

TABLE 7-4

| Cpd | No. and type of Stage (Ex.; Protocol) | Details |
|---|---|---|
| 1 | 1: Preparation of ethyl 2-(4-((2-methoxy-6-phenylpyridin-3-yl)methoxy)phenoxy)-2-methyl-propanoate (Ex. 4-15 and Ex. 6-1 with Protocol SQ and PA) | Yield: 47%. Appearance: colorless oil. $^1$H NMR: 1.30 (t, 3H, J = 7.0 Hz); 1.57 (s, 6H); 4.12 (s, 3H); 4.26 (q, 2H, J = 7.0 Hz); 5.07 (s, 2H); 6.85-6.92 (m, 4H); 7.38-7.50 (m, 4H); 7.80 (d, 1H, J = 7.6 Hz); 8.07 (d, 2H, J = 7.3 Hz). |
|  | 2: Obtaining 2-(4-((2-methoxy-6-phenylpyridin-3-yl)methoxy)phenoxy)-2-methyl-propanoic acid (Protocol SU and PA) | Yield: 20%. Appearance: white solid. $^1$H NMR: 1.57 (s, 6H); 4.12 (s, 3H); 5.09 (s, 2H); 6.94 (s, 4H); 7.38-7.50 (m, 4H); 7.79 (d, 1H, J = 7.6 Hz); 8.06 (d, 2H, J = 7.3 Hz). |
| 3 | 1: Preparation of ethyl 2-(4-((2-methoxy-6-phenylpyridin-3-yl)methoxy)phenoxy)-propanoate (Ex. 4-15 and Ex. 6-3 with Protocol SQ and PA) | Yield: quantitative. Appearance: white solid. $^1$H NMR: 1.27 (t, 3H, J = 7.0 Hz); 1.62 (m, 3H); 4.11 (s, 3H); 4.23 (q, 2H, J = 7.0 Hz); 4.64-4.71 (m, 1H); 5.06 (s, 2H); 6.85 (d, 2H, J = 9.3 Hz); 6.93 (d, 2H, J = 9.3 Hz); 7.38-7.50 (m, 4H); 7.79 (d, 1H, J = 7.6 Hz); 8.06 (d, 2H, J = 7.3 Hz). |
|  | 2: Obtaining 2-(4-((2-methoxy-6-phenylpyridin-3-yl)methoxy)phenoxy)propanoic acid (Protocol SU and PD) | Yield: 29%. Appearance: white solid. $^1$H NMR: 1.35 (d, 3H, J = 6.4 Hz); 4.02 (s, 3H); 4.24 (m, 1H); 4.99 (s, 2H); 6.73 (d, 2H, J = 8.8 Hz); 6.87 (d, 2H, J = 8.8 Hz); 7.40-7.51 (m, 3H); 7.59 (d, 1H, J = 7.6 Hz); 7.82 (d, 1H, J = 7.6 Hz); 8.10 (d, 2H, J = 7.6 Hz). |

TABLE 7-4-continued

| Cpd No. | and type of Stage (Ex.; Protocol) | Details |
|---|---|---|
| 5 | 1: Preparation of ethyl 2-(4-((2-methoxy-6-phenylpyridin-3-yl)methylamino)phenoxy)propanoate (Ex. 4-16 and Ex. 6-7 with Protocol SQ and PA) | Yield: 20%. Appearance: yellow oil. $^1$H NMR: 1.27 (t, 3H, J = 7.1 Hz); 1.59 (d, 3H, J = 6.8 Hz); 4.11 (s, 3H); 4.22 (q, 2H, J = 7.1 Hz); 4.30 (s, 2H); 4.62 (q, 1H, J = 6.8 Hz); 6.61 (d, 2H, J = 9.0 Hz); 6.79 (d, 2H, J = 9.0 Hz); 7.31 (d, 1H, J = 7.6 Hz); 7.37-7.49 (m, 3H); 7.61 (d, 1H, J = 7.6 Hz); 8.05 (d, 2H, J = 7.3 Hz). |
| | 2: Obtaining 2-(4-(((2-methoxy-6-phenylpyridin-3yl)methyl)amino)phenoxy)propanoic acid (Protocol SU and PB) | Yield: 52%. Appearance: yellow solid. $^1$H NMR: 1.40 (d, 3H, J = 6.7 Hz); 3.36 (m, 1H); 4.03 (s, 3H); 4.17 (s, 2H); 4.53 (q, 1H, J = 6.7 Hz); 6.48 (d, 2H, J = 8.9 Hz); 6.65 (d, 2H, J = 8.9 Hz); 7.37-7.53 (m, 4H); 7.63 (d, 1H, J = 7.6 Hz); 8.07 (d, 2H, J = 7.3 Hz). |
| 33 | 1: Preparation of ethyl 3-(4-(((2-methoxy-6-phenylpyridin-3-yl)methyl)(methyl)-amino)phenyl)propanoate) (Cpd 19 with Protocol SQ and PA) | Yield: 39%. Appearance: yellow oil. $^1$H NMR: 1.24 (t, 3H, J = 7.3 Hz); 2.58 (t, 2H, J = 7.3 Hz); 2.87 (t, 2H, J = 7.3 Hz); 3.08 (s, 3H); 4.09-4.18 (m, 5H); 4.49 (s, 2H); 6.71 (m, 1H); 7.08 (d, 2H, J = 8.5 Hz); 7.29-7.53 (m, 6H); 8.03 (d, 2H, J = 7.0 Hz). |
| | 2: Obtaining 3-(4-(((2-methoxy-6-phenylpyridin-3-yl)methyl)(methyl)amino)phenyl)-propanoic acid (Protocol SU and PA) | Yield: 37%. Appearance: white solid. $^1$H NMR: 2.43 (t, 2H, J = 7.3 Hz); 2.67 (t, 2H, J = 7.3 Hz); 3.02 (s, 3H); 4.04 (s, 3H); 4.46 (s, 2H); 6.59 (d, 2H, J = 8.6 Hz); 8.05 (d, 2H, J = 8.6 Hz); 7.32-7.49 (m, 5H); 8.06 (d, 2H, J = 7.0 Hz). |
| 37 | Obtaining 3-(4-((2-methoxy-6-phenylpyridin-3-yl)methylthio)phenyl)propanoic acid (Ex. 4-16 and 3-(4-mercaptophenyl)propanoic acid with Protocol SQ and PB) | Yield: 9%. Appearance: white solid. $^1$H NMR: 2.41 (t, 2H, J = 7.6 Hz); 2.64 (t, 2H, J = 7.6 Hz); 4.03 (s, 3H); 4.21 (s, 2H); 6.50 (d, 2H, J = 8.3 Hz); 6.92 (d, 2H, J = 8.3 Hz); 7.36-7.53 (m, 4H); 7.63 (d, 1H, J = 7.6 Hz); 8.07 (d, 2H, J = 7.0 Hz). |

Example 8

PPAR Activating Properties of the Compounds According to the Invention

Principle

Activation of PPARs is evaluated in vitro on a line of monkey kidney fibroblasts (COS-7) by measuring the transcriptional activity of chimeras consisting of the DNA binding domain of Gal4 transcription factor of yeast and of the ligand binding domain of the various PPARs of human origin (hPPAR). The compounds are tested at doses between 0.01 and 100 µM on chimeras Gal4-PPARα, γ, δ and $EC_{50}$ is determined.

Protocol a) Cell Culture

The COS-7 cells are from ATCC and are cultivated in DMEM medium supplemented with 10% (vol/vol) of fetal calf serum, 1% of penicillin/streptomycin (Biochrom, AG), 1% of amino acids (Gibco) and 1% of sodium pyruvate (Gibco). The cells are incubated at 37° C. in a humid atmosphere containing 5% $CO_2$.

b) Description of the Plasmids Used in Transfection

The plasmids Gal4(RE)_TkpGL3, pGal4-hPPARα, pGal4-hPPARγ, pGal4-hPPARδ and pGal4-φ are described in the literature (Raspe E et al., 1999). The constructs pGal4-hPPARα, pGal4-hPPARγ and pGal4-hPPARδ were obtained by cloning, into the pGal4-φ vector, DNA fragments amplified by PCR corresponding to the DEF domains (structural elements of the promoter of the PPARs: D=hinge, EF=ligand fixation domain and AF2 fixation site) of the human nuclear receptors PPAα, PPARγ and PPARδ.

c) Transfection

The adherent COS-7 cells are transfected with 40 µg of DNA per 225 $cm^2$ flask, with a pGal4-hPPAR/Gal4(RE)_TkpGL3 ratio of 1/10, in the presence of 10% of fetal calf serum. The cells are then detached and seeded in the absence of serum in 384-well plates ($2 \times 10^4$ cells/well) then incubated for 4 hours at 37° C. The compounds are then diluted in a 96-well plate and then transferred to the 384-well plate. Activation with the test compounds is effected for a further 24 hours at 37° C. in the presence of 1% of synthetic serum Ultroser™ (Biosepra). These last 2 stages are automated by means of a Genesis Freedom 200™ station (Tecan). At the end of the experiment, the cells are lysed and the luciferase activity is determined using the Steady-Lite™ HTS (Perkin Elmer) according to the supplier's recommendations.

Results and Conclusion

The inventors thus demonstrated a significant, dose-dependent increase of luciferase activity in the cells transfected with the pGal4-hPPAR plasmids and treated with the compounds according to the invention. The test data are summarized in Table 8-1 below, which presents, for each compound, the values of maximum activation (TOP %) and the $EC_{50}$ values measured for each isoform of PPAR. The values of maximum activation are expressed in percentages relative to the maximum activations obtained with reference agonists: fenofibric acid for PPARα, rosiglitazone for PPARγ and 2-methyl-4-((4-methyl-2-(4-trifluoromethylphenyl)-1,3-thiazol-5-yl)-methylsulfanyl)phenoxyacetic acid (also called GW501516) for PPARδ.

TABLE 8-1

| | PPARα | | PPARγ | | PPARδ | |
|---|---|---|---|---|---|---|
| Compound No. | TOP % | EC50 µM | TOP % | EC50 µM | TOP % | EC50 µM |
| 2 | 48.29 | 0.143 | 39.15 | 12.4 | 108.56 | 2.00 |
| 3 | 68.71 | 0.432 | 43.64 | 3.24 | 113.83 | 1.20 |
| 4 | 66.66 | 1.47 | 70.47 | 17.7 | 114.90 | 8.67 |
| 5 | 67.52 | 0.389 | 57.27 | 3.72 | 70.97 | 6.17 |
| 6 | 30.27 | 5.43 | 17.28 | 11.8 | 70.72 | 0.489 |
| 7 | 28.85 | 39.6 | 20.65 | 46.8 | 96.49 | 0.550 |
| 8 | 21.94 | 7.92 | 13.36 | 12.2 | 72.39 | 2.11 |
| 9 | 33.72 | 4.50 | 23.87 | 6.09 | 74.16 | 0.464 |

TABLE 8-1-continued

| Compound No. | PPARα TOP % | PPARα EC50 µM | PPARγ TOP % | PPARγ EC50 µM | PPARδ TOP % | PPARδ EC50 µM |
|---|---|---|---|---|---|---|
| 10 | 53.23 | 6.06 | 25.65 | 10.5 | 96.74 | 0.754 |
| 11 | 86.19 | 0.022 | 54.51 | 2.45 | 85.67 | 3.00 |
| 12 | 78.06 | 0.195 | 44.92 | 2.64 | 84.16 | 2.36 |
| 13 | 61.87 | 1.43 | 24.15 | 6.93 | 96.12 | 3.22 |
| 14 | 58.41 | 33.3 | 53.67 | 24.3 | 102.80 | 16.2 |
| 15 | 78.15 | 3.24 | 46.58 | 12.3 | 96.55 | 1.52 |
| 16 | 78.03 | 0.510 | 70.03 | 5.18 | 85.15 | 3.37 |
| 17 | 66.84 | 0.009 | 75.61 | 0.583 | 99.60 | 0.992 |
| 18 | 35.30 | 10.7 | 26.08 | 14.2 | 97.12 | 3.97 |
| 19 | 67.98 | 2.37 | 86.95 | 1.29 | 95.12 | 3.13 |
| 20 | 34.19 | 14.3 | 42.98 | 30.2 | 87.68 | 5.26 |
| 21 | 70.17 | ND | 51.48 | 1.43 | 99.96 | 0.276 |
| 22 | 75.94 | ND | 88.88 | 1.05 | 102.03 | 1.15 |
| 23 | 65.27 | 0.044 | 75.58 | 2.84 | 85.44 | 0.501 |
| 24 | 76.78 | 0.371 | 65.74 | 4.49 | 94.08 | 0.784 |
| 25 | 53.90 | 6.96 | 38.34 | 8.29 | 71.03 | 6.38 |
| 26 | 66.97 | 20.9 | 208.15 | 44.1 | 137.99 | 31.1 |
| 27 | 99.78 | 3.64 | 98.68 | 10.6 | 72.87 | 41.1 |
| 28 | 55.37 | 1.74 | 45.03 | 11.3 | 49.14 | 25.2 |
| 29 | 59.30 | 3.85 | 57.71 | 8.43 | 85.61 | 10.11 |
| 30 | 38.70 | 12.1 | 7.28 | ND | 1.13 | ND |
| 31 | 49.52 | 2.49 | 62.35 | 3.36 | 86.72 | 16.3 |
| 32 | 70.40 | 1.48 | 66.62 | 2.51 | 3.59 | 22.8 |
| 33 | 49.93 | 4.55 | 64.95 | 12.4 | 74.46 | 10.5 |
| 34 | 67.58 | 1.42 | 80.40 | 2.33 | 107.79 | 0.526 |
| 35 | 26.15 | 0.647 | 38.80 | 6.18 | 13.16 | 1.54 |
| 36 | 77.98 | 0.304 | 123.27 | 1.52 | 93.88 | 0.595 |
| 37 | 65.47 | 9.95 | 98.51 | 9.17 | 94.71 | 12.7 |
| 38 | 36.24 | 10.8 | 45.37 | 7.60 | 64.54 | 6.78 |
| 39 | 52.19 | 0.175 | 100.29 | 1.94 | 95.28 | 1.39 |
| 40 | 66.70 | 0.165 | 87.25 | 0.955 | 107.35 | 0.080 |
| 41 | 35.90 | 7.36 | 72.14 | 27.2 | 107.40 | 17.0 |
| 42 | 16.53 | 5.66 | 65.78 | 4.36 | 86.55 | 3.04 |
| 43 | 44.93 | 1.44 | 85.61 | 0.402 | 77.90 | 1.51 |
| 44 | 55.48 | 0.929 | 72.21 | 2.64 | 80.64 | 2.38 |
| 45 | 43.20 | 6.43 | 79.38 | 2.39 | 97.34 | 3.36 |
| 46 | 60.00 | 0.622 | 69.37 | 1.94 | 107.16 | 0.028 |
| 47 | 58.64 | 1.90 | 84.98 | 1.08 | 79.17 | 1.91 |
| 48 | 35.92 | 26.4 | 58.17 | 9.57 | 68.11 | 16.7 |
| 49 | 51.13 | 3.62 | 73.20 | 4.04 | 122.96 | 0.408 |
| 50 | 46.76 | 0.771 | 63.71 | 1.92 | 103.28 | 0.77 |
| 51 | 50.50 | 1.29 | 70.94 | 2.23 | 93.12 | 1.93 |
| 52 | 34.31 | 13.7 | 54.80 | 2.76 | 16.07 | 19.8 |
| 53 | 48.64 | 5.14 | 77.95 | 1.01 | 9.86 | 10.3 |
| 54 | 34.51 | 7.97 | 42.17 | 4.85 | 92.14 | 3.20 |

The measured activities differ depending on the compound tested and the compounds according to the invention are also observed to have varying selectivity with respect to the various isoforms of hPPAR:

Certain compounds according to the invention are selective for a subtype of PPAR. This is the case for example for Cpd 11, which shows high selectivity for hPPARα; the latter activates hPPAR≡ and hPPARδ with $EC_{50}$ values more than 100 times higher than that measured on hPPARα. Similarly, Cpd 7 appears to be selective with respect to hPPARδ.

Other compounds according to the invention are simultaneously activators of two or three subtypes of PPAR. This is the case notably for Cpd19 and Cpd 1 which activates hPPARα, hPPARγ, and hPPARδ with comparable $EC_{50}$. Compound 1 of the invention was also tested for its PPAR agonist properties. Like Cpd 19, it displays comparable selectivities for the 3 PPAR isoforms. As the measurements obtained for compound 1 were carried out according to a different method and with different equipment, relative to the other 53 compounds in the examples, the corresponding results are not presented in Table 8-1 above.

The results obtained show that, in general, the compounds according to the invention bind and activate the hPPARα, hPPARγ, and/or hPPARδ receptors significantly.

Example 9

Antidiabetic Character of the Compounds According to the Invention

Principle

The aim of this study is to evaluate in vivo the antidiabetic character of the compounds according to the invention, in the db/db mouse (Berger J et al., 1996). The antidiabetic effect of the compounds is evaluated by measuring glycemia and insulinemia after 8 days of treatment. In diabetic animals (as in humans), administration of glucose leads to a significant increase in the plasma level of insulin. This induced hyperinsulinemia causes a lowering of glycemia, which is delayed in insulin-resistant animals, for example in the db/db mouse. The corrective action of the compounds on insulin resistance should notably be reflected in an improvement of glucose tolerance.

Protocol a) Treatment of the Animals

Male db/db mice (CERJ—Le Genest St Isle-France) are used for this experiment. After acclimation for one week, the mice were weighed and put into groups of 8 animals, selected in such a way that the distribution of their bodyweight and of their fasting glycemia determined for the first time before the experiment are uniform. The compound tested was suspended in carboxymethylcellulose (Sigma C4888) and administered by stomach tube, at a rate of once a day for 9 days at the chosen dose. The animals had free access to water and food (standard diet) and were housed in ventilated cages with a rhythm of light and darkness of 12 hours/12 hours at a constant temperature of 20±3° C. The food intake and weight gain were recorded throughout the experiment. After administration of the compound for 8 days, a blood sample was taken by puncture in the retro-orbital sinus of the animals under volatile anesthesia with isoflurane in order to measure the plasma concentrations of glucose and insulin.

After 9 days, the animals were deprived of food for 16 hours before carrying out the glucose tolerance test. The latter consists of a single administration of glucose after fasting (administered orally at a dose of 1 g/kg). Blood samples were then taken from time to time to study the evolution of plasma glycemia.

b) Measurement of Plasma Insulinemia

Assay of murine insulin is carried out by the Elisa method (Insulin Elisa Kit-Crystal Chem. USA). A mouse anti-insulin antibody is fixed on a microplate. The serum to be assayed for insulin is then deposited on this plate. A guinea pig anti-insulin antibody will recognize the insulin/mouse monoclonal anti-insulin antibody complex and bind to it. Finally a peroxidase-labeled anti-guinea pig antibody is added, and attaches to the guinea pig anti-insulin antibody. The colorimetric reaction is performed by adding the substrate of the enzyme OPD (Ortho Phenyl Diamine). The intensity of coloration is proportional to the amount of insulin present in the sample.

c) Measurement of Plasma Glycemia

Glucose was determined by enzyme assays (bioMérieux-Lyons-France) according to the suppliers recommendations.

Results and Conclusion

The aim of this study is to evaluate in vivo the antidiabetic character of a compound according to the invention (Cpd 24) by measuring glycemia and insulinemia after 8 days of oral treatment with the compound according to the invention. Unexpectedly, the test data obtained show that Cpd 24, administered at 30 mpk for 8 days, gives an overall improvement in the glycemic and insulinemic profiles of the diabetic animals. These results are also reflected in a decrease in the HOMA index, calculated from these plasma parameters, reflecting an improvement in sensitivity to insulin (FIGS. 8a, 8b and 8c).

In normal and diabetic animals (as in humans), the administration of glucose leads to a significant increase in the plasma level of insulin. This induced hyperinsulinemia causes a lowering of glycemia, which is delayed in insulin-resistant animals. The glucose tolerance test also shows a marked decrease in insulin resistance in the animals treated for 9 days with Cpd 24 (FIGS. 8d and 8e).

The compounds according to the invention possess antidiabetic properties, lowering the plasma levels of glucose and insulin. The compounds according to the invention also permit improvement in sensitivity to insulin. These results in vivo provide evidence of the therapeutic potential of the compounds according to the invention with respect to major pathologies such as type 2 diabetes.

Example 10

Hypolipemic Properties and Stimulating Effect on Synthesis of HDL-Cholesterol of the Compounds According to the Invention Principle The hypolipemic properties of the compounds according to the invention were evaluated in vivo by determination of plasma lipids and by analysis of gene expression of targets genes of PPARs in the liver after oral treatment of a dyslipidemic mouse with the compounds according to the invention.

The murine model used is the mouse of type ApoE2/E2, a mouse transgenic for the E2 isoform of human apolipoprotein E (Sullivan P M et al., 1998). In humans, this apolipoprotein, a constituent of low and very low density lipoproteins (LDL-VLDL), occurs in three isoforms E2, E3 and E4. The E2 form has a mutation on an amino acid in position 158, so that the affinity of this protein for the LDL receptor is greatly reduced. Because of this, clearance of VLDLs is almost zero. This leads to accumulation of low-density lipoproteins and mixed, so-called type III hyperlipidemia (raised cholesterol and triglycerides).

PPARα regulates the expression of genes involved in lipid transport (apolipoproteins such as Apo AI, Apo AII and Apo CIII, membrane transporters such as FAT) or the catabolism of lipids (ACO, CPT-I or CPT-II, enzymes of β-oxidation of fatty acids). Treatment with PPARα activators is therefore reflected, both in humans and in rodents, in a decrease in levels of circulating triglycerides. Measurement of plasma lipids after treatment with the compounds according to the invention is therefore an indicator of the PPARα agonist character and therefore of the hypolipemic action of the compounds according to the invention.

The PPARα agonist properties previously measured in vitro should be translated at the hepatic level by a change in the level of expression of the target genes directly under the control of the PPARα receptor: the genes that were studied in these experiments are those coding for ACO (a key enzyme in the mechanism of β-oxidation of fatty acids), PDK-4 (an enzyme of carbohydrate metabolism) and Apo CIII (apolipoprotein involved in lipid metabolism). This change in gene expression after treatment with the compounds according to the invention is therefore also an indicator of their hypolipemic character.

Protocol a) Treatment of the Animals

Apo E2/E2 transgenic mice were kept in a cycle of light and darkness of 12 hours/12 hours at a constant temperature of 20±3° C. After acclimation for one week, the mice were weighed and put into groups of 6 animals selected in such a way that the distribution of their bodyweight and of their plasma lipid values determined first before the experiment are uniform. The compounds tested were suspended in carboxymethylcellulose (Sigma C4888) and administered at the chosen dose by stomach tube, at a rate of once a day for 7 days at the chosen dose. The animals had free access to water and food. At the end of the experiment, the animals were anesthetized after fasting for 4 hours, a blood sample was taken on anticoagulant (EDTA), then the mice were weighed and euthanased. The plasma was separated by centrifugation at 3000 rev/min for 20 minutes, and the samples were stored at +4° C. for the biochemical assays. Samples of liver were taken and frozen immediately in liquid nitrogen and then stored at −80° C. for subsequent analyses.

b) Measurement of Plasma Lipids

The plasma concentrations of lipids (total cholesterol, HDL-cholesterol, and free fatty acids) were measured by enzyme assays (bioMérieux-Lyons-France) according to the supplier's recommendations.

c) Analysis of Gene Expression by Quantitative RT-PCR

Total RNA was extracted from fragments of liver using the NucleoSpin® 96 RNA kit (Macherey Nagel, Hoerdt, France) according to the manufacturer's instructions. 1 μg of total RNA (quantified using the Ribogreen RNA quantification kit (Molecular Probes)) was then reverse transcribed to complementary DNA by a reaction of 1 hour at 37° C. in a total volume of 20 μl containing buffer 1× (Sigma), 1.5 mM of DTT, 0.18 mM of dNTPs (Promega), 200 ng of pdN6 (Amersham), 30U of RNase inhibitor (Sigma) and 1 μl of MMLV-RT (Sigma).

The quantitative PCR experiments were performed using the MyiQ Single-Color Real-Time PCR Detection System (Biorad, Marnes-la-Coquette, France) and were carried out using the iQ SYBR Green Supermix kit according to the supplier's recommendations, in 96-well plates, on 5 μl of diluted reverse transcription reaction mixtures, with a hybridization temperature of 55° C. Specific primer pairs of the genes under investigation were used:

```
PDK4:
                                         (SEQ ID NO: 1)
sense primer:    5'-TACTCCACTGCTCCAACACCTG-3'
and
                                         (SEQ ID NO: 2)
antisense primer 5'-GTTCTTCGGTTCCCTGCTTG-3'

ACO:
                                         (SEQ ID NO: 3)
sense primer:    5'-GAAGCCAGCGTTACGAGGTG-3'
and
                                         (SEQ ID NO: 4)
antisense primer 5'-TGGAGTTCTTGGGACGGGTG-3'

ApoCIII:
                                         (SEQ ID NO: 5)
sense primer:    5'-CTCTTGGCTCTCCTGGCATC-3'
and
                                         (SEQ ID NO: 6)
antisense primer 5'-GCATCCTGGACCGTCTTGGA-3'
```

The amount of fluorescence emitted is directly proportional to the amount of complementary DNA present at the start of the reaction and amplified during PCR. For each target investigated, a range is prepared by successive dilutions of a pool consisting of a few μl of different reverse transcription reactions. The relative levels of expression of each target are thus determined using the curves of efficacy obtained with the scale points.

The levels of expression of the genes of interest were then normalized relative to the level of expression of the 36B4 reference gene (whose specific primers are:

```
                                            (SEQ ID NO: 11)
sense primer:     5'-CATGCTCAACATCTCCCCCTTCTCC-3'
and
                                            (SEQ ID NO: 12)
antisense primer: 5'-GGGAAGGTGTAATCCGTCTCCACAG-3'.
```

The induction factor, i.e. the ratio of the relative signal (induced by the compound according to the invention) to the mean of the relative values of the control group, was then calculated for each sample. The higher this factor, the more the compound has a character of activation of gene expression. The final result is represented as the mean of the induction values in each experimental group.

Results and Conclusion
a) Measurement of Plasma Lipids

Figure 10A:
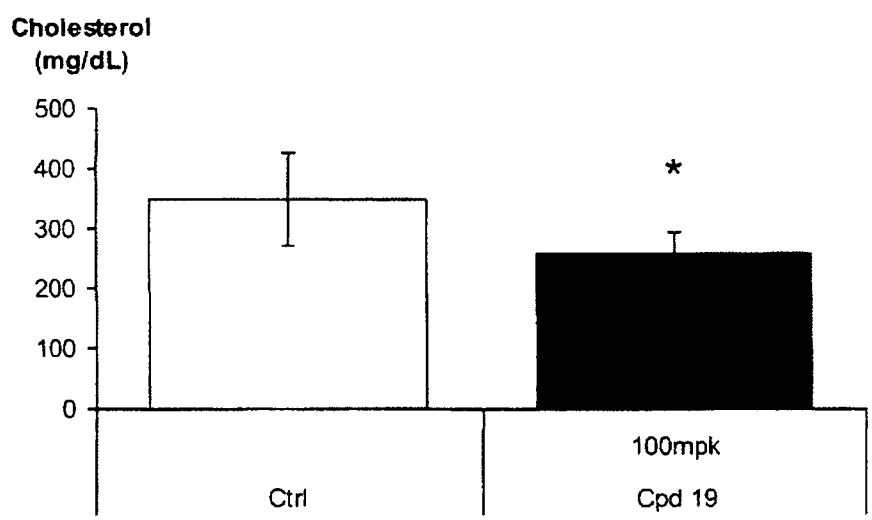
Figure 10B:
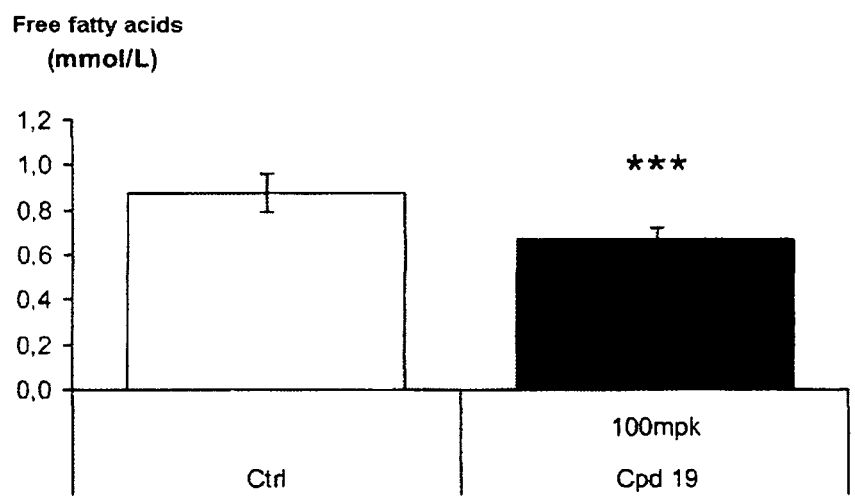

The levels of total cholesterol were decreased after 7 days of treatment with compounds 2 and 4 (administered at 10 and 100 mpk; FIG. 9a) and with compound 19 administered at 100 mpk (FIG. 10a). Furthermore, treatment with Cpd 2 or with Cpd 4 led to a dose-dependent increase in plasma level of HDL-cholesterol (FIG. 9b). Treatment with Cpd 19, at 100 mpk, also led to a decrease in plasma level of free fatty acids (FIG. 10b).

b) Analysis of Gene Expression by Quantitative RT-PCR

Cpd 2 and Cpd 4 induce hepatic overexpression of genes coding for ACO and PDK-4, and significant inhibition of hepatic expression of the gene coding for ApoCIII ((FIGS. 9c, 9d, and 9e).

The compounds according to the invention have hypolipemic properties, lowering the plasma levels of cholesterol and of free fatty acids. The compounds according to the invention also have the property of increasing the beneficial fraction of HDL-cholesterol. Moreover, the compounds according to the invention are regulators of expression of genes coding for enzymes strongly involved in lipid and carbohydrate metabolism. These results, obtained in vivo, provide evidence of the therapeutic potential of the compounds according to the invention with respect to major pathologies such as dyslipidemias.

Example 11

Pparδ Activating Properties of the Compounds According to the Invention From Measurement of the Expression of Target Genes of Pparδ in Myocytes Principle The PPARδ agonist properties previously measured in vitro were evaluated by measuring, in murine myocytes, the expression of genes involved in lipid and carbohydrate metabolism and energy expenditure (PDK4, CPT1b, UCP2). Regulation of expression of these genes, in this cell type, is a direct consequence of the activation of PPARδ by the compounds according to the invention. The greater the increase in expression of the genes, the more the compound according to the invention is a stimulator of metabolism in muscle cells (Dressel U et al., 2003).

Protocol
a) Differentiation of C2C12 Cells into Myocytes

The C2C12 murine cells (from ECACC) are cultivated in DMEM medium (Gibco; 41965-039) supplemented with 1% L-glutamine (Gibco; 25030), 1% penicillin/streptomycin (VWR; BWSTL0022/100) and 10% decomplemented fetal calf serum (FCS. Gibco; 10270-106).

The cells are seeded in 24-well plates at a density of $50 \times 10^3$ cells/well. At confluence, the medium is replaced with a differentiation medium (base culture medium supplemented with 2% of horse serum (Gibco; 26050-088)) then culture is continued at 37° C. and 5% $CO_2$ for 7 days in order to permit differentiation of the myoblasts into myocytes.

b) Treatment

After 6 days of differentiation, the cells are put in a deprivation medium (base culture medium without serum) for 6 hours. The cells are then treated with the compounds according to the invention in the deprivation medium. The compounds according to the invention were tested at doses of 0.1, 1, 10 μM and 0.2, 2 and 20 μM respectively. The compounds according to the invention were dissolved in dimethylsulfoxide (DMSO, Sigma; D5879). The cells are treated for 24 hours at 37° C., 5% $CO_2$. The effects for the compounds tested were compared with the effect of DMSO alone at a concentration of 0.1%.

c) Extraction of RNA, Reverse Transcription and Quantitative PCR

These procedures were performed on the cells essentially as described in Example 10 (point c) of the Protocols.

The following primer pairs specific to the genes investigated were used:

```
PDK4:
                                            (SEQ ID NO: 1)
sense primer:     5'-TACTCCACTGCTCCAACACCTG-3'
and
                                            (SEQ ID NO: 2)
antisense primer 5'-GTTCTTCGGTTCCCTGCTTG-3'

CPT1b:
                                            (SEQ ID NO: 7)
sense primer:     5'-GGACTGAGACTGTGCGTTCCTG-3'
and
                                            (SEQ ID NO: 8)
antisense primer 5'-AGTGCTTGGCGGATGTGGTT-3'

UCP2:
                                            (SEQ ID NO: 9)
sense primer:     5'-GTCGGAGATACCAGAGCACTGTCG-3'
and
                                            (SEQ ID NO: 10)
antisense primer 5'-CACATCAACAGGGGAGGCGA-3'
```

Results and Conclusion

Figure 11A:
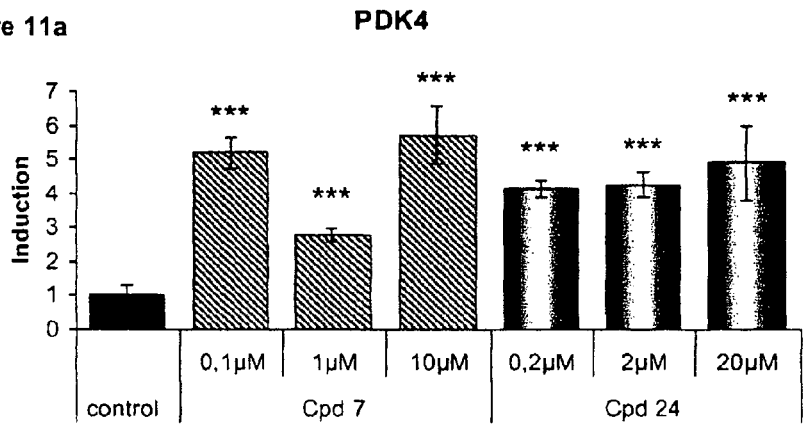
Figure 11B:
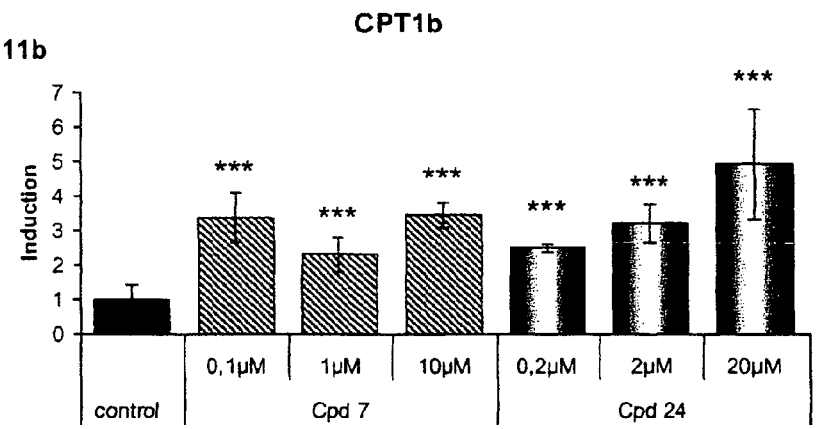
Figure 11C:
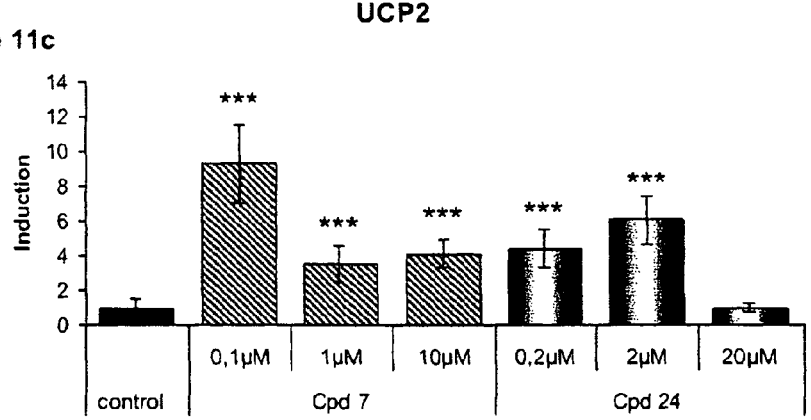

In murine myocytes in vitro, that the compounds of the invention such as Cpd 7 and Cpd 24 possess significant effects of stimulating expression of genes involved in carbohydrate and lipid metabolism and in thermoregulation, and known to be regulated by agonists of PPARδ, such as PDK4, CPT1b and UCP2 (FIGS. 11a, 11b and 11c).

The test data presented show that the compounds of the invention have a metabolic action in murine myocytes by activation of PPARδ.

Example 12

PPARγ Activating Properties of the Compounds According to the Invention

Principle

The functional effect of activation of PPARγ is evaluated in vitro on a line of pre-adipocyte cells 3T3-L1 (Thompson G M et al., 2004) by measuring the concentration of intracellular triglycerides and the concentration of adiponectin secreted in the culture medium after 9 days of treatment with the compounds according to the invention. This effect, similar to that of PPARγ agonist compounds such as thiazolidinediones (Kallen C B and Lazar M A, 1996), demonstrated in vitro the functional properties of these compounds.

Protocol

The 3T3-L1 cells (Mus musculus embryo fibroblasts, ATCC; CL-173) are cultivated in DMEM medium (4.5 g/L glucose, Gibco 41965) supplemented with 10% of fetal calf serum (Gibco; 10270), 1% of L-glutamine (Gibco; 25030), 100 units/mL of penicillin+100 µg/mL streptomycin (VWR; BWSTL0022/100) up to confluence (37° C., 5% $CO_2$). At confluence, the cells were then rinsed with PBS (Phosphate Buffered Saline solution) and the culture medium was replaced with DMEM 4.5 g/L glucose (10% FCS, 1% L-glutamine, 100 units/mL penicillin and 100 µg/mL streptomycin, 0.25 mM) containing a cocktail for initiation of adipocyte differentiation (IBMX (3-isobutyl-1-methylxanthine Sigma; 17018), 0.1 µM dexamethasone (Sigma; D1756) and 0.4 µM of insulin (Sigma; I2643). The cells were also treated with the compounds according to the invention (1 µL of solubilized compound/mL of medium, 200 µL per well).

After 2 days of incubation, the cells were washed with PBS and the differentiation medium was replaced with DMEM 4.5 g/L of glucose supplemented with 10% FCS, 1% L-glutamine, 100 units/mL penicillin and 100 µg/mL streptomycin, 0.4 µM insulin, and the compounds according to the invention for the purpose of completing cellular differentiation and obtaining adipocytes. The medium was changed every 2 days until total differentiation. After culture for 9 days, the treatment was stopped by withdrawing the culture medium, which was stored for assaying secreted adiponectin. The cells were then washed twice with PBS and placed in isopropanol for membrane permeabilization. The content of intracellular triglycerides was evaluated immediately.

Quantification of intracellular triglycerides was performed with the "Triglyceride Enzymatic PAP1000" kit (bioMérieux; 61238) according to the supplier's recommendations. Secreted adiponectin was measured in the culture medium using the "Mouse Adiponectin/Acrp30 Elisa Kit" kit (R&D Systems; DY1119) according to the supplier's recommendations.

Results and Conclusion

The test data show that Cpd 19, Cpd 24 and Cpd 36 produce dose-dependent stimulation in vitro of accumulation of triglycerides in adipocytes, and secretion of adiponectin. These results therefore show a PPARγ activating capacity in vitro of the compounds according to the invention, which is reflected in stimulation of adipogenesis in the cellular model of 3T3-L1 murine pre-adipocytes.

BIBLIOGRAPHY

Berger J et al., Endocrinology. 1996, 137(10), 4189-95.
Blaschke F et al., Arterioscler Thromb Vasc Biol. 2006, 26, 28-40.
Burger A, Prog Drug Res. 1991, 37, 287-371
Dressel U et al., Mol Endocr. 2003, 17(12):2477-2493.
Gervois P et al., Nat Clin Pract Endocrinol Metab, 2007, 3 (2) 145-156.
Gilde A J et al., J Am Coll Cardiol. 2006, 48(9), A24-A32.
Gross B et al., Drug Disc Today: Therapeutic Strategies, 2005, 2 (3), 237-243.
Hansen M K and Connolly T M, Curr Opin Invest Drugs. 2008, 9(3), 247-255.
Hourton D et al. Biochem J 2001? 354(Pt1), 225-232.
Kallen C B and Lazar M A, Proc Natl Acad Sci USA. 1996, 93(12), 5793-6.
Krause B, Curr Opin Invest Drugs. 2008, 9(9), 945-9.
Lefebvre P et al., J Clin Invest, 2006, 116 (3), 571-580
Lehrke M and Lazar M A, Cell, 2005, 123 (6), 993-999.
Lima L M and Barreiro E J, Curr Med Chem. 2005, 12(1), 23-49.
Peraza M et al., Toxicol. Sci., 2006, 90(2), 269-295.
Raspe E J Lipid Res, 1999, 40 (11), 2099-110.
Sullivan P M et al., J Clin Invest. 1998, 102(1), 130-5.
Thompson G M et al., Anal Biochem. 2004, 330(1), 21-8.

---

The invention claimed is:

1. A compound of formula:

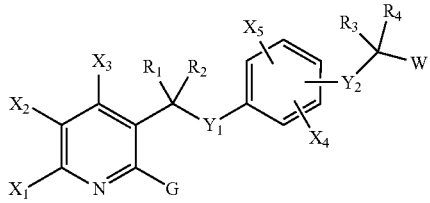

(I)

in which,

G represents:
  a radical —$OR_a$, —$SR_a$, or
  a radical —$NR_aR_b$,
$R_a$ being selected from an alkyl radical with 1 to 6 carbon atoms or alkenyl radical with 2 to 6 carbon atoms, a ring with 3 to 14 atoms, a phenyl radical, a phenylalkyl radical with the alkyl moiety having 1 to 3 carbon atoms;
$R_b$ being selected from a hydrogen atom, an alkyl radical with 1 to 6 carbon atoms or alkenyl radical with 2 to 6 carbon atoms, a ring with 3 to 14 atoms, a phenyl radical, or a phenylalkyl radical with the alkyl moiety having 1 to 3 carbon atoms; or
$R_a$ and $R_b$ can form, together and with the nitrogen atom to which they are bound, a heterocycle with 3 to 8 atoms.
$R_1$ and $R_2$, which may be identical or different, represent a hydrogen atom or an alkyl radical with 1 to 6 carbon atoms or alkenyl radical with 2 to 6 carbon atoms; or
$R_1$ and $R_2$ can form, together and with the carbon atom to which they are bound, a carbocycle with 3 to 6 carbon atoms;
$Y_1$ represents:
  a oxygen atom or sulfur atom, or
  a group —NR—, in which R has the same definition as $R_b$;
$Y_2$ represents:
  a oxygen atom or sulfur atom, or
  a radical —$CR_5R_6$—; with $R_5$ and $R_6$, which may be identical or different, selected from a hydrogen atom or halogen atom, an alkyl radical with 1 to 6 carbon atoms or an alkenyl or alkynyl radical with 2 to 6 carbon atoms, a ring with 3 to 6 atoms, a phenyl radical, a phenylalkyl radical with the alkyl moiety having 1 to 3 carbon atoms;
$X_1$, $X_2$, $X_3$ represent independently a hydrogen atom or halogen atom, an alkyl radical with 1 to 6 carbon atoms or alkenyl radical with 2 to 6 carbon atoms, a group —OR'$_a$, —SR'$_a$, —NR'$_a$R'$_b$, a ring with 5 to 14 atoms, or a phenylalkyl radical with the alkyl moiety having 1 to 3 carbon atoms,
with at least one of the groups $X_1$, $X_2$ and $X_3$ different from a hydrogen atom and from a halogen atom;
R'$_a$ and R'$_b$, which may be identical or different, having the same definitions as R$_a$ and R$_b$;
$X_4$ and $X_5$ represent independently a hydrogen atom or halogen atom, an alkyl radical with 1 to 6 carbon atoms or alkenyl radical with 2 to 6 carbon atoms, a group —OR"$_a$, —SR"$_a$ or —NR"$_a$R"$_b$, a ring with 3 to 14 atoms, a phenyl radical, or a phenylalkyl radical with the alkyl moiety having 1 to 3 carbon atoms;
R"$_a$ and R"$_b$, which may be identical or different, having the same definitions as R$_a$ and R$_b$;
$R_3$ and $R_4$, which may be identical or different, represent a hydrogen atom or halogen atom, an alkyl radical with 1 to 6 carbon atoms or alkenyl radical with 2 to 6 carbon atoms, a ring with 3 to 14 atoms, a phenyl radical, or a phenylalkyl radical with the alkyl moiety having 1 to 3 carbon atoms;
W represents:
a carboxyl radical —COOH; or
a function derived from the carboxylic acid function, selected from —COOR'''$_a$, —COSR'''$_a$, —CONR'''$_a$R'''$_b$, —CSNR'''$_a$R'''$_b$, —CONH$_2$; or
a bioisosteric group of the carboxyl radical, selected from:
an acylsulfonamide radical (—CONHSO$_2$R'''$_a$);
a hydrazide radical (—CONHNR'''$_a$R'''$_b$);
a radical selected from the thiazolidinedione, oxazolidinedione, tetrazole, oxadiazolone, triazolone, triazole, 3-alkyltriazole, or imidazolidinedione rings;
R'''$_a$ and R'''$_b$, which may be identical or different, having the same definitions as R$_a$ and R$_b$.

2. The compound of claim 1, wherein $Y_2$ is positioned para or meta of $Y_1$.

3. The compound of claim 1, wherein:
$X_3$ denotes a hydrogen atom, and/or
$X_4$ and $X_5$ denote independently a hydrogen atom, an alkyl radical having 1 to 6 carbon atoms, a group —OR"$_a$ or —SR"$_a$; R"$_a$ being an alkyl radical having 1 to 6 carbon atoms, and optionally wherein
$Y_2$ is positioned para or meta of $Y_1$.

4. The compound of claim 1, wherein $R_1$, $R_2$, $R_3$, $R_4$ denote independently a hydrogen atom or a methyl, ethyl, propyl, butyl, isopropyl or tert-butyl radical.

5. The compound of claim 1, wherein $X_3$, $R_1$ and $R_2$ denote hydrogen atoms.

6. The compound of claim 1, wherein $X_1$ and/or $X_2$ denote a ring with 5 to 10 atoms, unsubstituted or substituted with a —CF$_3$ group.

7. The compound of claim 1, wherein G denotes
a radical —OR$_a$ or —SR$_a$, with R$_a$ selected from alkyl radical having 1 to 6 carbon atoms, a cyclohexyl or a phenyl radical; or
a radical —NR$_a$R$_b$, R$_a$ and R$_b$ forming together, and with the nitrogen atom to which they are bound, a heterocycle with 3 to 8 atoms.

8. The compound of claim 1, wherein G denotes a radical —OR$_a$ with R$_a$ selected from a methyl, ethyl, propyl, butyl, isopropyl or tert-butyl radical.

9. The compound of claim 7, wherein:
$X_2$ and $X_3$ denote simultaneously a hydrogen atom; or
$X_3$ and $X_1$ denote simultaneously a hydrogen atom.

10. The compound of claim 1, characterized in that $Y_1$ denotes an oxygen or sulfur atom, and simultaneously $Y_2$ denotes an oxygen atom, a sulfur atom, or a group —CR$_5$R$_6$.

11. The compound of claim 1, characterized in that $Y_1$ denotes a group —NR and simultaneously $Y_2$ denotes an oxygen atom, a sulfur atom or a group —CR$_5$R$_6$.

12. The compound of claim 10, characterized in that $X_1$ denotes an unsubstituted phenyl radical or a phenyl radical substituted with a group —CF$_3$, and/or G denotes a group —OCH$_3$ or —OC(CH$_3$)$_3$.

13. The compound of claim 1, wherein it is selected from:
Cpd 1: 2-(4-((2-methoxy-6-phenylpyridin-3-yl)methoxy)phenoxy)-2-methyl-propanoic acid
Cpd 2: 2-(4-((2-methoxy-6-phenylpyridin-3-yl)methoxy)phenoxy)ethanoic acid
Cpd 3: 2-(4-((2-methoxy-6-phenylpyridin-3-yl)methoxy)phenoxy)propanoic acid
Cpd 4: 2-(4-(((2-methoxy-6-phenylpyridin-3yl)methyl)amino)phenoxy)ethanoic acid
Cpd 5: 2-(4-(((2-methoxy-6-phenylpyridin-3yl)methyl)amino)phenoxy)propanoic acid
Cpd 6: 2-(4-((2-tert-butyloxy-6-phenylpyridin-3-yl)methoxy)phenoxy)-2-methyl-propanoic acid
Cpd 7: 2-(4-(((2-tert-butyloxy-6-phenylpyridin-3-yl)methoxy)phenoxy)ethanoic acid
Cpd 8: 2-(4-((2-tert-butyloxy-6-phenylpyridin-3-yl)methyl)amino) phenoxy)ethanoic acid
Cpd 9: 2-(4-(((2-tert-butyloxy-6-phenylpyridin-3-yl)methyl)amino)phenoxy)-2-methyl-propanoic acid
Cpd 10: 2-(4-(((2-tert-butyloxy-6-phenylpyridin-3-yl)methyl)amino)phenoxy)-propanoic acid
Cpd 11: 2-(4-(((2-methoxy-6-phenylpyridin-3-yl)methyl)amino)phenylthio)-2-methyl-propanoic acid
Cpd 12: 2-(4-(((2-methoxy-6-phenylpyridin-3-yl)methyl)amino)phenoxy)-2-methyl-propanoic acid
Cpd 13: 2-(3-(((2-methoxy-6-phenylpyridin-3-yl)methyl)amino)phenoxy)-2-methyl-propanoic acid
Cpd 14: 2-(3-(((2-methoxy-6-phenylpyridin-3-yl)methyl)amino)phenoxy)ethanoic acid
Cpd 15: 2-(4-((2-hexyloxy-6-phenylpyridin-3-yl)methoxy)phenoxy)ethanoic acid
Cpd 16: 2-(4-(((2-methoxy-6-phenylpyridin-3-yl)methyl)amino)phenylthio)-ethanoic acid
Cpd 17: 2-(4-((2-hexyloxy-6-phenylpyridin-3-yl)methoxy)phenoxy)-2-methyl-propanoic acid
Cpd 18: 2-(4-((2-cyclohexyloxy-6-phenylpyridin-3-yl)methoxy)phenoxy)ethanoic acid
Cpd 19: 3-(4-(((2-methoxy-6-phenylpyridin-3-yl)methyl)amino)phenyl)propanoic acid
Cpd 20: 2-(4-((6-phenyl-2-(piperidin-1-yl)pyridin-3-yl)methoxy)phenoxy)-ethanoic acid
Cpd 21: 2-(4-((2-methoxy-6-(4-(trifluoromethyl)phenyl)pyridin-3-yl)methoxy)-phenoxy)-2-methylpropanoic acid
Cpd 22: 2-(4-(((2-methoxy-6-(4-(trifluoromethyl)phenyl)pyridin-3-yl)methyl)amino)-phenylthio)-2-methylpropanoic acid
Cpd 23: 2-(4-(((2-methoxy-6-(4-(trifluoromethyl)phenyl)pyridin-3-yl)methyl)amino)-phenylthio)ethanoic acid
Cpd 24: 2-(4-((2-methoxy-6-(4-(trifluoromethyl)phenyl)pyridin-3-yl)methoxy)-phenoxy)ethanoic acid
Cpd 25: 2-(4-((2-phenylthio-6-(phenyl)pyridin-3-yl)methoxy)phenoxy)ethanoic acid
Cpd 26: 2-(4-(((2-methoxy-5-phenylpyridin-3-yl)methyl)amino)phenylthio)-ethanoic acid
Cpd 27: 2-(4-(((2-methoxy-6-phenylpyridin-3-yl)methyl)amino)phenylthio)-2,2-difluoroethanoic acid Cpd 28: 2-(4-(((2-methoxy-5,6-diphenylpyridin-3-yl)methyl)amino)phenylthio)-ethanoic acid
Cpd 29: 2-(4-(((2-methoxy-5-bromo-6-phenylpyridin-3-yl)methyl)amino)-phenylthio)-ethanoic acid
Cpd 30: 2-(4-(((2-methoxy-6-furylpyridin-3-yl)methyl)amino)phenylthio)ethanoic acid
Cpd 31: 3-(4-(((2-methoxy-6-furylpyridin-3-yl)methyl)amino)phenyl)propanoic acid
Cpd 32: 2-(4-(((2-methoxy-6-phenylpyridin-3-yl)methyl)amino)phenylthio)-2-phenyl-ethanoic acid
Cpd 33: 3-(4-(((2-methoxy-6-phenylpyridin-3-yl)methyl)(methyl)amino)phenyl)-propanoic acid
Cpd 34: 3-(4-(1-((2-methoxy-6-phenylpyridin-3-yl)propyl)amino)phenyl)propanoic acid
Cpd 35: 2-(4-(((2-methoxy-6-phenylpyridin-3-yl)methyl)amino)-2,6-dimethyl-phenoxy)ethanoic acid
Cpd 36: 3-(4-(((2-methoxy-6-(4-(trifluoromethyl)phenyl)pyridin-3-yl)methyl)amino)-phenyl)-propanoic acid
Cpd 37: 3-(4-((2-methoxy-6-phenylpyridin-3-yl)methylthio)phenyl)propanoic acid
Cpd 38: 3-(4-(((2-(ethylthio)-6-phenylpyridin-3-yl)methyl)amino)phenyl)-propanoic acid
Cpd 39: 3-(4-(((2-methoxy-6-(parabiphenyl)pyridin-3-yl)methyl)amino)phenyl)-propanoic acid
Cpd 40: 3-(4-(((2-methoxy-6-(3-(trifluoromethyl)phenyl)pyridin-3-yl)methyl)-amino)-phenyl)propanoic acid
Cpd 41: 3-(4-(((2-methoxy-5-phenylpyridin-3-yl)methyl)amino)phenyl)propanoic acid
Cpd 42: 3-(4-((2(-methoxy-6-phenylpyridin-3-yl)methyl)amino)phenyl)-3-phenyl-propanoic acid
Cpd 43: 3-(2-methoxy-4-(((2-methoxy-6-phenylpyridin-3-yl)methyl)amino)-phenyl)-propanoic acid
Cpd 44: 3-(3-methoxy-4-(((2-methoxy-6-phenylpyridin-3-yl)methyl)amino)-phenyl)-propanoic acid
Cpd 45: 3-(4-(((2-methoxy-6-phenylpyridin-3-yl)methyl)amino)phenyl)butanoic acid
Cpd 46: 3-(4-(((2-methoxy-5-(4-(trifluoromethyl)phenyl)pyridin-3-yl)methyl)-amino)phenyl)propanoic acid
Cpd 47: 3-(4-(((2-methoxy-5-(3-(trifluoromethyl)phenyl)pyridin-3-yl)methyl)-amino)-phenyl)propanoic acid
Cpd 48: 3-(4-(((2,6-dimethoxy-5-phenylpyridin-3-yl)methyl)amino)phenyl)-propanoic acid
Cpd 49: 3-(4-(((5-(4-chlorophenyl)-2-methoxypyridin-3-yl)methyl)amino)phenyl)-propanoic acid
Cpd 50: 3-(4-(((2-methoxy-5-(naphthalen-2-yl)pyridin-3-yl)methyl)amino)phenyl)-propanoic acid
Cpd 51: 3-(4-(((2-ethoxy-6-phenylpyridin-3-yl)methyl)amino)phenyl)propanoic acid
Cpd 52: 3-(4-((2-methoxy-5-phenylpyridin-3-yl)methoxy)phenyl)hex-4-ynoic acid
Cpd 53: 3-(4-((2-methoxy-6-phenylpyridin-3-yl)methoxy)phenyl)hex-4-ynoic acid
Cpd 54: 3-(4-(((2-isopropyloxy-6-phenylpyridin-3-yl)methyl)amino)phenyl)-propanoic acid.

14. A pharmaceutical composition comprising, in a pharmaceutically acceptable carrier, at least one compound as defined in claim 1, optionally in combination with one or more other therapeutic and/or cosmetic active substances.

15. The pharmaceutical composition of claim 14 for the therapeutic, curative and/or prophylactic treatment of diabetes, dyslipidemias, insulin resistance, pathologies associated with metabolic syndrome, atherosclerosis, cardiovascular diseases, obesity, hypertension and/or inflammatory diseases.

16. A method of therapeutic and/or prophylactic treatment of diabetes, dyslipidemias, insulin resistance, pathologies associated with metabolic syndrome, atherosclerosis, and cardiovascular diseases, obesity, hypertension and/or inflammatory diseases, comprising the administration, to a human subject, of an effective amount of a compound as defined in claim 1.

17. The compound of claim 12, characterized in that said group —$CF_3$ is in para of the pyridinyl radical.

* * * * *